US008900596B2

(12) United States Patent
Schein et al.

(10) Patent No.: US 8,900,596 B2
(45) Date of Patent: Dec. 2, 2014

(54) PHYSICOCHEMICAL (PCP) BASED CONSENSUS SEQUENCES AND USES THEREOF

(75) Inventors: Catherine H. Schein, Friendswood, TX (US); Petr Danecek, Prague (CZ)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/510,684

(22) PCT Filed: Nov. 18, 2010

(86) PCT No.: PCT/US2010/003001

§ 371 (c)(1),
(2), (4) Date: Nov. 19, 2012

(87) PCT Pub. No.: WO2011/062625

PCT Pub. Date: May 26, 2011

(65) Prior Publication Data

US 2013/0071418 A1 Mar. 21, 2013

Related U.S. Application Data

(60) Provisional application No. 61/281,555, filed on Nov. 18, 2009.

(51) Int. Cl.

| | |
|---|---|
| ***A61K 39/12*** | (2006.01) |
| ***A61K 39/42*** | (2006.01) |
| ***C07K 14/18*** | (2006.01) |
| ***G06F 19/22*** | (2011.01) |
| ***G01N 33/569*** | (2006.01) |
| ***C07K 16/10*** | (2006.01) |
| ***C07K 14/005*** | (2006.01) |
| *G06F 19/16* | (2011.01) |

(52) U.S. Cl.

CPC ............ *C07K 14/1825* (2013.01); *G06F 19/22* (2013.01); *G01N 2469/20* (2013.01); *G01N 33/56983* (2013.01); *G06F 19/16* (2013.01); *C07K 16/1081* (2013.01); *C12N 2770/24122* (2013.01); *G01N 2333/185* (2013.01); *C07K 2317/33* (2013.01); *C07K 14/005* (2013.01)

USPC .................. 424/218.1; 424/186.1; 424/159.1

(58) Field of Classification Search

None

See application file for complete search history.

(56) References Cited

U.S. PATENT DOCUMENTS

| | | | | |
|---|---|---|---|---|
| 7,424,369 B2 | 9/2008 | Braun et al. | | |
| 7,476,499 B2 * | 1/2009 | Kirkegaard et al. | .............. | 435/5 |

FOREIGN PATENT DOCUMENTS

| | | |
|---|---|---|
| WO | WO2003102166 | * 12/2003 |
| WO | WO2007035530 | * 3/2007 |
| WO | WO2009134717 | * 11/2009 |

OTHER PUBLICATIONS

Chu et al., "Genetic Relatedness among structural protein genes of dengue 1 virus strains," J. Gen Virol, 70: pp. 1701-1712 (1989).*

(Continued)

*Primary Examiner* — Michelle S Horning
*Assistant Examiner* — M. Franco Salvoza

(57) ABSTRACT

Provided herein is a computational method for designing a PCP-consensus protein for a family of related proteins. The method uses a consensus alignment of a protein domain common to all the related proteins, which may or may not be substantially biased, from which an average value of p, e.g., 5, physicochemical properties are calculated for each amino acid in the alignment. The PCP-consensus protein has a sequence derived from an alignment of protein domains from a family of related proteins, said sequence containing one or more motifs common to all of the proteins. Also provided are the PCP-consensus proteins, kits comprising the same, datasets of aligned consensus sequences used to derive the PCP-consensus proteins and methods of eliciting an immune response, diagnosing or treating an infectious disease using the same.

4 Claims, 23 Drawing Sheets

(56) References Cited

OTHER PUBLICATIONS

PCT/US2012/003001 Written Opinion of the International Searching Authority.
Barrett, A D. T. (2008). Nature Biotechnology 26, 525-526.
Beasley et al. (2008). Expert Opinion on Biological Therapy 8, 95-106.
Danecek P, Schein CH. Flavitrack analysis of the structure and function of West Nile non-structural proteins. Int J Bioinform Res Appl. 2010;6(2):134-46.
Danecek et al. PCP consensus sequences of flaviviruses: correlating variance with vector competence and disease phenotype. J Mol Biol. Feb. 26, 2010;396(3):550-63. Epub Dec. 4, 2009.
Delano, W. L. (2002). The PyMOL Molecular Graphics System. DeLano Scientific, Palo Alto, CA, USA.
El Garch et al. (2008). Veterinary Immunology and Immunopathology 123, 230-239.
Mathura et al. (2003) Identifying property based sequence motifs in protein families and superfamilies: application to DNase-1 related endonucleases. Bioinformatics. Jul. 22, 2003;19(11):1381-90.
Oezguen et al. (2008). Mol Immunol, 45, 3740-7.
Schein et al. (2001 ). Biophysical Journal 81, 463-472.
Schein CH. Total sequence decomposition distinguishes functional modules, "molegos" in apurinic/apyrimidinic endonucleases. BMC Bioinformatics. Nov. 25, 2002;3:37. Epub Nov. 25, 2002.
Schein CH. Molego-based definition of the architecture and specificity of metal-binding sites. Proteins. Jan. 1, 2005;58(1):200-10.
Schein CH, et al. Stereophysicochemical variability plots highlight conserved antigenic areas in Flaviviruses. Virol. J. 2005;2:40.
Soman et al. (2000). Biophys. J. 79, 1601-1609.
Stoermer et al. (2008). Journal of Medicinal Chemistry 51, 5714-5721.
Tang et al. (2008). American Journal of Tropical Medicine and Hygiene, 78, 999-1001.
Venkatarajan M, Braun W (2001) New quantitative descriptors of amino acids based on multidimensional scaling of a large number of physical—chemical properties. Journal of Molecular Modeling 7: 445-453.
Widman et al. (2008). Vaccine 26, 2762-2771.
Wiggan et al. (2007). American Journal of Tropical Medicine and Hygiene 77, 135-135.

* cited by examiner

SEQ ID NOS: 1-10

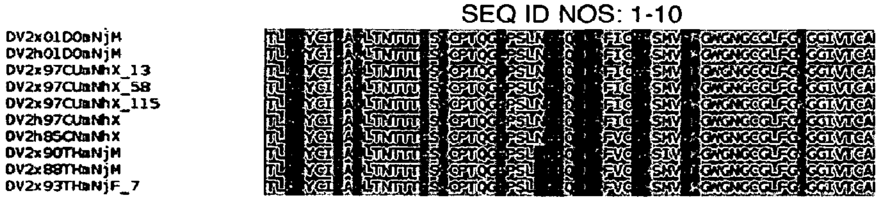

Start: alignment of sequences for a protein domain; for each column:

1 $\bar{E}^p = \sum_{j=1}^{m} \frac{E_j^p}{m}$ Determine the average value of each of five physicochemical property vectors 2 $|A_a, \bar{E}| = \sqrt{\sum_{p=E1}^{E5} b_p \left|E_a^p - \bar{E}^p\right|^2}$ Determine Euclidean distances ir 5D-space and select the amino acid closest to all others 3 Repeat at each position to obtain a PCP-consensus sequence Virus-CON: TLRKYCIEAKLTNTTTESRCPTQGEPSLNEEQDKRFVCKHSMVDRGWG
SEQ ID NO: 11

4 Prepare a 3D-model of the sequence, minimize and run long term molecular dynamics simulation (to test *in silico* stability)

5 Synthesize gene, reclone, express protein in *E.coli*

6
a. determine the ability of Virus-con to bind antibodies specific for different wild type proteins
b. Compare its fold to wild type (with CD)
c. Reoptimize the sequence based on results; repeat steps 1-6 as needed.

7
a. demonstrate the ability of the optimized Virus-con to generate a multivalent, neutralizing antibody response in mice
b. Demonstrate ability to protect cultured cells against DENV
c. Preliminary structural characterization with NMR 8 Further optimize to reduce potential reactogenicity: edit to remove areas >6 amino acids identical to any known human or allergenic protein Viable multivalent vacine candidate

FIG. 2

SEQ ID NOS: 40-60

```
DENV600c   MRCVGVGNRDFVEGVSGATWVDVVLEHGGCVTTMAKNKPTLDFELLKTEAKQVATLRKLC 60
DHFc       MRCVGVGNRDFVEGVSGATWVDVVLEHGGCVTTMAKNKPTLDFELLKTEAKQVATLRKLC 60
DENV1c     MRCVGIGSRDFVEGLSGATWVDVVLEHGSCVTTMAKDKPTLDIELLKTEVTNPAVLRKLC 60
DENV3c     MRCVGVGNRDFVEGLSGATWVDVVLEHGGCVTTMAKNKPTLDIELQKTEATQLATLRKLC 60
DENV2c     MRCIGISNRDFVEGVSGGSWVDIVLEHGSCVTTMAKNKPTLDFELIKTEAKQPATLRKYC 60
DENV4c     MRCVGVGNRDFVEGVSGGAWVDLVLEHGGCVTTMAQGKPTLDFELIKTTAKEVALLRTYC 60
           ***:*:..******:**.:***:*****.******:.*****:** **  ..: * **. *

                67             83
DENV600c   IEAKISNITTESRCPTQGEATLNEEQDQQYVCRHSFVDRGWGNGCGLFGKGGLVTCAKFQ 120
DHFc       IEAKISNVTTESRCPTQGEATLKEEQDQQYVCRHSFVDRGWGNGCGLFGKGGLVTCAKFQ 120
DENV1c     IEAKISNTTTDSRCPTQGEATLVEEQDANFVCRRTFVDRGWGNGCGLFGKGSLITCAKFK 120
DENV3c     IEGKITNITTDSRCPTQGEAVLPEEQDQNYVCKHTYVDRGWGNGCGLFGKGSLVTCAKFQ 120
DENV2c     IEAKLTNTTTESRCPTQGEPSLNEEQDKRFVCKHSMVDRGWGNGCGLFGKGGIVTCAMFT 120
DENV4c     IEASISNITTATRCPTQGEPYLKEEQDQQYICRRDVVDRGWGNGCGLFGKGGVVTCAKFS 120
           **..::* ** :*******. * ****  .::*::  ***************.::*** *

                   132
DENV600c   CVTKIEGKVVQYENLEYTVVVTVHSGDQHQVGNETSNHGTTAKITPQAPTTEVQLTDYGT 180
DHFc       CVTKIEGKVVQHENLEYTVVVTVHSGDQHQVGNETSNHGTTAKITPQAPTTEVQLTDYGT 180
DENV1c     CVTKLEGKIVQYENLKYSVIVTVHTGDQHQVGNESTEHGTTATITPQAPTTEIQLTDYGA 180
DENV3c     CLEPIEGKVVQYENLKYTVIITVHTGDQHQVGNET--QGVTAEITPQASTVEAILPEYGT 178
DENV2c     CKKNMEGKVVQPENLEYTIVITPHSGEEHAVGNDTGKHGKEIKITPQSSITEAELTGYGT 180
DENV4c     CSGKITGNLVQIENLEYTVVVTVHNGDTHAVGNDTSNHGVTATITPRSPSVEVKLPDYGE 180
           *    : *::** ***:*::::* *.*: * ***::   :*    ***:.  .*  *. **
```

FIG. 8A

```
DENV600c    LTLECSPRTGLDFNEMVLLQMKNKTWLVHRQWFLDLPLPWTSGASTQQSTWNQKETLVTF 240
DHFc        LSLECSPRTGLDFNEMVLLQMKNKTWLVHRQWFLDLPLPWTSGASTQQSTWNQKETLVTF 240
DENV1c      LTLDCSPRTGLDFNEMVLLTMKEKSWLVHKQWFLDLPLPWTSGASTSQETWNRQDLLVTF 240
DENV3c      LGLECSPRTGLDFNEMILLTMKNKAWMVHRQWFFDLPLPWTSGATTETPTWNRKELLVTF 238
DENV2c      VTMECSPRTGLDFNEMVLLQMEDKAWLVHRQWFLDLPLPWLPGADTQGSNWIQKETLVTF 240
DENV4c      LTLDCEPRSGIDFNEMILMKMKKKTWLVHKQWFLDLPLPWTAGADTSEVHWNYKERMVTF 240
            :  ::*.**:*:*****:*:  *:.*:*:**:***:****** .** *.    *   ::  :***

                                            272
DENV600c    KTAHAKKQEVVVLGSQEGAMHTALTGATEIQNSSGNTIFAGHLKCRLRMDKLQLKGMSYT 300
DHFc        KTAHAKKQEVVVLGSQEGAMHTALTGATEIQTSSGNTIFAGHLKCRLRMDKLQLKGMSYT 300
DENV1c      KTAHAKKQEVVVLGSQEGAMHTALTGATEIQTSGTTTIFAGHLKCRLKMDKLTLKGMSYV 300
DENV3c      KNAHAKKQEVVVLGSQEGAMHTALTGATEIQNSGGTSIFAGHLKCRLKMDKLELKGMSYA 298
DENV2c      KNPHAKKQDVVVLGSQEGAMHTALTGATEIQMSSGNLLFTGHLKCRLRMDKLQLKGMSYS 300
DENV4c      KVPHAKRQDVTVLGSQEGAMHSALAGATEVDSGDGNHMFAGHLKCKVRMEKLRIKGMSYT 300
            * .***:*:*.**********:**:****::   ..  . :*:*****:::*:**  :*****

DENV600c    MCTGKFKIEKEVAETQHGTVVVKVKYEGEDAPCKIPFEIQDLQGKTHNGRLITANPIVTN 360
DHFc        MCTGKFKLEKEVAETQHGTVVVKVKYEGEDAPCKIPFEIQDLQGKTHNGRLITANPIVTN 360
DENV1c      MCTGSFKLEKEVAETQHGTVLVQIKYEGTDAPCKIPFSTQDEKGVTQNGRLITANPIVTD 360
DENV3c      MCTNTFVLKKEVSETQHGTILIKVEYKGEDAPCKIPFSTEDGQGKAHNGRLITANPVVTK 358
DENV2c      MCTGKFKIVKEIAETQHGTIVIRVQYEGDGSPCKIPFEIMDLEKRHVLGRLITVNPIVTE 360
DENV4c      MCSGKFSIDKEMAETQHGTTVVKVKYEGAGAPCKVPIEIRDVNKEKVVGRIISSTPFAEN 360
            **:..* : **::****** :::::*:* .:***:*:.   * :      **:*: .*.. .
```

FIG. 8B

```
                                           390
DENV600c   KDSPVNIEAEPPFGESYIVIGVGDSALKLNWFKKGSSIGKMFETTARGARRMAILGDTAW 420
DHFc       KDSPVNIEAEPPFGESYIVIGVGDSALKLNWFKKGSSIGKMFETTARGARRMAILGDTAW 420
DENV1c     KEKPVNIEAEPPFGESYIVIGAGEKALKLSWFKKGSSIGKMFEATARGARRMAILGDTAW 420
DENV3c     KEEPVNIEAEPPFGESNIVIGIGDKALKINWYKKGSSIGKMFEATARGARRMAILGDTAW 418
DENV2c     KDSPVNIEAEPPFGDSYIIIGVEPGQLKLNWFKKGSSIGQMFETTMRGAKRMAILGDTAW 420
DENV4c     TNSVTNIELEPPFGDSYIVIGVGDSALTLHWFRKGSSIGKMFESTYRGAKRMAILGETAW 420
           .:. .*** *****:* *:**     *.: *::******:***:* ***:******:***

DENV600c   DFGSVGGVFTSLGKAVHQVFGTVYGALFSGVSWMMKIGIGVLLTWIGMNSRSTSMSMSCI 480
DHFc       DFGSVGGVFTSLGKAVHQVFGTVYGALFSGVSWMMKIGIGVLLTWIGMNSRSTSMSMSCI 480
DENV1c     DFGSIGGVFTSVGKLVHQIFGTAYGVLFSGVSWTMKIGIGVLLTWLGLNSRSTSLSMTCI 480
DENV3c     DFGSVGGVLNSLGKMVHQIFGSAYTALFSGVSWIMKIGIGVLLTWIGLNSKNTSMSFSCI 478
DENV2c     DFGSLGGVFTSIGKALHQVFGAIYGAAFSGVSWTMKILIGVIITWIGMNSRSTSLSVSLV 480
DENV4c     DFGSVGGLFTSLGKAVHQVFGSVYTTMFGGVSWMVRILIGFLVLWIGTNSRNTSMAMTCI 480
           ****:**::.*:** :**:**: *  . *.**** ::* **.:: *:* **:.**::.: :

DENV600c   LVGVVTLYLGVMVQA 495
DHFc       LVGVVTLYLGVMVQA 495
DENV1c     AVGLVTLYLGVMVQA 495
DENV3c     VIGIITLYLGAVVQA 493
DENV2c     LVGVVTLYLGVMVQA 495
DENV4c     AVGGITLFLGFTVQA 495
            :* :**:**  ***
```

SEQ ID NOS: 315-320

FIG. 8C

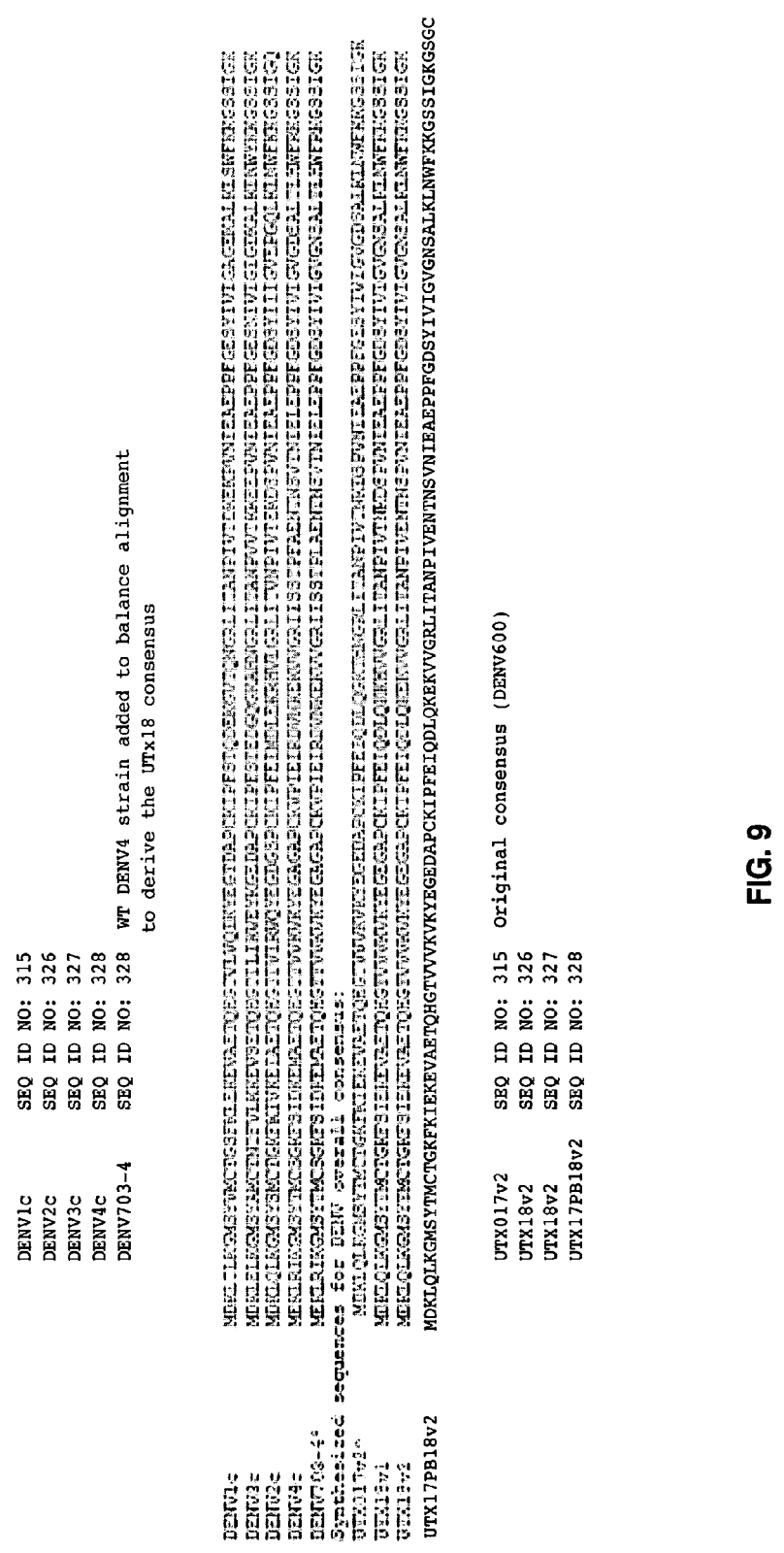

```
DENV1c        SEQ ID NO: 315
DENV2c        SEQ ID NO: 326
DENV3c        SEQ ID NO: 327
DENV4c        SEQ ID NO: 328
DENV703-4     SEQ ID NO: 328  WT DENV4 strain added to balance alignment
                              to derive the UTx18 consensus
```

```
DENV1c        MDKLTLKGMSYVMCTGSFKLEKEVAETQHGTVLVQIKYEGTDAPCKIPFSTQDEKGVTQNGRLITANPIVTDKEKPVNIEAEPPFGESYIVIGAGEKALKLSWFKKGSSIGK
DENV3c        MDKLELKGMSYAMCTNTFVLKKEVSETQHGTILIKVEYKGEDAPCKIPFSTEDGQGKAHNGRLITANPVVTKKEEPVNIEAEPPFGESNIVIGIGDKALKINWYKKGSSIGK
DENV2c        MDKLQLKGMSYSMCTGKFKIVKEIAETQHGTIVIRVQYEGDGSPCKIPFEIMDLEKRHVLGRLITVNPIVTEKDSPVNIEAEPPFGDSYIIIGVEPGQLKLNWFKKGSSIGQ
DENV4c        MEKLRIKGMSYTMCSGKFSIDKEMAETQHGTTVVKVKYEGAGAPCKVPIEIRDVNKEKVVGRIISSTPFAENTNSVTNIELEPPFGDSYIVIGVGDSALTLHWFRKGSSIGK
DENV703-4*    MEKLRIKGMSYTMCSGKFSIDKEMAETQHGTTVVKVKYEGAGAPCKVPIEIRDVNKEKVVGRIISSTPLAENTNSVTNIELEPPFGDSYIVIGVGNSALTLHWFRKGSSIGK
Synthesized sequences for DENV overall consensus:
UTX017v2*      MDKLQLKGMSYTMCTGKFKIEKEVAETQHGTVVVKVKYEGEDAPCKIPFEIQDLQGKTHNGRLITANPIVTNKDSPVNIEAEPPFGESYIVIGVGDSALKLNWFKKGSSIGK
UTX18v1       MDKLQLKGMSYTMCTGKFSIEKEVAETQHGTVVVKVKYEGEGAPCKIPFEIQDLQHKKVVGRLITANPIVTNKDSPVNIEAEPPFGDSYIVIGVGNSALKLNWFKKGSSIGK
UTX18v2       MDKLQLKGMSYTMCTGKFSIEKEVAETQHGTVVVKVKYEGEGAPCKIPFEIQDLQKEKVVGRLITANPIVENTNSPVNIEAEPPFGDSYIVIGVGNSALKLNWFKKGSSIGK
UTX17PB18v2   MDKLQLKGMSYTMCTGKFKIEKEVAETQHGTVVVKVKYEGEDAPCKIPFEIQDLQKEKVVGRLITANPIVENTNSVNIEAEPPFGDSYIVIGVGNSALKLNWFKKGSSIGKGSGC
```

```
UTX017v2      SEQ ID NO: 315  Original consensus (DENV600)
UTX18v2       SEQ ID NO: 326
UTX18v2       SEQ ID NO: 327
UTX17PB18v2   SEQ ID NO: 328
```

FIG. 9

| Virus | Sequence | pI pKa |
|---|---|---|
| PV | GAYTGLPNKKPNVPTIRTAKVQ | 10.46 |
| CVA24 | GAYTGLPNKKPSVPTVRTAKVQ | 10.46 |
| CVB3 | GAYTGIPNQKPKVPTLRQAKVQ | 10.46 |
| HEV71 | GAYSGAPKQVLKKPALRTATVQ | 10.46 |
| cons | GAYTGLPNQKPKVPTIRTAKVQ | 10.46 |

FIG. 13A

PHYSICOCHEMICAL (PCP) BASED CONSENSUS SEQUENCES AND USES THEREOF

CROSS-REFERENCE TO RELATED APPLICATIONS

This international application claims benefit of priority under 35 U.S.C. §119(e) of provisional application U.S. Ser. No. 61/281,555, filed Nov. 18, 2010, the entirety of which is hereby incorporated by reference.

FEDERAL FUNDING LEGEND

This invention was created in part using funds from the federal government under a National Institutes of Health grant AI064913. Consequently, the federal government has certain rights in this invention.

BACKGROUND OF THE INVENTION

1. Field of the Invention

The present invention relates to a method to extract functional information from aligned protein sequences that can identify functional variance even in biased datasets. Major applications include, but are not limited to, design of multivalent vaccines, targets for drug design, novel enzymes, and diagnostic kits for differentiating infectious organisms.

2. Description of the Related Art

The most useful information gleaned from aligned sequences of protein families is first, the absolutely conserved residues, which are usually those that maintain the structure of the protein and its primary functions. The second characteristic is variance. Variance can arise at specific positions in a random fashion, or can represent a true change that may correlate with alteration in phenotype or activity. The problem in dealing with biological datasets, such as sequences for viral or microbial genomes, is that they often have a pronounced bias due to inequivalent distribution. This unequal distribution can arise from non-uniform sampling, for example, there may be many closely related sequences from one epidemic, but only a few from normal infections in a year when the virus had a less lethal phenotype.

Unbiased data reduction methods are needed to make practical use of large volumes of sequence data. To design vaccines, or protein targets for drug design, it may be necessary to analyze both the conservation and the variance in very large numbers of sequences. In practice, this is often done by determining a consensus sequence for reference, that reflects the most commonly occurring amino acid, or type of amino acids, in a given column of an aligned sequence. Conventional methods for calculating consensus sequences cannot account for dataset bias, as they determine the amino acid that occurs most frequently, thus eliminating information on variants at a given position. Even when such averaging is done over a closely related series of sequences, numerical averaging can eliminate important information on the functional importance of substitutions that conserve the physicochemical properties at a position that may be essential for the function or fold of the protein. While some calculation methods for consensus sequences take into account amino acid groupings according to charge, size or hydrophocity, one dimensional averaging method cannot deal with highly variant positions, where the underlying conserved physicochemical properties are less obvious.

There is a recognized need in the art for improved methods to determine where sequence variance can indicate a more severe disease or alter phenotype and functions significantly. Specifically, the prior art is deficient in the lack of unbiased data reduction and computational methods for calculating consensus sequences based on the multidimensional physicochemical properties of amino acids. The method is essential for designing novel proteins that can be used for multivalent subunit vaccines or as targets for drug design. The present invention fulfills this longstanding need and desire in the art.

SUMMARY OF THE INVENTION

The present invention provides methods for designing a consensus protein based on averaging the physicochemical properties (PCP) of amino acids that occur at a given position in related proteins (often referred to as "members of the same protein family"). The method comprises aligning amino acid sequences comprising a conserved domain that is common to all members of the dataset of interest. The aligned sequences in the dataset may reflect substantial bias.

First, subgroups are identified within the dataset that are closely related. Choice of the subgroups can be based on experimental properties, such as serotype groupings, or by using identity matrices (e.g., see FIG. 1) with a cutoff value for groups determined by the overall degree of conservation of the dataset. Sequences can be aligned by a variety of programs within the public domain, including ClustalW or Muscle. Additional information, such as 3-dimensional structures, may also be used to assure the legitimacy of the alignment.

Secondly, once the subgroups have been determined, the individual alignments are then used to calculate a PCP-consensus sequence. In practice, the method converts the original alignment into a matrix of numbers that reflect the physicochemical properties of the amino acids according to values previously determined (1). In this approach, 20 naturally occurring amino acids are represented as points in a five-dimensional space, where the five dimensions roughly correspond to the following: hydrophobicity/hydrophylicity (E1); size (E2); alpha-helix propensity (E3); E4, which is partially related to the partial specific volume, number of codons, and relative abundance of the amino acids; and E5, which correlates weakly with beta-strand propensity.

To obtain PCP consensus sequences, the program selects one amino acid that best approximated the average value of the PCPs at each position of the multiple alignment (2). The average PCP was calculated for each vector p=E1, . . . , E5:

$$\overline{E}^p = \sum_{j=1}^{N} \frac{V_j^p}{N}$$

where N is the number of amino acids in the given column of the alignment and $V_j^p$ are the five quantitative descriptors of the amino acid at that column of the jth sequence. The consensus amino acid ($A_a$) is chosen from those occurring naturally at that position with the least Euclidean distance from the average. These steps may be repeated for each subsequent column of the subgroup alignment. Further, the method can then be repeated for each subgroup alignment, to obtain a set of PCP-consensus proteins that summarize the properties of the whole dataset.

The present invention is directed to a method for designing a consensus protein based on physicochemical properties (PCP) for two or more related proteins. The method comprises aligning amino acid sequences comprising a domain in the related proteins with similar sequences from a plurality of organisms, where the aligned sequences comprise a dataset, which may be highly biased. Subgroup alignments within the alignment of sequences are designated based on a characteristic of the related proteins, and, for a subgroup alignment, which amino acid in a first column of the sequence alignment represents a position in Cartesian multidimensional space defined by scalar values of p physicochemical properties that is closest to the positions of all other amino acids in the column is calculated. The calculating step may be repeated for each subsequent column of the subgroup alignment; where a final sequence of calculated amino acids comprises the PCP-consensus protein for the subgroup.

In a related invention the method further comprises repeating the above-listed steps for each subsequent subgroup thereby obtaining a set of PCP-consensus proteins for the dataset and comparing the PCP-consensus sequences of the subgroup(s) for patterns of conservation and variance.

In another related invention the method further comprises identifying conserved residues and PCP-motifs in the dataset. In another related method the method further comprises identifying variant positions in the PCP-consensus sequence that correlate best with a function via a comparison to PCP-consensus sequences selected based on phenotypes thereof. In yet another related invention the method further comprises preparing a 3-dimensional model to test a predicted fold of the PCP-consensus protein and determining stability thereof via molecular dynamics simulations in silico. In another related invention, the method further comprises synthesizing a nucleic acid that encodes the PCP-consensus protein, constructing an expression vector to express the synthesized nucleic in a host cell and isolating and purifying the conserved protein expressed in the host cell. In yet another related invention the method further comprises removing one or more areas of greater than 6 amino acids identical to known human or allergenic proteins.

The present invention also is directed to a PCP-consensus protein designed by the methods described herein.

The present invention is directed further to a related PCP-consensus protein. The PCP-consensus protein comprises a sequence of amino acids each of which is derived from an alignment of protein domains from a family of related proteins, where the sequence contains one or more motifs common to all of the proteins. A related invention is directed to a viral PCP-consensus protein with a sequence shown in one of SEQ ID NO: 315, SEQ ID NO: 326, SEQ ID NO: 327, or SEQ ID NO: 328. Another related invention is directed to an immunogenic composition comprising the PCP-consensus proteins described herein and one or both of an adjuvant or diluent. Yet another related invention is directed to a pharmaceutical composition comprising the PCP-consensus proteins described herein and a physiologically acceptable carrier.

The present invention is directed further still to a kit. The kit comprises one or more viral PCP-consensus proteins and/or antibodies that detect the one or more PCP-consensus proteins representing proteins characteristic of a pathogen. In a related invention, the kit comprises PCP-consensus proteins of SEQ ID NO: 315, SEQ ID NO: 326, SEQ ID NO: 327, SEQ ID NO: 328, or SEQ ID NO: 333.

The present invention is directed further still to a set of aligned consensus sequences derived from strains of *flavivirus*, comprising SEQ ID NOS: 12-39.

The present invention is directed further still to a method for vaccinating a subject against one or more strains of an infectious organism. The method comprises administering one or more times to the subject an immunologically effective amount of the viral PCP-consensus protein described supra, where the consensus protein is designed to immunopotentiate an immune response against the strain(s) of the infectious organism.

The present invention is directed further still to a method for diagnosing an infectious disease in a subject. The method comprises obtaining a biological sample from the subject and selecting one or more of the PCP-consensus protein(s) described herein specific to one or more strains of an infectious organism causing the disease. The biological sample is contacted with antibodies specific for a PCP-consensus protein(s) and binding of the antibodies indicates presence of an infectious organism that produces a protein that is similar to the PCP-consensus protein(s), thereby indicating the presence of the organism and diagnosing the infectious disease in the subject. In a related invention the method further comprises administering one or more times a pharmacologically effective amount of a PCP-consensus protein or pharmaceutical composition thereof designed to inhibit a protein-protein interaction in the infectious organism, thereby treating the disease.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 2 is an exemplary scheme depicting the design of PCP-consensus proteins for subunit vaccine leads.

FIGS. 3A-3C shows the multiple sequence alignment of 928 *flavivirus* envelope protein sequences simplified to the multiple sequence alignment of 27 consensus sequences. The residues are colored according to their type (hydrophobic, polar, acidic, basic). The boxes highlight the areas mentioned in the text or shown in the figures. The boxes are labeled according to TBE or DENV2. FIG. 3D shows the multiple sequence alignment of 928 *flavivirus* NS3 protease sequences simplified to the multiple sequence alignment of 27 consensus sequences. The residues are colored according to their type (hydrophobic, polar, acidic, basic). FIG. 3E shows—the area around the four cleavage sites (NS2ANS2B, NS2B-NS3, NS3-NS4A, NS4B-NS5) of the NS3 protease, in the mosquito borne DENV2 or tick (TBE) viruses. The multiple sequence alignment of 928 *flavivirus* polyprotein sequences, prepared with Muscle, can be accessed at the Flavitrack website in a Java applet accessible via the world wide web at carnot.utmb.edu/flavitracklalign.php). Sequence identifiers are: FIGS. 3A-3C—AHF (SEQ ID NO:12), DT (SEQ ID NO:13), GGE (SEQ ID NO:14), GGY (SEQ ID NO:15), KFD (SEQ ID NO:16), KSI (SEQ NO:17), LGT (SEQ ID NO:18), LI (SEQ ID NO:19), OMSK (SEQ ID NO:20), POW (SEQ ID NO:21), RF (SEQ ID NO:22), SSE (SEQ ID NO:23), TBE (SEQ ID NO:24), DV1 (SEQ ID NO:25), DV2 (SEQ ID NO:26), DV3 (SEQ ID NO:27), DV4 (SEQ ID NO:28), JBE (SEQ ID NO:29), SLE (SEQ ID NO:30), ILH (SEQ ID NO:31), NTAV (SEQ ID NO:32), ROC (SEQ ID NO:33), WN (SEQ ID NO:34), YF (SEQ ID NO:35), APOI (SEQ ID NO:36), MML (SEQ ID NO:37), MOD (SEQ ID NO:38), and RB (SEQ ID NO:39); FIG. 3D—AHF (SEQ ID NO:40), DT (SEQ ID NO:41), GGE (SEQ ID NO:42), GGY (SEQ ID NO:43), KFD (SEQ ID NO:44), KSI (SEQ ID NO:45), LGT (SEQ ID NO:46), LI (SEQ (SEQ ID NO:51), TBE (SEQ ID NO:52), DV1 (SEQ ID NO:53), DV2 (SEQ ID NO:54), DV3 (SEQ ID NO:55), DV4 (SEQ ID NO:56), JBE (SEQ ID NO:57), SLE (SEQ ID NO:58), WN (SEQ ID NO:59), and YF (SEQ ID NO:60); FIG. 3E—DV2 (ns2a-ns2b) (SEQ ID NO:61), DV2 (ns2b-ns3) (SEQ ID NO:62), DV2 (ns3-ns4a) (SEQ ID NO:63), DV2 (ns4b-ns5) (SEQ ID NO:64), TBE (ns2a-ns2b) (SEQ ID NO:65), TBE (ns2b-ns3) (SEQ ID NO:66), TBE (ns3-ns4a) (SEQ ID NO:67), and TBE (ns4b-ns5) (SEQ ID NO:68).

FIGS. 8A-8B depict determining areas of variability by comparing PCP-consensus sequences for each DENV serotype to one prepared from 600 DENV strains or 8-DHF strains from all 4 types ($DENV_{600}$ and $DENV_{DHF}$). FIGS. 8A-8B show the alignment of the PCP-consensus sequences for each DENV serotype (DENV1-4) with $DENV_{600}$ (also UTX017v2) and $DENV_{DHF}$. Areas of significant difference from the consensus sequences are blocked (aa: 88-96, 156-163, 221-230, 272-277, 338-348, 382-386), the three differences (aa: 83, 132, 272) in the first two consensus sequences, as well as 67 and 390 from other studies, are boxed in red. Note that areas of variation in all 4 subtypes coincide with the areas of group specific insertions illustrated in FIGS. 6A-6F. The amino acids are according to ClustaiW2. small and hydrophobic; acidic; basic; Hydroxyl, Amine and Basic. FIG. 8C is a ribbon diagram of a homology model of the $DENV_{600}$ (UTX017v2) sequence, illustrating the positions of the regions of variability (from FIG. 8A). The sidechains highlight where the serotypes differ maximally in their physicochemical properties. The 156-163 variable region includes a 2 amino acid deletion that is found only in DENV3 strains. The Domain111 (112 amino acids) is circled. FIG. 8A-8C—DENV600c (SEQ ID NO:315), DHFc (SEQ ID NO:316), DENV1c (SEQ ID NO:317), DENV3c (SEQ ID NO:318), DENV2c (SEQ ID NO:319), and DENV4c (SEQ ID NO:320).

FIG. 9 shows the alignment of DENV PCP-consensus sequences for each of the four major DENV types and an overall consensus that could be used for multivalent vaccine design, i.e., to design a protein that should generate immunity against all four DENV types simultaneously. The first lines show PCP-consensus sequences for the individual DENV types 1, 3, 2, 4 (SEQ ID NO:315, SEQ ID NO:326, SEQ ID NO:327, SEQ ID NO:328, respectively and DENV703-4 (SEQ ID NO:328)) and a wild type DENV4 (marked by an *). These and the original EconDom111 PCP-consensus, UTX017v2 (SEQ ID NO:315), derived from them, are colored according to amino acid types, as per Clustalw. This alignment was used to derive two new overall DENV consensus sequences that are more equidistant to all 4 DENV types, UTX18v1(SEQ ID NO:326) and UTX18v2 (SEQ ID NO:327 and UTX17PB18v2 (SEQ ID NO:328)). The DENV4*(wild type) and the 2nd generation consensus sequences are in 10 black, with only positions in red indicating where they differ from the DENV4c and UTX17v1(SEQ ID NO:328).

FIG. 10A shows that the purified, recombinant UTX017v2 protein is as well recognized as the wild type domains by neutralizing antibodies in serotype-specific patient sera (MIAF) for DENV-1 (81%), 2 (77%), and 3 (76%) but not 4 (68%; the numbers indicate the % identity between the UTX017v2 sequence and the PCP-consensus sequences for the 4 individual serotypes). The DENV-2 specific monoclonal antibodies, D2800-10 and GTX77578, recognize epitopes not in UTX017v2, while the DENV-1, -2, -3 cross-reactive epitope recognized by the neutralizing monoclonal, GTX29202, is clearly retained in the PCP-consensus antigen. FIG. 10B shows a 20% PAGE comparison of the purified conEIII with similar wild type DENV-EIII, purified in a similar fashion; 175 ng total protein per lane. UTX017v2 has a calculated molecular mass of 12.3 kD. Figure shows that UTX18v1 and UTX18v2 bind polyclonal antibodies to DENV4 while retaining at least some reactivity with DENV1-3.

FIGS. 13A-13B show *enterovirus*-encoded and PCP-consensus sequences for a viral peptide linked to the genome (VPg) sequence (FIG. 13A) and demonstrate that poliovirus and coxsackie virus polymerases (Pol3D) uridylylate the consensus VPg as well or better than their own encoded VPgs (FIG. 13B). In FIG. 13A positions differing from PV-VPg are underlined. Sequence identifiers are: FIG. 13A-PV (SEQ ID NO:334), CVA24 (SEQ ID NO:330), CVB3 (SEQ ID NO: 331), HEV71 (SEQ ID NO:332), and cons (SEQ ID NO:333).

DETAILED DESCRIPTION OF THE INVENTION

Figure 1:
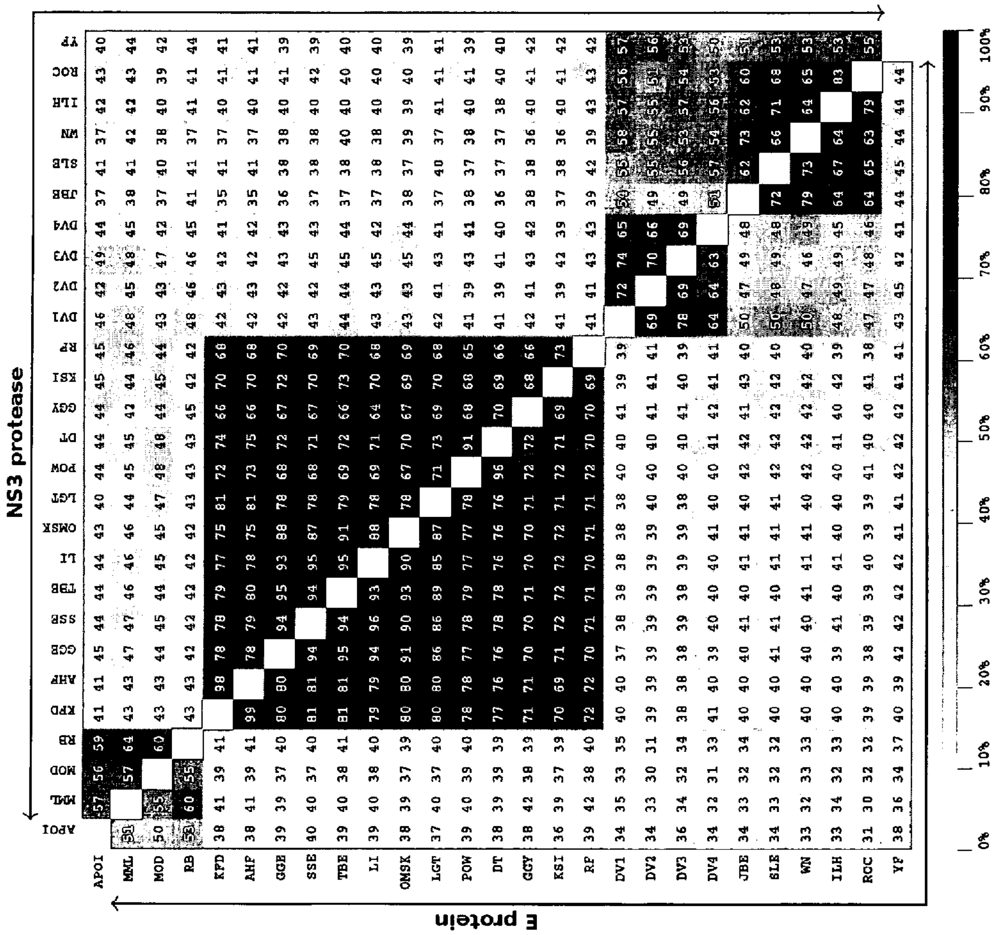
FIG. 1 depicts the interspecies conservation of the NS3 protease (the upper triangular matrix) and the envelope protein (the lower triangular matrix) in terms of sequence identity between PCP-consensus sequences. The tick-borne (KFD-RF), mosquito-borne (DENV1-YF), no-vector (APOI-RB), mosquito-borne encephalitic (JBE-ROC), mosquito-borne hemorrhagic (DENV1-DENV4), and YF form distinct groups of FV. See the Flavitrack website for virus abbreviations (www.carnot.utmb.edu/flavitrack).
Figure 3A:
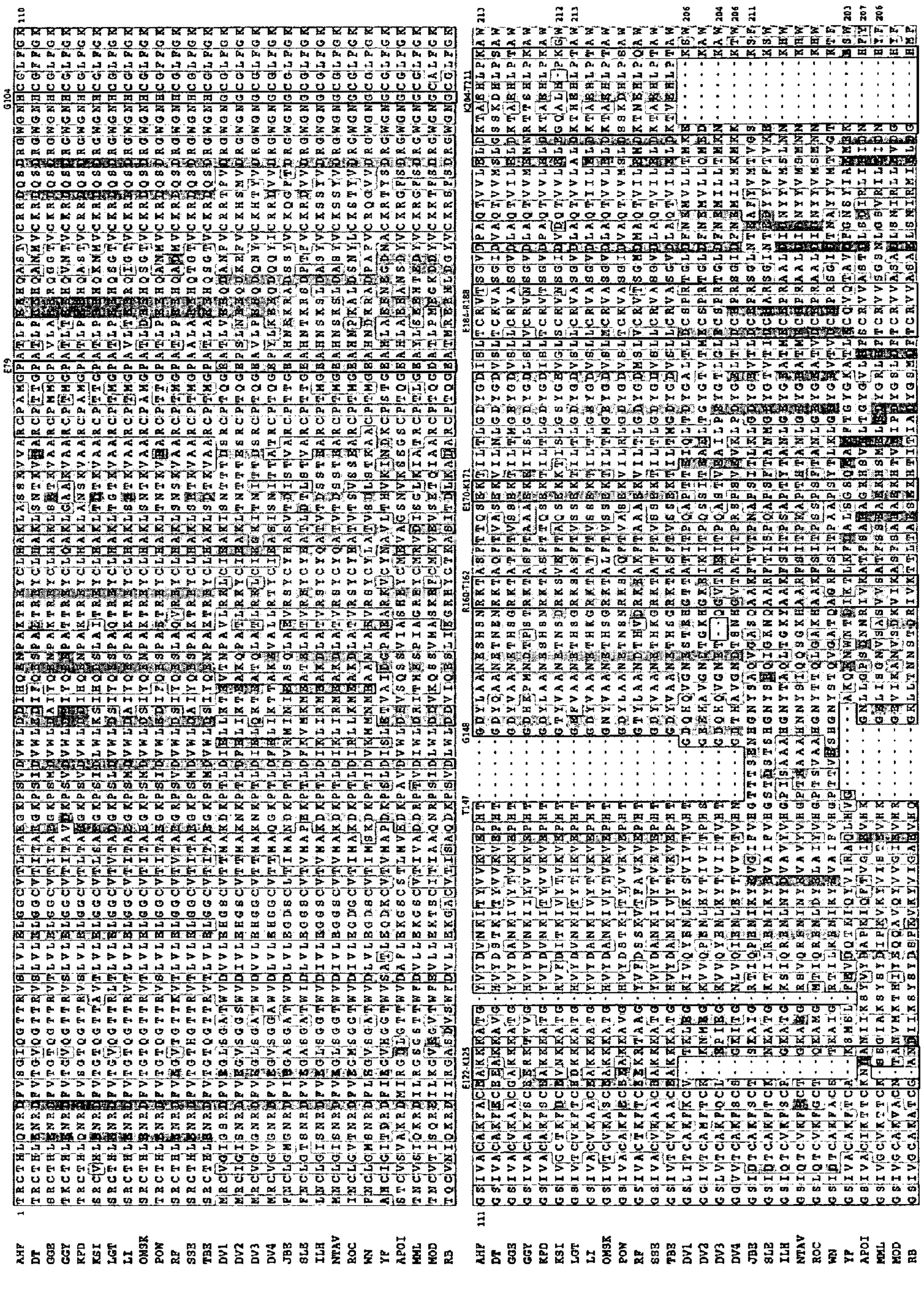
FIG. 3A-3E show sequence alignments of *flavivirus* proteins.
Figure 3B:
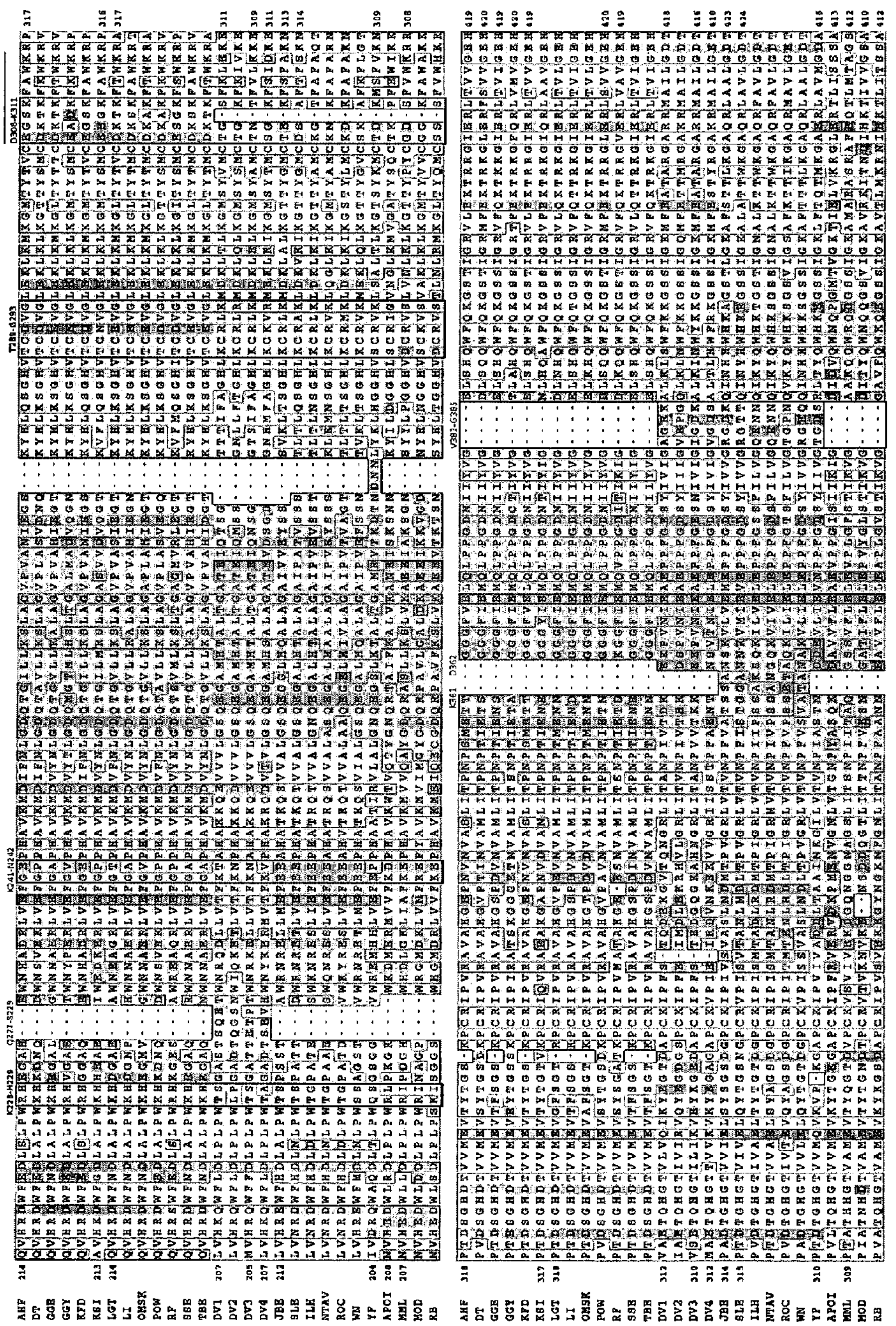
Figure 3C:
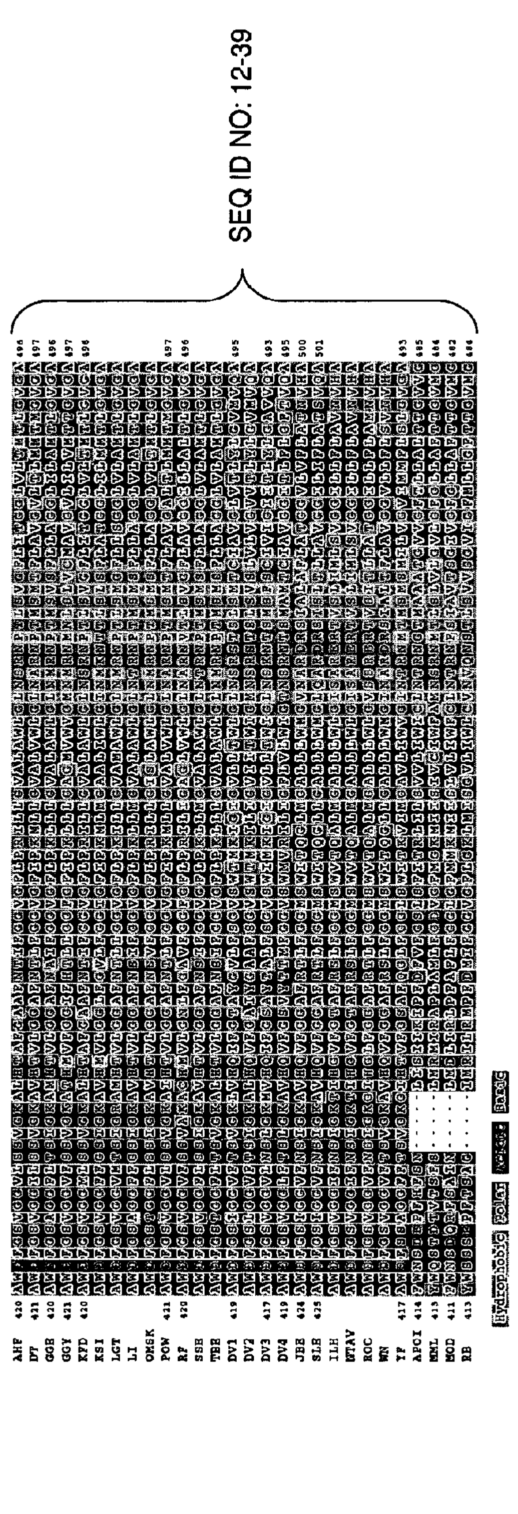
Figure 3E:
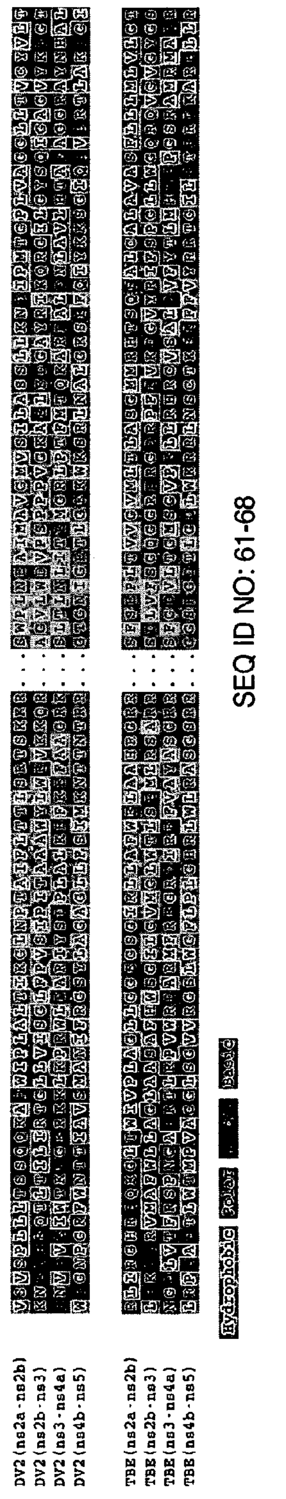
Figure 3D:
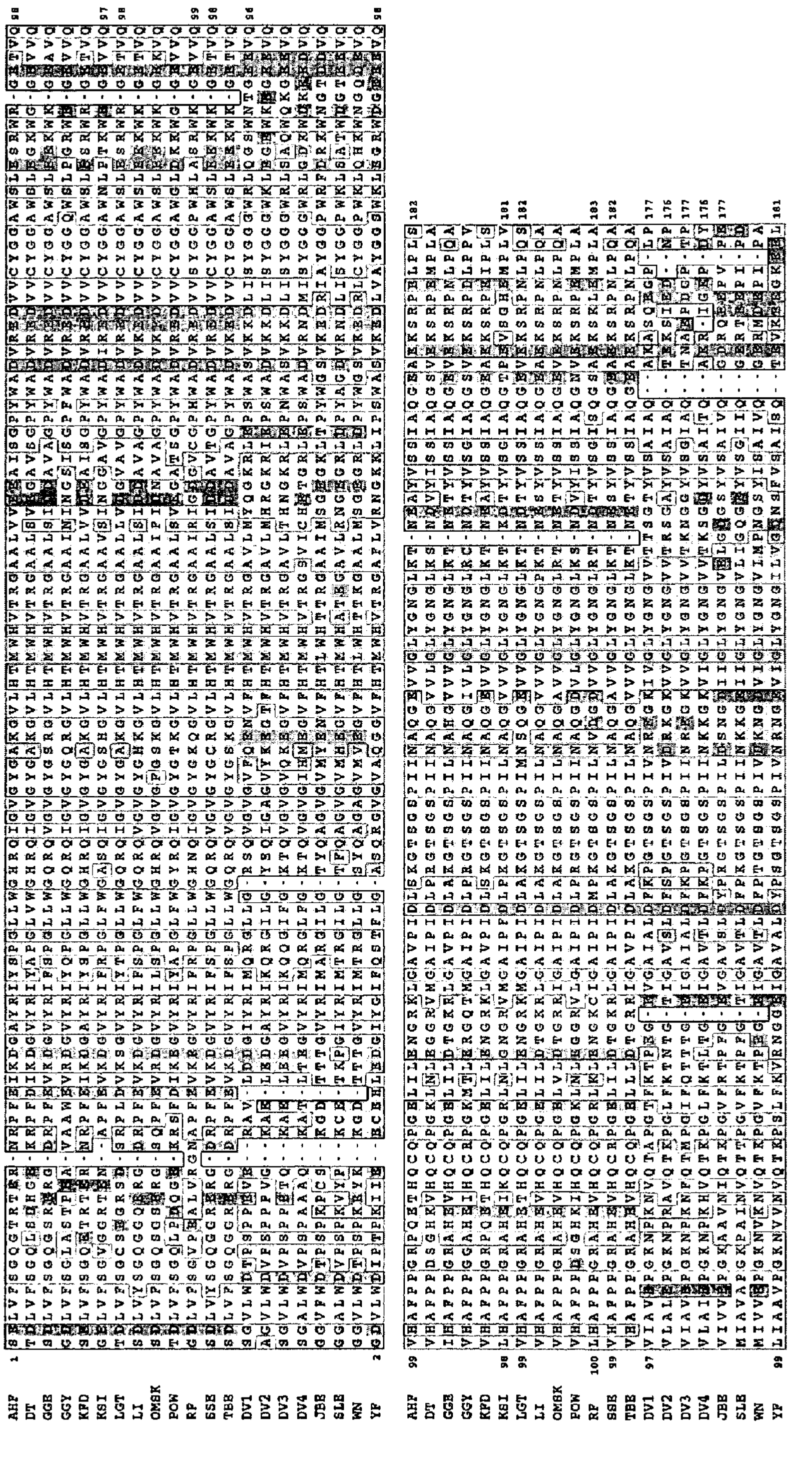

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "subject" refers to any recipient of a PCP-consensus protein or an antibody or drug or therapeutic agent generated or derived therefrom, as an immunogenic or pharmaceutical composition, an inhibitor or vaccine, including as a multivalent vaccine, effective against one or more types or serotypes or groups of infections organisms or pathogens, for example, viruses, bacteria or fungi.

The following abbreviations are used herein. PCP: physicochemical properties, herein an amino acid is defined by 5 numerical values ($E_p$ vectors, where p is one of the physicochemical property vectors derived by multidimensional scaling, as per Venkatarajan and Braun, 2003) that indicate physicochemical properties; E2: envelope protein 2; and MIAF: murine immune ascites fluid; *Alphaviruses* are abbreviated as follows. CHIKV: chikungunya virus; EEEV: Eastern equine encephalitis virus; VEEV: Venezuelan equine encephalitis virus; WEEV Western equine encephalitis virus; MAYV: Mayaro fever virus; and RRV: Ross River Virus. Flaviviruses are abbreviated as follows. DENV: dengue virus; WNV: West Nile Virus and YFV: yellow fever virus. Enteroviruses are abbreviated as. PV: polio virus; CVA: coxsackie virus A; CVB: coxsackie virus B; HEV: human *enterovirus.*

In one embodiment of the present invention there is provided a method for designing a consensus protein based on physicochemical properties (PCP) for two or more related proteins, comprising a) aligning amino acid sequences comprising a domain in the related proteins with similar sequences from a plurality of organisms, where the aligned sequences comprise a dataset; b) designating subgroup alignments within the alignment of sequences based on a characteristic of the related proteins; c) calculating, for a subgroup alignment, which amino acid in a first column of the sequence alignment represents a position in Cartesian multidimensional space defined by scalar values of p physicochemical properties that is closest to the positions of all other amino acids in the column; d) repeating step c) for each subsequent column of the subgroup alignment; wherein a final sequence of calculated amino acids comprises the PCP-consensus protein for the subgroup. In a further embodiment the method comprises repeating steps a) to d) for each subsequent subgroup alignment, thereby obtaining a set of PCP-consensus proteins for the dataset; and comparing the PCP-consensus sequences of the subgroups for patterns of conservation and variance.

In this embodiment the dataset may comprise related sequences from *flavivirus* strains. In a representative example, the dataset may comprise the sequences shown in SEQ ID NOS: 12-39. In an aspect of this embodiment the calculating step a) may comprise determining an average of the p physicochemical properties at each aligned position in the dataset using equation 1; and selecting as a consensus amino acid that amino acid which occurs naturally at a position with the least Euclidean distance from the average with equation 2. In an alternative aspect the dataset is substantially biased and the calculating step may comprise determining an average of the p physicochemical properties for each naturally occurring amino acid in a column in the dataset using equation 1; and selecting as a consensus amino acid that amino acid which is closest in its physicochemical properties to all the naturally occurring amino acids with equation 2.

In a further embodiment the method may comprise identifying one or more conserved residues, insertions, or PCP-motifs in the dataset. In this further embodiment the identifying step may comprise determining a physicochemical distance D for each column in the dataset with equation 3; and determining a similarity value S with equation 4, wherein S is a value from 1 correlating to complete identity in the column to 0 correlating to no identity in the column. In this further embodiment the motifs may comprise the sequences shown in SEQ ID NOS: 69-98. In another further embodiment the method may comprise identifying variant positions in the PCP-consensus sequence that correlate best with a function via a comparison to PCP-consensus sequences selected based on phenotypes thereof. Representative examples of a function are an alteration in enzymatic activity, reactivity, stability, thermosensitivity, or antigenicity.

In another further embodiment the method comprises preparing a 3-dimensional model to test a predicted fold of the PCP-consensus protein; and determining stability thereof via molecular dynamics simulations in silico. In yet another further embodiment the method comprises synthesizing a nucleic acid that encodes the PCP-protein; constructing an expression vector to express the synthesized nucleic acid in a host cell; and isolating and purifying the PCP-consensus protein expressed in the host cell. In yet another further embodiment the method provides removing one or more areas of greater than 6 amino acids identical to known human or allergenic proteins.

In all embodiments p may be five. Also, the physicochemical properties are scaled Eigenvector values that correlate with hydrophobicity/hydrophylicity, size, alpha-helix propensity, a property partially related to the partial specific volume, number of codons and relative abundance of the amino acids; and beta-strand propensity. In addition the organism may comprise an infectious virus, bacteria or other infectious agent. Representative examples of a virus family are *flavivirus, alphavirus* or *enterovirus*. Furthermore, the subgroup designation may be based on phenotype, degree of identity, or other characteristic.

In another embodiment of the present invention there is provided a PCP-consensus protein designed by the method described supra.

In a related embodiment there is provided a PCP-consensus protein, a sequence of amino acids each of which is derived from an alignment of protein domains from a family of related proteins, said sequence containing one or more motifs common to all of the proteins. In this related embodiment the amino acids at each position are selected based an amino acid closest in distance to a point in a 5-dimensional space comprising averages of 5 physicochemical properties for all other amino acids. The physicochemical properties may be as described supra. Also, the proteins comprising the family may be produced by different infectious viruses, infectious bacteria or other infectious organisms. Representative examples of a virus are a *flavivirus*, an *alphavirus* or an *enterovirus*. Particularly, the PCP-consensus proteins comprise one or more motifs with sequences shown in SEQ ID NOS: 69-98. In addition, the protein may have a sequence shown in SEQ ID NO: 315, SEQ ID NO: 326, SEQ ID NO: 327, or SEQ ID NO: 328.

In another related embodiment there is provided a viral PCP-consensus protein with a sequence shown in one of a sequence shown in SEQ ID NO: 315, SEQ ID NO: 326, SEQ ID NO: 327, or SEQ ID NO: 328. In this related embodiment the viral PCP-consensus protein may comprise a motif with a sequence shown in one of SEQ ID NOS: 69-98.

In yet another related embodiment there is provided an immunogenic composition comprising the PCP-consensus protein described supra and one or both of an adjuvant or diluent. In this related embodiment the immunogenic composition may be a vaccine. In yet another related embodiment there is provided a pharmaceutical composition comprising the PCP-consensus protein described supra and a physiologically acceptable carrier. A representative example of a pharmaceutical composition comprises a PCP-consensus protein with a sequence shown in SEQ ID NO: 333. In yet another related embodiment there is provided set of aligned consensus sequences derived from strains of *flavivirus*, comprising SEQ ID NOS: 12-39.

In yet another embodiment of the present invention there is provided a kit comprising one or more of viral PCP-consensus proteins as described supra, one or more antibodies specific for the viral PCP-consensus proteins or a combination thereof. Representative examples of viral PCP-consensus proteins have a sequence shown in SEQ ID NO: 315, SEQ ID NO: 326, SEQ ID NO: 327, SEQ ID NO: 328, or SEQ ID NO: 333.

In yet another embodiment of the present invention there is provided a method for vaccinating a subject against one or more strains of an infectious organism, comprising administering one or more times to the subject an immunologically effective amount of the viral PCP-consensus protein described supra, where the consensus protein is designed to immunopotentiate an immune response against the viral strain(s). In this embodiment, the infectious organism may be a virus, a bacteria or a fungus.

In yet another embodiment of the present invention there is provided a method for diagnosing an infectious disease in a subject, comprising obtaining a biological sample from the subject; selecting one or more of the PCP-consensus protein(s) described supra specific to one or more strains of an infectious organism causing a disease; contacting the biological sample with the PCP-consensus protein(s); and detecting binding of an antibody directed against the infectious organism to the PCP-consensus protein(s) in the biological sample, wherein binding is indicative of the presence of the organism thereby diagnosing the infectious disease in the subject. Further to this embodiment the method may comprise administering one or more times to the subject a pharmacologically effective amount of a PCP-consensus protein or pharmaceutical composition thereof designed to inhibit a protein-protein interaction in the infectious organism, thereby treating the disease.

In both these embodiments the infectious disease may be a viral, a bacterial or a fungal disease. Also, the PCP-consensus proteins are effective to distinguish between diseases exhibiting similar symptoms caused by viruses from different families. Particularly, the PCP-consensus proteins are effective to distinguish between the *flavivirus* Dengue fever *flavivirus* and the Chikungunya or Mayaro *alphavirus*. Also, the biological sample may be blood, serum or a swab comprising cells.

Provided herein is a computational method to calculate and compare physicochemical property (PCP) consensus sequences to account for bias and filter noise due to random amino-acid variations within strains or subtypes. To obtain PCP-consensus sequences, at each position of the multiple alignment, one amino acid is chosen that best approximates the average value of the PCPs (17). This approach is based U.S. Pat. No. 7,424,369, the entirety of which is hereby incorporated by reference. Generally, without being limited, the method is based on relating protein function to sequence motifs that are common to a group of related proteins. Implemented in the software package PCPMer (landau.utmb.edu:8080/WebPCPMer/HomePage/index.html), the first module automatically defines physical-chemical property (PCP) based sequence motifs in aligned sequences of similar proteins. Another module automatically identifies proteins that contain related motifs as potential functional relatives. The search also can be rendered in 3D, by an automatic method to project the motifs onto a known protein structure.

The properties of amino acids are viewed in a multidimensional Cartesian p space, where the 20 naturally occurring amino acids are represented as points therein. The number of dimensions "p" may be any number ranging from 2 to the absolute number of available discrete experimental or derived data for properties. It has been demonstrated previously that 5 Eigenvectors of a multidimensional scaling of over 200 unique property measures are adequate for differentiation of the physicochemical properties of the twenty common amino acids. The five dimensions or the first 5 eigenvectors roughly correspond to hydrophobicity/hydrophylicity (E1); size (E2); alpha-helix propensity (E3); the property E4 which is partially related to the partial specific volume, number of codons and relative abundance of the amino acids; and E5 correlates weakly with beta-strand propensity (1). This 5-dimensional approach to similarity allows one to calculate a true consensus even at very variable positions, as the amino acid selected will reflect the position in 5D space closest in Euclidean space to all the other amino acids in the given column.

The average PCP at each position in the alignment is calculated for each vector p=E1, . . . , E5:

$$\overline{E}^p = \sum_{j=1}^{N} \frac{V_j^p}{N}, \quad \text{Eq. 1}$$

where N is the number of amino acids in the given column of the alignment; and $V_j^p$ are the values for the five quantitative descriptors of the amino acid at that column of the j-th sequence. The consensus amino acid ($A_a$) is chosen from those occurring naturally at that position with the least Euclidean distance from the average:

$$|A_a, \overline{E}| = \sqrt{\sum_{p=E1}^{E5} b_p |V_a^p - \overline{E}^p|^2}. \quad \text{Eq. 2}$$

The scale factors $b_p$ alter the significance of the vectors with higher relative entropies and were calculated as described elsewhere (2). For highly biased datasets, the method can be used in a different mode. Only the amino acids that naturally occur at each position are taken, without regard to their rate of occurrence. In that case, equation 2 can still be used, and the chosen "consensus" amino acid is simply that closest in its physical properties to all the naturally occurring amino acids. The Steps 1-3 in FIG. 1 describe this process.

The method subsequently entails identifying variant positions that correlate best with a function. The function can be, for example, a change in enzymatic activity, or in the ability of the protein to be recognized by an antibody, as applied for example to the differences that correlate with a particular serotype, for example, but not limited to a viral serotype. The consensus approach can simplify vaccine design by highlighting true variance that could influence the properties of viral or bacterial proteins. Variant positions would be obvious by comparing a novel sequence to consensus sequences that represent the common properties of each group.

Conserved residues and PCP-motifs were identified with PCPMer suite (3-5), with modifications as described herein (2). For each column of a multiple sequence alignment a "physicochemical distance" D was determined as $$D = \frac{2}{N(N-1)} \sum_{i<j}^{N} \sqrt{\sum_{p=E1}^{E5} (V_i^p - V_j^p)^2}, \quad \text{Eq. 3}$$

where $V_i^p$, p=E1 . . . E5, are the five quantitative descriptors of i-th amino acid and N is the number of sequences in the multiple alignment. Thus D is the average of all pairs' physicochemical distances. To visualize the 3D-relationships of conserved or variable residues, stereophysicochemical variability plots (SVP) display the physicochemical distances using a color scale for "similarity", defined as $$S = \frac{N_{no\ gaps}}{N} \exp(-0.1\,D), \quad \text{Eq. 4}$$

where $N_{nogaps}$ is the number of sequences not containing a gap in the given column. The similarity is 1 for absolutely conserved (identical) columns and 0 for the most diverse. The definition of similarity also contains a term which lowers its value when gaps are present in the column of the alignment. For the pairwise percentage identity calculations, the length of the shorter consensus sequence is used in the denominator.

Steps 4-8 describe the general procedural steps to obtain a viable multivalent vaccine candidate from the consensus sequence. A 3-dimensional model of the sequence is prepared and minimized and a long term molecular dynamics simulation is run to test stability in silico. A synthetic gene encoding the PCP-consensus protein is produced, recloned into an expression vector and the PCP-consensus protein is expressed in a bacterial host, e.g. *E. coli*. The expressed protein is tested for its ability to bind antibodies specific for different wild type proteins and the consensus protein fold is compared to wild-type via, for example, circular dichroism. The PCP-consensus protein may be optimized, as necessary, based on these results by repeating the previous steps.

The ability of the optimized consensus protein to generate a multivalent, neutralizing antibody response is demonstrated in vivo, such as in a murine model, and the ability of the consensus protein to protect cultured cells against viral infection is demonstrated in vitro. Additionally, NMR data is obtained to characterize the structure of the PCP-consensus protein. At this point, further optimization of the consensus protein may further reduce potential reactogenicity. Also, the consensus sequence may be edited to remove areas of greater than 6 amino acids identical to any known human or allergenic protein to produce a final viable multivalent subunit vaccine candidate.

PCP-consensus sequences may be optimized and redesigned to have minimal reactogenicity and a low estimated potential to stimulate allergic reactions. Particularly, protein design may be modified to better enhance recognition of antigenic sites known to induce a neutralizing response, and to eliminate potential reactive or allergenic sites by removing all sequences >6 amino acids that are found in any human protein or known allergen. The recombinant protein can also be optimized to be soluble, easy to produce, not induce antibodies that would cross-react with mammalian proteins, and have a long shelf life at 20-45° C. for effective use in at least those areas of the world where a viral disease or infection of interest is most prevalent. In addition, expression systems may be optimized for enhanced yield.

I. Design of Multivalent Vaccines

The computational method and PCP-consensus proteins provided herein may be used to design multivalent vaccines. The PCP-consensus method generates a protein that reflects both the conserved physicochemical properties that dictate the common 3D-fold, and optimized antigens in the hypervariable regions to generate multivalent immunogenicity.

For example, Flaviviruses (FV) are important human and animal pathogens (7-12) which typically require insect vectors to infect mammalian hosts (13). Billions of people throughout the world are at risk for DENV (14). While mosquito control can be effective, antiviral agents and wide-spectrum vaccines are being sought to aid in stemming the tide of infections (15-20). To design effective vaccines, which areas of proteins are required for virus function or infectivity must be known, and thus should be targeted by antibodies. Flaviviruses are variable, with many sequence variants found even in single virus isolates from the same patient, i.e. so-called "quasispecies" (21). Within groups of related viruses, a certain amount of variation will occur naturally, due for example to an error-prone polymerase. Recognizing functional variation is important for designing vaccines that will protect against many Flaviviruses simultaneously.

Thus, PCP-consensus sequences may be used to compare the *flavivirus* groups for several reasons. First, trying to view 928 sequences simultaneously emphasizes the need for unbiased data reduction methods. Secondly, consensus sequences should allow better discrimination of residue changes that fall outside the expected group variance. Because there are many more sequences for certain mosquito-borne viruses than for any of the tick-borne or no-known-vector (NKV) groups, variability calculations that included all the natural sequences in Flavitrack would be biased toward species with the largest number of representatives (WNV and DENV). PCP-consensus sequences were created using alignments of all the sequences of each *flavivirus* species (SEQ ID NOS: 12-39).

This is based on the cross-referenced database of annotated FV sequences, Flavitrack. Furthermore, common motif sequences (SEQ ID NO: 40-69) were identified. See Examples 6-7.

The PCP-consensus proteins designed from the *flavivirus* sequence alignments have a sequence effective to generate antibodies to bind both the common and specific surface antigens of, for example, viral proteins or regions or domains thereof in related viruses. Particularly, the virus may be a Dengue fever *flavivirus* (DENV). Examples of consensus proteins of the domain III of the envelope protein of Dengue fever designed to generate antibodies to one or more of types 1-4 of DENV are UTX017v2, UTX18v1, UTX18v2, and UTX17PB18v2.

Generally, the designed PCP-consensus proteins may be recombinant or synthetic proteins. As such, also provided are synthetic nucleic acids or DNAs or genes that encode the consensus proteins. In addition, the present invention provides expression vectors into which the synthetic nucleic acids, DNA or genes may be inserted. It is well known that the expression vector construct comprises the necessary promoters and replication elements necessary to express the synthetic nucleic acid, DNA or gene. Furthermore, the present invention provides a host cell, for example, but not limited to, a bacterial cell, such as *Escherichia coli*, in which to produce the consensus protein. One of ordinary skill in the art is well able to utilize well-known and standard molecular biological or chemical synthetic techniques appropriate to produce the PCP-consensus proteins, the synthetic nucleic acids, DNAs or genes or the expression vectors of the present invention.

The PCP-consensus proteins as vaccine candidates may be used in the preparation of an immunogenic composition suitable to effect an immune response, immunization or vaccination of a subject. The immunogenic composition may comprise a carrier or a suitable adjuvant to boost immune response or a combination thereof, as are known in the art. The immunogenic composition further may comprise a physiologically acceptable diluent or adjuvant known and standard in the art. The immunogenic composition may comprise a vaccine.

Therefore, the present invention provides methods of eliciting an immune response, of immunizing or of vaccinating a subject with the PCP-consensus proteins or immunogenic compositions thereof against an infectious organism or disease. A PCP-consensus protein is designed to contain one or more antigenic regions or epitopes common to one or more types or serotypes of the infectious organism and one or more antigenic regions or epitopes specific to the individual type(s) or serotype(s) thereof. Therefore, a single PCP-consensus protein can be designed as an immuno-potentiating agent to elicit an immune reaction or to generate antibodies against one or more strains, types or serotypes of, for example, an infectious organism, such as a virus, bacteria or fungus.

For example, without being limiting, a single PCP-consensus protein can generate antibodies against the four Dengue virus types. Additionally, the PCP-consensus protein can generate antibodies against one or more viruses comprising a genus or group. Examples of flaviviral diseases are Dengue fever, West Nile and yellow fever. The PCP-consensus protein also may be a consensus bacterial product, for example a toxin domain that is produced by many pathological bacterial or fungal strains.

The pharmaceutical compositions and immunogenic compositions may be administered one or more times to achieve an immunogenic effect. It is well within the skill of an artisan to determine dosage or whether a suitable dosage comprises a single administered dose or multiple administered doses. An appropriate dosage depends on the subject's general health, the route of administration and the formulation used.

II. Drug Design

The PCP-consensus method described herein also can be applied to drug design, for example, that based on designing inhibitors or activators of reactions that are based on protein-protein interactions, such as, but not limited to, enzyme reactions. For example, a PCP-consensus sequence can be designed that represents the conserved properties for all types of an infectious organism, but functions in a multivalent manner. Inhibitors based on this consensus sequence would be multivalent, and would prevent replication or function of the infectious organisms as a group by inhibiting, for example, enzymes involved in RNA or DNA synthesis. See Example 8.

The PCP-consensus proteins, as drug candidates, with a pharmaceutically acceptable carrier may be used in the preparation of a pharmaceutical composition suitable to effect an action that would interfere with a protein-protein interaction in vivo or in vitro, for example, during RNA or DNA synthesis.

III. Diagnostic Agents

The PCP-consensus method can be applied further to designing diagnostic agents effective to discriminate between infectious organisms that may present initially with similar symptoms, but may belong to non-fatal or fatal families. For example, the computational methods described herein may be utilized to determine *alphavirus* consensus sequences which may form the basis for diagnostics and multivalent subunit vaccines, as with *Flaviviruses*. The *alphaviruses* contain three envelope proteins, E1, E2, and E3. E2 has a high degree of surface exposure and contains most of the neutralizing epitopes on the viral surface. A conserved domain within E2 is essential for viral fusion. Examples of alphaviral diseases are Venezuelan equine encephalitis, Chikungunya, eastern equine encephalitis, western equine encephalitis, Mayaro fever, and Ross River.

*Alphaviruses* and *flaviviruses* can cause very similar disease symptoms and may even be mistaken for one another at the clinical level. Identifiers that will rapidly distinguish common *alphaviruses* that are typically not fatal, such as CHIKV and MAYV, from more serious infections with other viruses, such as DENV and VEEV, provide rapid diagnostics that could save considerable time for medics in the field or in an epidemic situation, by enabling efficient triage of cases that would not require hospitalization. A biological sample, for example, but not limited to, blood or serum or a cell swab, may be obtained and tested against the PCP-consensus proteins.

Many of the immune recognition sites in *alphaviruses* are on the E2 protein and, therefore, it is possible that the diagnostics and the vaccine will target similar areas. It is contemplated that multivalent subunit vaccines would be useful to target the more lethal *alphaviruses*, while the diagnostic consensus sequences will target and distinguish the less lethal viruses. The diagnostic consensus sequences are based on the consensus sequences for the families, and should thus generate an antibody response that will recognize all related viruses comprising the non-fatal and the fatal families.

Thus, further provided is a kit comprising one or more of the PCP-consensus proteins described herein and/or or antibodies directed against the same. A kit further may comprise any necessary reagants, buffer, carriers or diluents necessary to utilized the PCP-consensus proteins as diagnostic agents, as is known and standard in the art.

The following examples are given for the purpose of illustrating various embodiments of the invention and are not meant to limit the present invention in any fashion.

Example 1

Materials and Methods

FV Sequences and Structures; Alignment Tools

The Flavitrack database (2,22) contains more than 2600 annotated, complete *flavivirus* genomes, of which 928 natural isolates were used in this study. The E and NS3 sequences were obtained for 10 mosquito-borne, 13 tick-borne and 4 no-known-vector (NKV; sequences of viruses isolated from bats or rodents that have not been found in insects) species; annotated according to CDC abbreviations (www.ncid.cdc.gov/arbocat/browse.asp). Multiple sequence alignments were generated with Clustalw 2.0.3, or MUSCLE, for very large alignments, with default parameters.

Structures for the proteins were from PDB files 1OK8 (the DENV2 envelope protein in the postfusion conformation), 1URZ (the TBE envelope protein in the membrane fusion conformation) and 1BEF (the DENV2 NS3 protease). Models of DENV consensus sequences were prepared using 1OK8 as a template, and our MPACK modeling suite (23-25). The structural alignments and figures were prepared using the PyMol program (26).

Cloning and Antigenicity of PCT-Consensus Proteins

The construct for expression is an untagged "antigen only" protein as previously described (27-28). Consensus proteins are expressed in ER2566 *E. coli* by induction with IPTG, and the protein is purified from the bacterial lysate on a Q sepharose column followed by size exclusion. The purified protein is concentrated in buffer and the CD spectrum analyzed to insure proper folding. Purity is demonstrated with PAGE and Maldi-Mass Spectroscopy. The consensus antigen and wild-type DENV E-III antigens are compared for their reactivity with polyclonal antibodies from sera of patients recovered from DENV infection.

Induction of Pan-DENV Neutralizing Antibody Responses in Mice

Four-six week old Balb/c mice were vaccinated with 2-100 µl doses of the PCP-consensus DENV EdomIII protein 17PB18 (also called 7P8) in 50% Freud's complete adjuvant: group 1 (5 mice) received an injection containing 25 µg on day 1 and 50 µg on day 14; group 2 (6 mice) received 5 µg on day 1 and 10 µg on day 14. Fourteen days after the second dose, all mice are euthanized for terminal bleed via cardiac puncture. The sera collected is tested individually for presence of antibodies against wild-type DENV EIII antigens by ELISA Competitive Inhibition of DENV Infections by Consensus EIII Antigen EIII is the putative receptor binding domain of *flavivirus* envelope proteins and EIII from various DENV types has been shown to compete with virus for binding to target cells (29-30). The ability of wild-type and consensus DENV EIII proteins to compete with homologous and heterologous DENV types for binding to mammalian (Vero) and mosquito (C6/36) cells is assessed. The procedures used are similar to those described elsewhere (29). Briefly, replicate wells in 24 well plates are pre-treated with wild-type or consensus DENV EIII proteins diluted to concentrations of 10, 25 and 50 µg/mL or buffer only for 30 minutes at 4° C., then rinsed with PBS and exposed to DENV strains representing types 1, 2, 3, or 4 at a multiplicity of infection ~1 for 60 minutes at room temperature. After incubation, wells are rinsed to remove residual virus then overlaid with culture medium. After three days, culture supernatants are harvested for virus titration by immunofocus assay on Vero cells. Percent inhibition is determined by comparing virus titers measured from protein treated versus buffer only control wells for each virus.

Fold Comparison of EconDomIII Consensus Proteins with Wild-Type Viral Proteins

An $^{15}$N-labeled protein is prepared by inducing production in *E. coli* growing in medium containing $^{15}$N-ammonia (M9 minimal or a complete $^{15}$N-labeling medium from a commercial source). The purified protein is concentrated and initial spectra indicate whether the folding is similar to the wild type proteins it was designed from. A full structural characterization of the protein provides a structural comparison of the antigenic determinants with wild type DENV domains.

Example 2

Generating Unbiased Sequence Alignments of FV Species and Vector-Specific Groups PCP-consensus sequences were created using alignments of all the sequences of each virus species (FIGS. 3A-3E). Alignments of the resulting PCP-consensus sequences were used to calculate interspecies identities (FIG. 1), insertions and deletions, PCP-motifs and areas of diversity that distinguished the tick- or mosquito-borne species from the NKV-FV. The final set of PCP-consensus sequences may still be somewhat biased, as, for example, several of the tick-borne virus species, such as KFDV/AHFV and DTV/POWV differ from one another by only a few residues. This may lead to overestimating the similarity and underestimating the group variability of the tick-borne FV.

The +-strand RNA genome of a *flavivirus* is translated as a poly protein that is cleaved into three structural (C, prM, and E) and seven nonstructural (NS1, NS2A, NS2B, NS3, NS4A, NS4B, and NS5) proteins. The NS5 polymerase is the most conserved throughout all the FV (78% in tick-borne and 59% in mosquito-borne FV) while the NS2a protein, especially in the C-terminal half, is the most variable (2). The E and NS3 proteases show considerable diversity at the amino acid level, with pairwise sequence identities between tick- and mosquito-borne FV of 37-43% for E and 35-45% for NS3 protease (FIG. 1). However, the colored alignments (FIGS. 3A-3E) show that despite differences at the amino acid level, both proteins maintain a similar pattern of charged, aromatic and aliphatic amino acids, consistent with them all having a 3D-structure similar to that determined for representative sequences for each protein. The alignments were analyzed further to define PCP-based motifs that were common to all FV.

The motifs for E and NS3 proteases correspond to those previously identified using reference sequences for 8 species (31). With a larger number of sequences, plus avoiding the bias arising from different numbers of representatives, the current motifs are generally a few residues shorter. Such areas of high conservation are likely to be involved in maintaining protein stability or function (32).

Table 1 lists sequence motifs in the envelope protein as recognized by the PCPMer program, common to both mosquito- and tick-borne *flaviviruses*. A variable relative entropy cutoff was used, ranging from 0.35 (least significant) to 0.6 (most significant). The residues in bold are surface exposed on the virus particle. The minimum length of a motif was 5, and the largest allowed gap (a continuous stretch of variable residues) in motifs was 2. The numbering corresponds to the sequence DENV2h64THmXxX_U87411.

TABLE 1

| Entropy | Start | Sequence | End | SEQ ID NO: |
|---|---|---|---|---|
| 0.55 | 9 | RDFVEGVSG [1] | 17 | 69 |
| 0.50 | 26 | EHGSCVTTMA | 35 | 70 |
| 0.55 | 54 | A**T**L**R**KYCIEA [2] | 63 | 71 |
| 0.50 | 73 | R**C**P**TQGE**P [3] | 80 | 72 |
| 0.60 | 99 | RGW**GNG**C**GL**F [4] | 108 | 73 |
| 0.40 | 130 | V**QPEN**L**E**YTIVITPH | 144 | 74 |
| 0.35 | 159 | G**KE**I**K**I**T**PQSS [5] | 169 | 75 |
| 0.40 | 190 | GLDFNEMVLLQM | 201 | 76 |
| 0.55 | 206 | WLVHRQWFLD [3,5] | 215 | 77 |
| 0.50 | 239 | TFKNPHA | 245 | 78 |
| 0.45 | 250 | VVVLGSQEG | 258 | 79 |
| 0.50 | 295 | **K**G**MSYSM**C [6-7] | 302 | 80 |
| 0.45 | 312 | IAETQHGTIVIRV**Q**YEG [7-8] | 328 | 81 |
| 0.40 | 332 | **P**CKIP [8] | 336 | 82 |
| 0.40 | 349 | GRLITVNP | 356 | 83 |
| 0.40 | 366 | NIEAEPPFGDSYIIIG [6-9] | 381 | 84 |
| 0.45 | 391 | WFKKGSSIG [7-8,10] | 399 | 85 |
| 0.55 | 416 | GDTAWDFGSLGG | 427 | 86 |
| 0.40 | 431 | SIGKALHQVFGAIY [2] | 444 | 87 |
| 0.45 | 448 | FSGVSW | 453 | 88 |
| 0.40 | 460 | GVIITWIGMNSRS | 472 | 89 |

[1] Part of a cytotoxic T-cell epitope identified for YF (69).
[2] Residues corresponding to 60-68, 431-440 are part of T-cell epitopes in JBE (70).
[3] Residues corresponding to 75, 76, 81, 83, 86, 170, 234 are part of non-neutralizing epitopes in WNV (71).
[4] Mutations at W101, L107, F108 block cross-reactive antibody recognition in DENV (21).
[5] Adjacent to the K204-T211 insertion specific to tick-borne viruses (D203-K204 in DENV2).
[6] Residues 291, 301-307, 381-383 form part of serotype specific epitopes (23).
[7] Residues corresponding to 307, 308, 310-312, 325, 383, 384, 386, 388, 389, 391, 393 neutralizing epitope in DENV3 (72).
[8] Residues 325-331, 335-342, 368-398 in JBE are part of B-cell epitopes (70).
[9] Adjacent to the insertion V382-G385 specific to mosquito-borne viruses.
[10] Residue 390, which immediately precedes this region, is primarily Asn (N) in Asian strains of DENV2, while it is Glu (E) in American strains. Mutants of the Asian virus with E390 replicate more slowly in moncyte-derived macrophages than the wild type with N390 (48).

Table 1 lists motifs in the NS3 protease common to both mosquito- and tick-borne *flaviviruses*. The residues in bold are part of the peptide binding site. The same parameters were used as for the envelope protein. The numbering corresponds to the reference sequence DENV2h64THmXxX_U87411.

TABLE 2

| Entropy | Start | Sequence | End | SEQ ID NO: |
|---|---|---|---|---|
| 0.40 | 2 | GVLWDENVPSP | 10 | 90 |
| 0.40 | 21 | GAYRIKQK | 28 | 91 |
| 0.45 | 32 | GYS**QI**GAG | 39 | 92 |
| 0.50 | 47 | HTMW**HV**TRGA | 56 | 93 |
| 0.50 | 67 | PSWADENVKK**D**LISYGGGW [1] | 83 | 94 |
| 0.50 | 93 | EEVQVLALEPG | 103 | 95 |
| 0.55 | 133 | **G**T**SG**SP [2] | 138 | 96 |
| 0.55 | 148 | GL**YGNG** | 153 | 97 |
| 0.45 | 161 | YV**S**AIAQ | 167 | 98 |

[1] Residues 71-79 are crossreactive cytotoxic T-cell epitope in DENV2, DENV3 (73).
[2] Residues 133-143 are part of T-cell epitope in DENV (53).

Example 3

3D-Analysis of the NS3 Protease Shows Limited Group Specific Variation

Figures 4A, 4B, 4C:
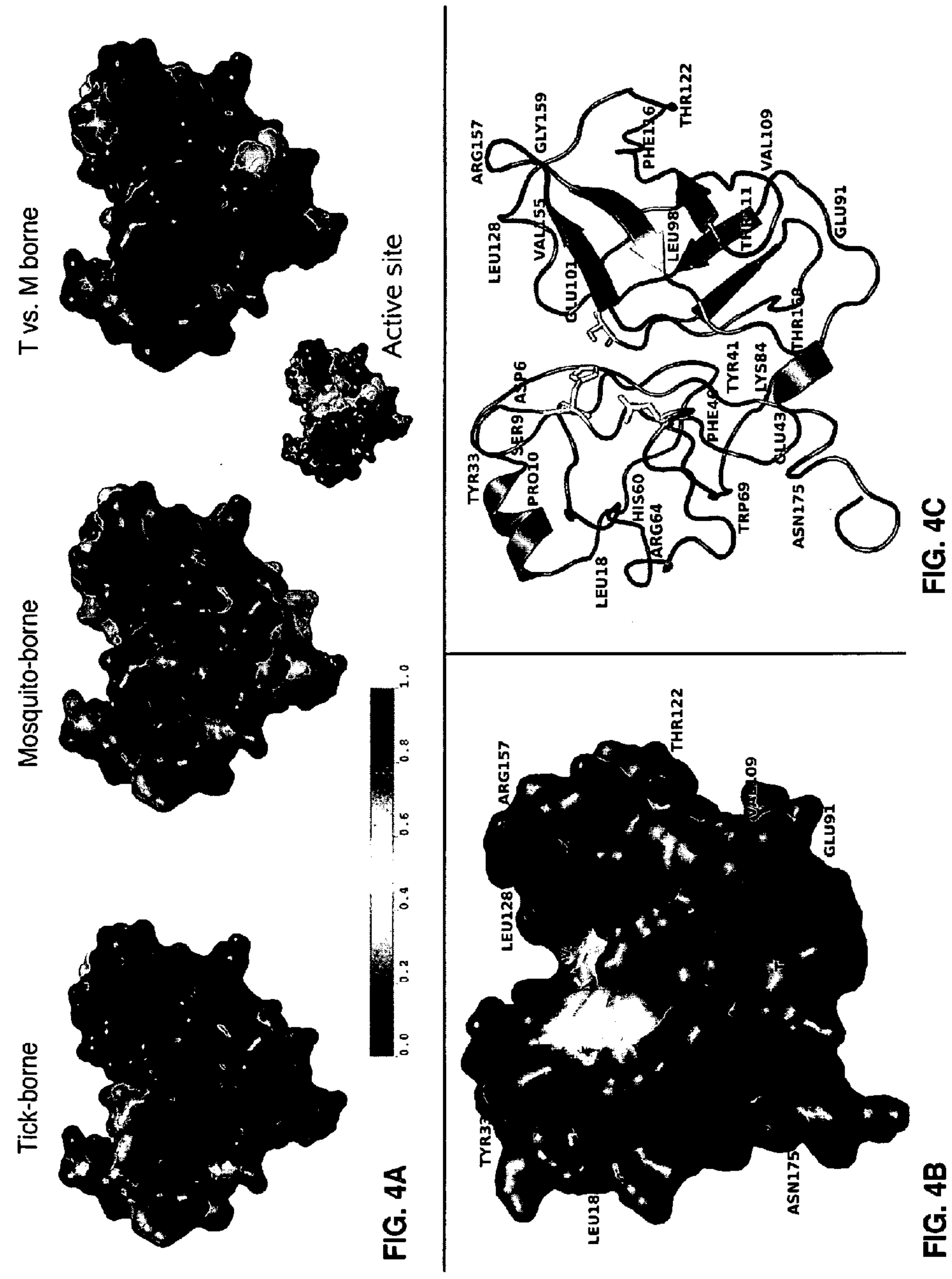
FIGS. 4A-4C: Stereophysicochemical variability plots of the NS3 protease from DENV-2, colored to (FIG. 4A) show conserved (blue) and variable (red) residues within the tick-borne, mosquito-borne, or both (far right). The active site (yellow in the insert) is well conserved in all FV. The NS2B cofactor, required for activity, binds to NS3 from the back in the orientation shown. The residues colored red in FIG. 4B and FIG. 4C are conserved in a different fashion in tick- and mosquito-borne FV.

The N-terminal region of NS3 encodes a trypsin-like serine protease that, together with its cofactor, NS2B, cleaves four sites of the viral polyprotein (NS2A-NS2B, NS2B-NS3, NS3-NS4A, and NS4B-NS5). The cleavage sites are formed by the KR-, RK-, RR- or QR-residues downstream and a small amino acid S, G, or A upstream of the cleavage site (33). The physicochemical properties of the cleavage sites are well conserved in both tick- and mosquito-borne FV (FIG. 4C). As FIGS. 4A-4C show, the active site region of NS3 (near residues Q35, D75, S135) is completely conserved, but is surrounded by more variable residues (FIG. 4C). There are only a few one residue insertions or deletions that distinguish the tick- from mosquito-borne NS3 proteins (at G29, G91, T156, and G179).

Example 4

Insertions in E Distinguish Five Different Groups of FV

In contrast, the alignment of the E protein sequences demarcates eight well defined insertions that distinguish four FV groups (FIGS. 5 and 6A-6F); an additional insertion is found only in YFV. While the motifs common to both tick- and mosquito-borne FV are within the protein core or the surface that faces the viral membrane (surface exposure, from the GETAREA program, is annotated in Table 1), the group specific insertions, primarily residues with charged and polar sidechains, occur primarily in loops on the face of E that is free to interact with the host cell surface during cell entry (FIGS. 6A-6F). With one exception, all insertions are not present in the four No known vector (NKV) viruses, indicating either that they only are required for growth in insect cells, or that their elimination aids in establishing a chronic infection in vertebrates.

The insertions occur in all three domains of E (FIGS. 6A-6F); one insertion (T431-L437), which distinguishes all the arthropod borne from the NKV-viruses, occurs in the stem, not included in the crystal structures. Three (D308-K311, K361-S363, and G381-Q386) are part of a ridge that forms part of a serotype-specific neutralization epitope which is known to contain residues important for receptor binding in vertebrate cells. Two tick specific insertions, E122-K125 and K204-T211, are near one another in domain II (FIG. 4B), near the insertion T226-N230 that is characteristic of mosquito-borne FV causing hemorrhagic disease. This region may contribute to binding to specific insect cells, as it lies near domain III in dimer structures and is probably on the mature virion particle surface. The two insertions that correlate with encephalitic phenotype, T147-G148 and K361-S363, are linked by a salt bridge.

Example 5

Distinguishing Features of YFV-E

Figure 5A:
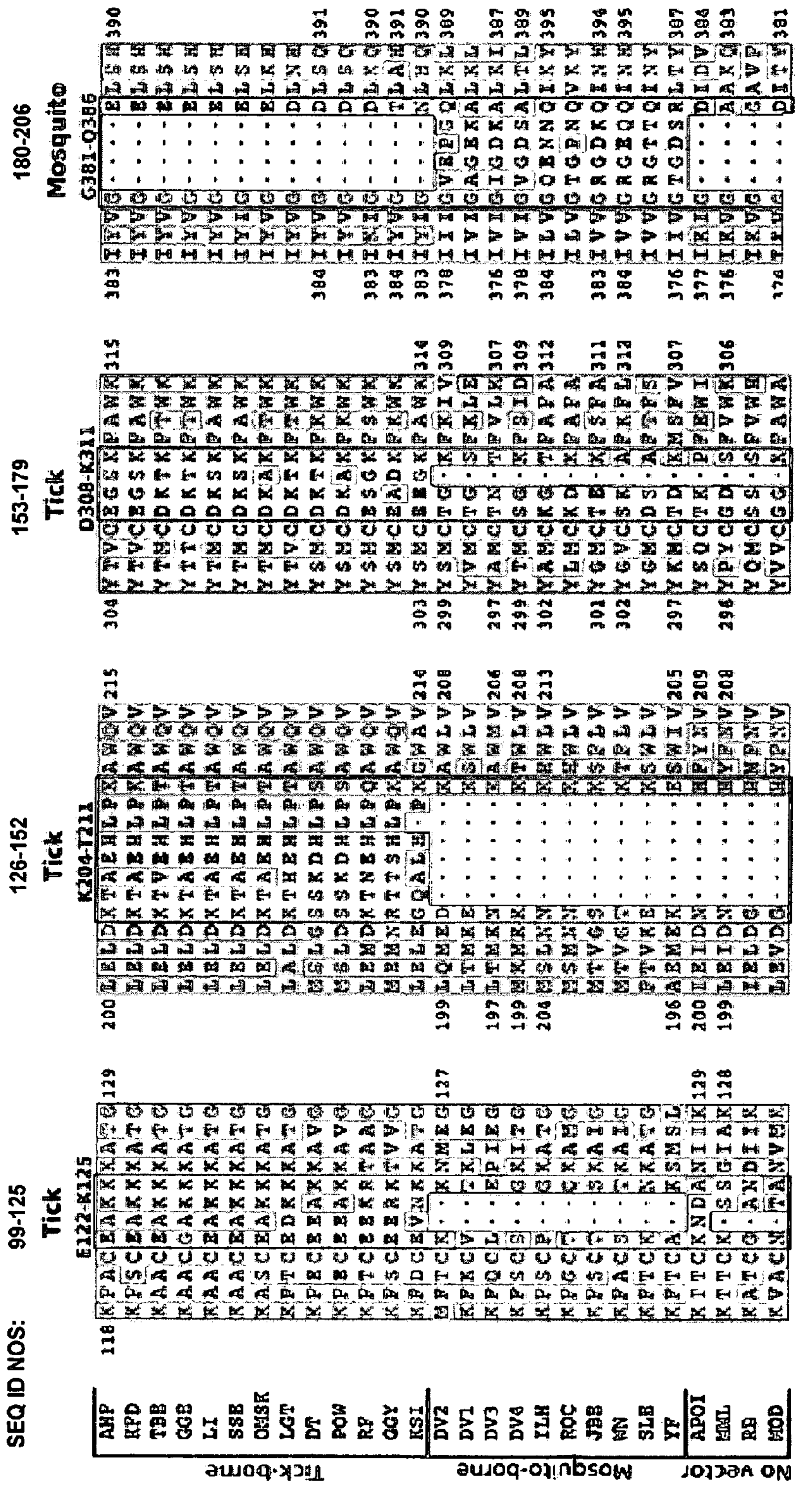
FIG. 5 shows regions of the PCP-consensus sequence alignment, illustrating the insertions that characterize the different groups of FV: tick-borne (AHF-KSI), mosquito-borne (DENV2-YF), No-Known-Vector (NKV; APOI-MOD), mosquito-borne hemorrhagic (DENV2-DENV4), and mosquito-borne encephalitic (ILH-SLE). One insertion in the C-terminus of the protein distinguishes all arthropod borne viruses from the endogenous ones.
Figure 5B:
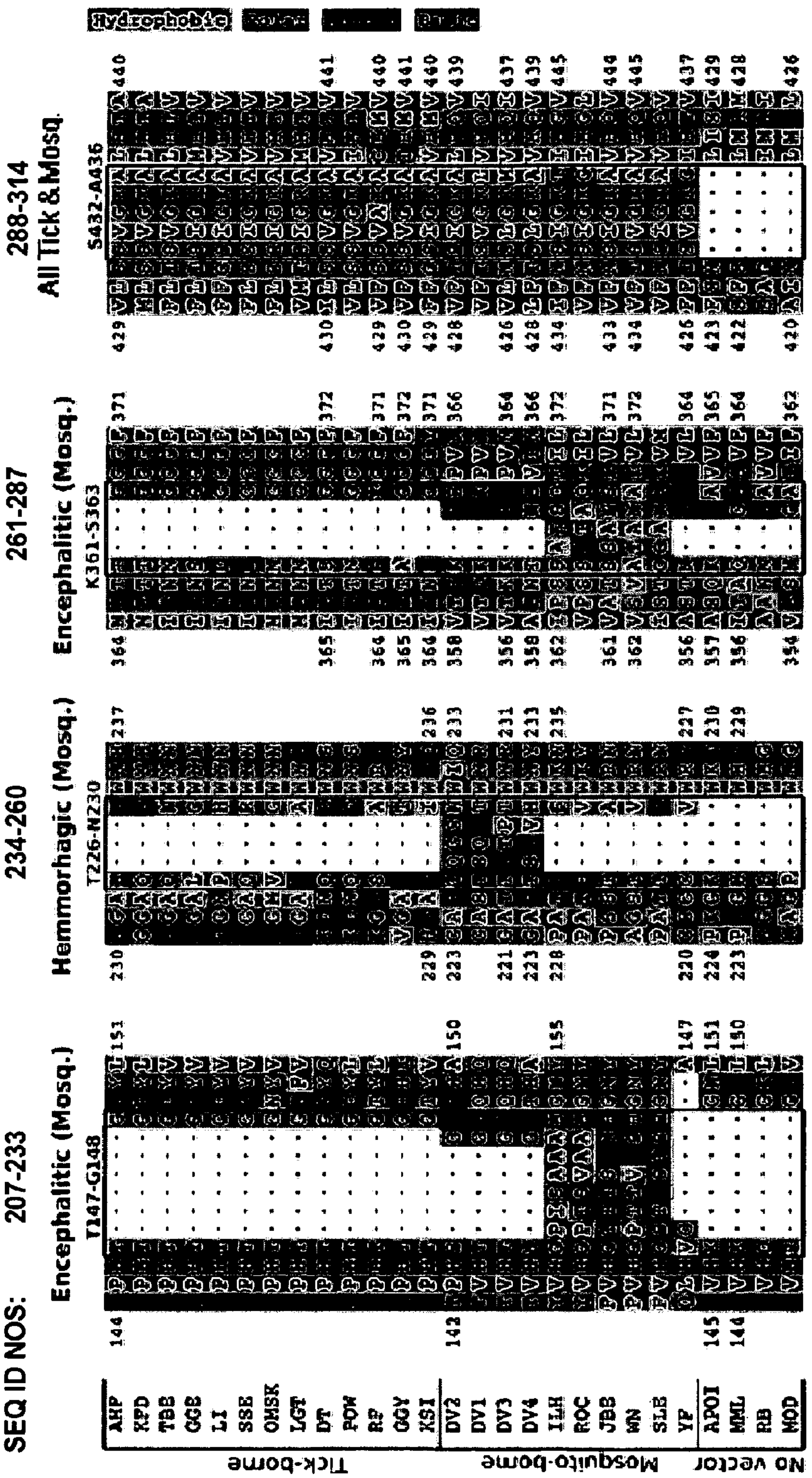
Figures 6A, 6B, 6C, 6D, 6E, 6F:
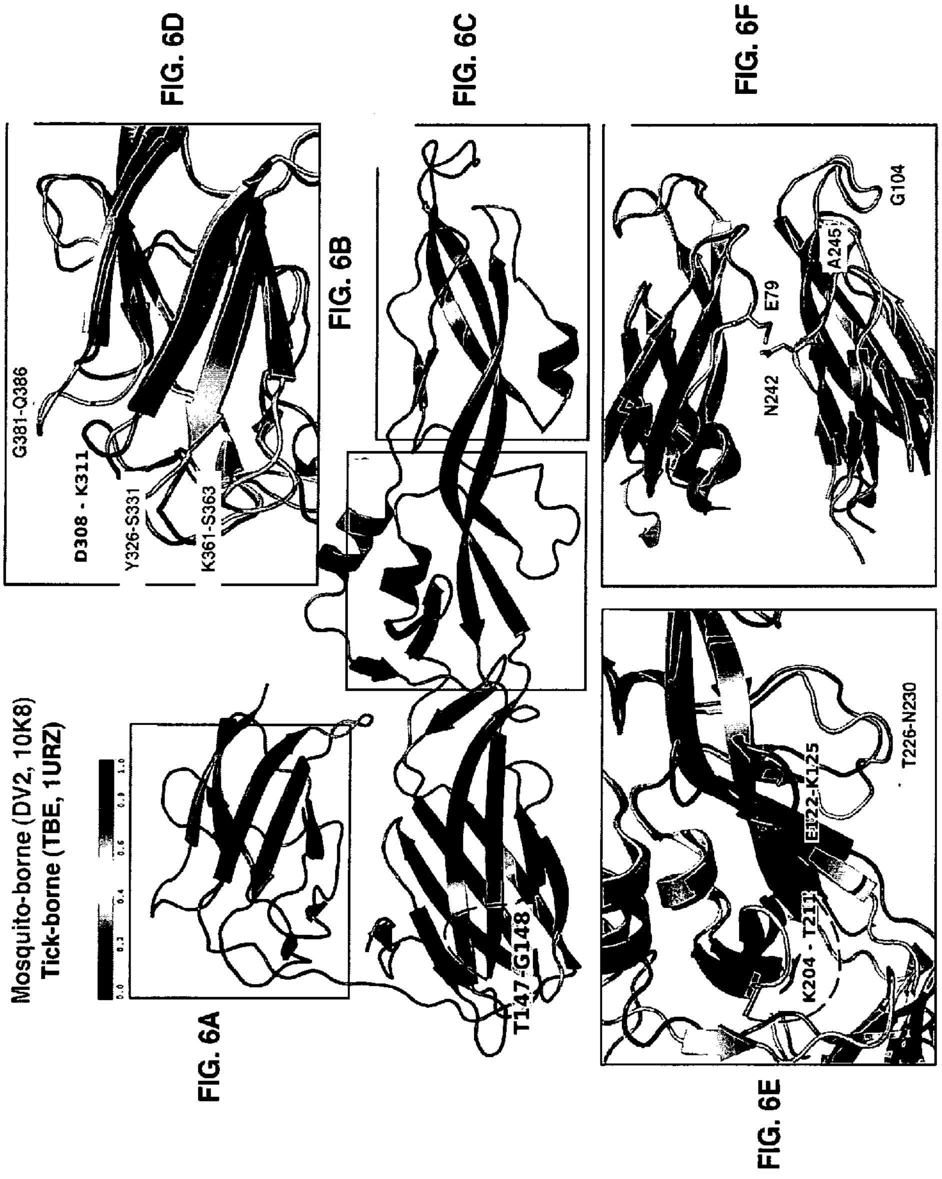
FIGS. 6A-6F are stereophysicochemical variability plots showing the 3D-relationships between variable (red) and conserved (blue) residues of the ectodomain of the E-protein of mosquito-(DENV2 in fusion conformation, 1OK8, yellow) and tick-borne (TBE; 1URZ, gray) viruses (FIGS. 6A-6C). The insertions common to the different FV groups (see FIG. 4) are shown in the expanded FIGS. 6D-6F. Dotted lines indicate the position of insertions that are too flexible to be discerned from the crystal data.
Figure 7:
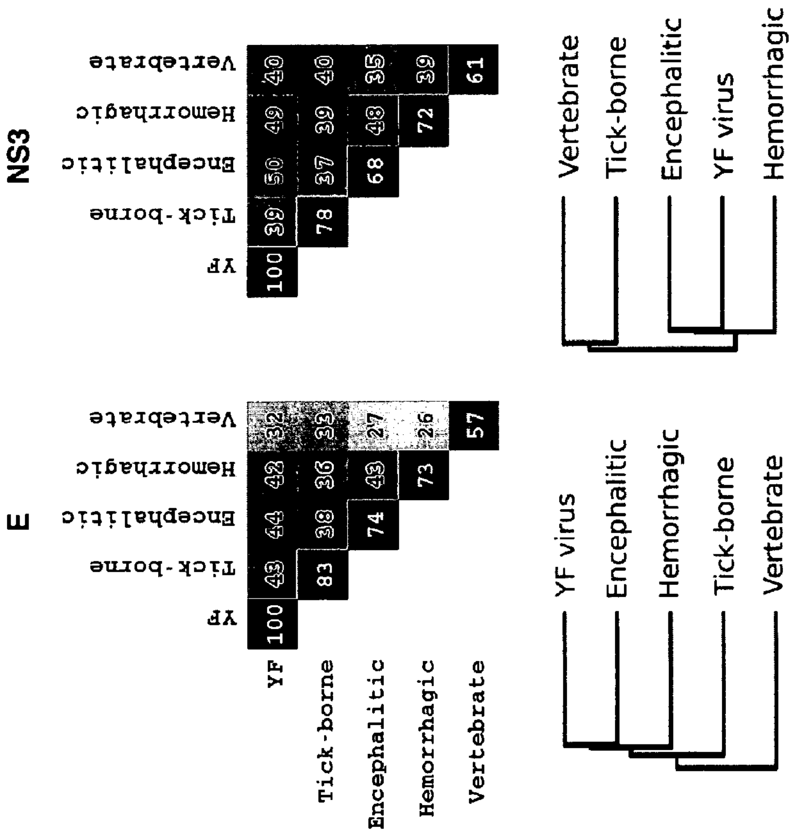
FIG. 7 shows the pairwise distances (normalized to 100; calculated from the number of positions conserved within both groups and similar in physicochemical properties) and phylogenetic trees based on the envelope protein and the NS3 protease illustrate that the "outlier" position ofYF depends on the protein taken as reference. While the E protein is equidistant from all groups, the NS3 protein lies between the encephalitic and hemorrhagic mosquito borne viruses.

Consistent with its mosquito-borne phenotype, YFV contains the G381-Q386 mosquito-specific insertion and lacks all three tick-specific insertions (FIG. 5). However, it also lacks all three insertions that characterize the encephalitic or hemorrhagic phenotypes of mosquito-borne FV. YF can be further distinguished by an extended "deletion" around the T147-G148 loop common to the encephalitic strains, and one strain contains a DNN insertion at position 270. In addition to these, many individual residues of YF differ from all the other FV (~70/493 residues, or 14%), and YF appears to be equidistant from any of the other arthropod-borne viruses (FIG. 7). Among the most striking of these distinguishing residues are a conserved tyrosine (Y326 in DENV2) that may be included in a "tyrosine corner motif"[44] in domain III of the E protein. This tyrosine is conserved as an aromatic residue (Y or F) in all FV, but is M in YF. The Y326 is involved in orbital overlap with F306 (31), a residue that is absolutely conserved in all the FV except YF, where it is V.

Example 6

Highly Variable Regions in DENV Serotypes

Figure 8D:
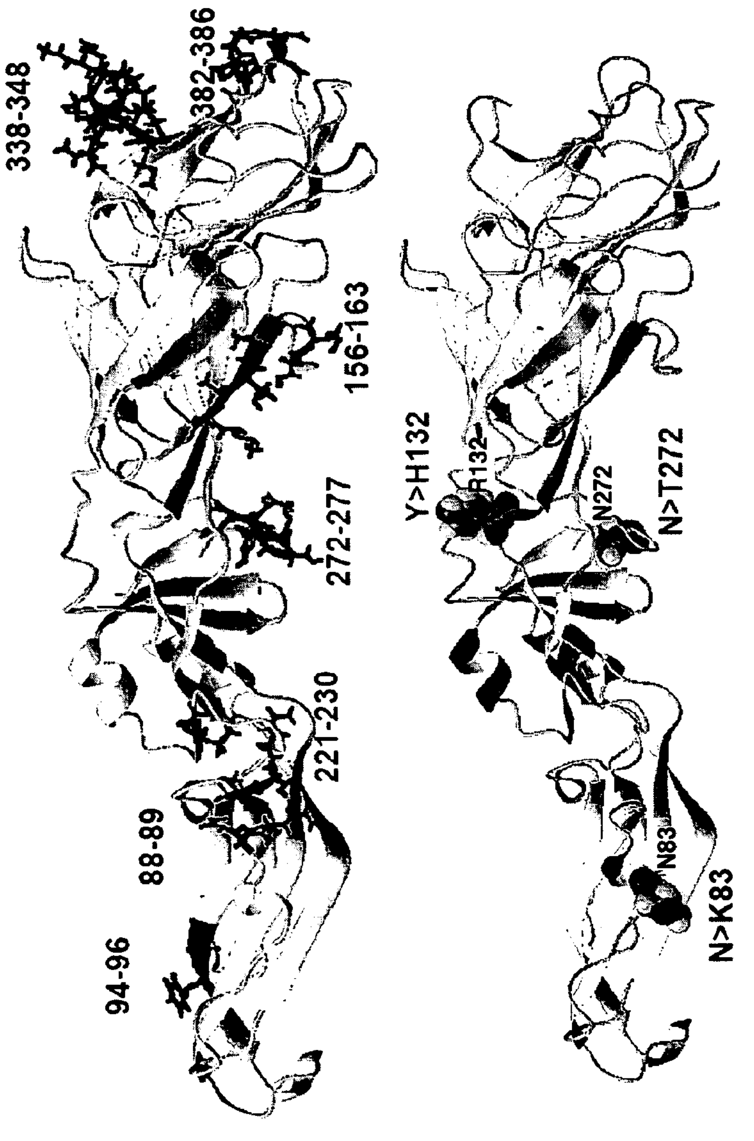
FIG. 8D shows the same model, illustrating only positions that differ enough to change PCPs between the $DENV_{600}$ and $DENV_{DHF}$ consensus sequences. Sequence identifiers are.

One use of PCP-consensus sequences is to distinguish viral areas that represent functional or serotype specific differences, rather than random variability that arises from error-prone RNA synthesis. For example, aligning a PCP-consensus sequence derived from 600 DENV strains ($DENV_{600}$, SEQ ID NO: 315) in Flavitrack with a consensus sequences of DENV serotypes (SEQ ID NOS: 317-320) (FIG. 8A) only showed major differences, i.e., the PCPs of the sequences differed significantly, in discrete areas made up of residues 88-96, 156-163, 221-230, 272-277, 338-348, 382-386, which coincide for the most part with the areas where insertions occur (FIGS. 5 and 6A-6F). Indeed, 3D-mapping of the 6 regions where the consensus sequences from all 4 DENV serotypes vary (black boxes in FIG. 8A) shows that the sequences group to the same 4 areas, in all 3 domains, in the 3D structure of the protein. The variable region between 156 and 163 surrounds a 2 residue deletion that is characteristic of DENV3 strains.

A PCP consensus sequence ($DENV_{DHF}$, SEQ ID NO: 315) was prepared from 8 viruses (2 from each DENV serotype) that were isolated from patients with a severe form of Dengue, Dengue hemorrhagic fever (DHF). Of these, at least two were isolated from patients with a fatal outcome. Comparing the PCP consensus sequences $DENV_{600}$ to $DENV_{DHF}$ showed remarkably little variation (first 2 lines of the alignment in FIGS. 8A-8B) except at three positions, 83, 132 and 272. When the analysis was expanded to include the occurrence of amino acids at these three positions for all the DENV sequences in Flavitrack, little variance was found outside of that expected for the serotype for the DHF strains (Table 3), except that only 32% of the 307 strains of DENV2 had Lysine at residue 83, while 64% of the DHF strains did.

It was noted that residues 132 and 272 map near one another in domain 1 (FIG. 8C-8D), and both are previously described as being near neutralizing epitopes, as determined from the position of escape mutants. Position 67, a reported marker of hemorrhagic disease, was included in the analysis, but found Asn at this position, in all DENV strains, regardless of reported disease severity. Asn was found at position 390 in all DENV except DENV4, where His predominates. The D390 variant, which correlates with milder DENV2 infections and reduced growth in macrophages, is quite rare in the selected sequences. This residue is differentially conserved as a non-charged polar residue in the FV groups: predominantly Asn in DENV1-3, Gln in the Tick-borne and YFV, and His in DENV4 and the encephalitic mosquito borne viruses.

Table 3 shows a comparison of residue choice at positions 67, 83, 132, 272 and 390 according to serotype in 670 DENV strains in Flavitrack and in strains that were designated as isolated from DHF cases (serotype followed by h). The residue in the $DENV_{DHF}$ consensus is highlighted in green, that in the $DENV_{600}$ consensus is showed as blue. All DENV strains had N at position 67, making this meaningless for discrimination of severe phenotype.

TABLE 3

| | To- | 67 | 83 | | | | | | | | 132 | | | | | 272 | | | | 390 | | | |
|---|---|---|---|---|---|---|---|---|---|---|---|---|---|---|---|---|---|---|---|---|---|---|---|
| | tal | N | L | S | A | S | M | N | T | K | V | I | P | Y | H | S | M | N | T | H | D | S | N |
| DENV1 | 215 | 215 | 0 | 0 | 0 | 0 | 3 | 0 | 212 | 0 | 0 | 0 | 1 | 213 | 1 | 0 | 3 | 0 | 212 | 0 | 0 | 214 | 1 |
| DENV2 | 307 | 307 | 0 | 3 | 1 | 0 | 305 | 0 | 2 | 97 | 0 | 0 | 307 | 0 | 0 | 0 | 305 | 0 | 2 | 0 | 5 | 16 | 286 |
| DENV3 | 136 | 136 | 1 | 0 | 0 | 0 | 0 | 98 | 38 | 0 | 0 | 0 | 0 | 83 | 53 | 0 | 0 | 98 | 38 | 0 | 0 | 0 | 136 |
| DENV4 | 12 | 12 | 0 | 0 | 0 | 12 | 0 | 0 | 0 | 12 | 1 | 11 | 0 | 0 | 0 | 12 | 0 | 0 | 0 | 12 | 0 | 0 | 0 |
| Total | 670 | 670 | 1 | 3 | 1 | 12 | 308 | 98 | 252 | 109 | 1 | 11 | 308 | 296 | 54 | 12 | 308 | 98 | 252 | 12 | 5 | 230 | 423 |
| DENV1h | 7 | 7 | 0 | 0 | 0 | 0 | 1 | 0 | 6 | 0 | 0 | 0 | 0 | 7 | 0 | 0 | 1 | 0 | 6 | 0 | 0 | 7 | 0 |
| DENV2h | 25 | 25 | 0 | 0 | 0 | 0 | 24 | 0 | 1 | 16 | 0 | 0 | 25 | 0 | 0 | 0 | 24 | 0 | 1 | 0 | 0 | 0 | 25 |
| DENV3h | 9 | 9 | 0 | 0 | 0 | 0 | 0 | 3 | 6 | 0 | 0 | 0 | 0 | 2 | 7 | 0 | 0 | 3 | 6 | 0 | 0 | 0 | 9 |
| DENV4h | 3 | 3 | 0 | 0 | 0 | 3 | 0 | 0 | 0 | 3 | 0 | 3 | 0 | 0 | 0 | 3 | 0 | 0 | 0 | 3 | 0 | 0 | 0 |
| Total | 44 | 44 | 0 | 0 | 0 | 3 | 25 | 3 | 13 | 19 | 0 | 3 | 25 | 9 | 7 | 3 | 25 | 3 | 13 | 3 | 0 | 7 | 34 |

Example 7

DENV PCP-Consensus Sequences

Three overall DENV consensus sequences were synthesized. UTX017v2 (SEQ ID NO: 315), UTX18v1 (SEQ ID NO: 326) and UTX18v2 (SEQ ID NO: 327) are PCP-consensus proteins for the domain III of the envelope protein (conEIII). UTX017v2, corresponding to $DENV_{600}$ was derived from DENV1c (SEQ ID NO: 321), DENV2c (SEQ ID NO: 322), DENV3c (SEQ ID NO: 323) and DENV4c (SEQ ID NO: 324) consensus sequences. Analysis of this alignment (FIG. 9) showed a bias toward the DENV1 and DENV3 consensus sequences, since they so closely resembled one another (Table 4). To correct for the bias, another, wild type DENV4 sequence, DENV703-4 (SEQ ID NO: 325) which differs at only two positions from the DENV4consensus, was added to produced UTX18v1.

Consensus sequence UTX18v1 was then altered by hand to change residues in the "variable ridge" region of the envelope protein (FIGS. 4A-4C) so that this area would have surface exposed residues equivalent to DENV4c to yield UTX18v2. Both of the resulting consensus sequences were closer to DENV4 in % identity (Table 4), and more equidistant from all four DENV types.

A further overall consensus sequence UTX17PB18v2 (SEQ ID NO: 328) is an optimized version of UTX18v2. UTX17PB18v2 differs from UTX18v2 by restoring the Lys 20 and D43 residues of UTX017v2. It has been shown that the optimized UTX17PB18v2 has the Cys14 disulfide bonded with Cys 45. Mass spectroscopy of UTX17PB18v2 in mice confirms the presence of the disulfide bond and protein fragments consistent with the entire sequence (data not shown).

Identity Matrix with Synthetic PCP-Consensus Genes

Synthetic genes for these PCP-consensus sequences were produced, the genes cloned in expression vectors and expressed in *E. coli*. Table 4 is an identity matrix between the individual PCP-consensus sequences and the synthetic genes. DENV4* is the wild-type strain DENV702-4.

TABLE 4

| | DENV1c | DENV3c | DENV2c | DENV4c | DENV4* | UTX 017v2 | UTX 18v1 | UTX 18v2 |
|---|---|---|---|---|---|---|---|---|
| DENV1c | — | 74.1 | 66.1 | 56.2 | 56.2 | 81.2 | 75.9 | 74.1 |
| DENV3c | 74.1 | — | 62.5 | 51.8 | 50.9 | 75.9 | 70.5 | 67.9 |
| DENV2c | 66.1 | 62.5 | — | 60.7 | 60.7 | 76.8 | 80.4 | 76.8 |
| DENV4c | 56.2 | 61.9 | 60.7 | — | 98.2 | 67.9 | 72.3 | 76.8 |
| DENV4* | 56.2 | 50.9 | 60.7 | 98.2 | — | 67.0 | 73.2 | 77.7 |
| UTX 017v2 | 81.2 | 75.9 | 76.3 | 67.9 | 67.0 | — | 92.9 | 89.3 |
| UTX 18v1 | 75.9 | 70.5 | 80.4 | 72.3 | 73.2 | 92.9 | — | 95.5 |
| UTX 18v2 | 74.1 | 67.9 | 76.8 | 76.8 | 77.7 | 89.3 | 95.5 | — |

Antibody Binding to DENV PCP-Consensus Sequences

Figure 10A:
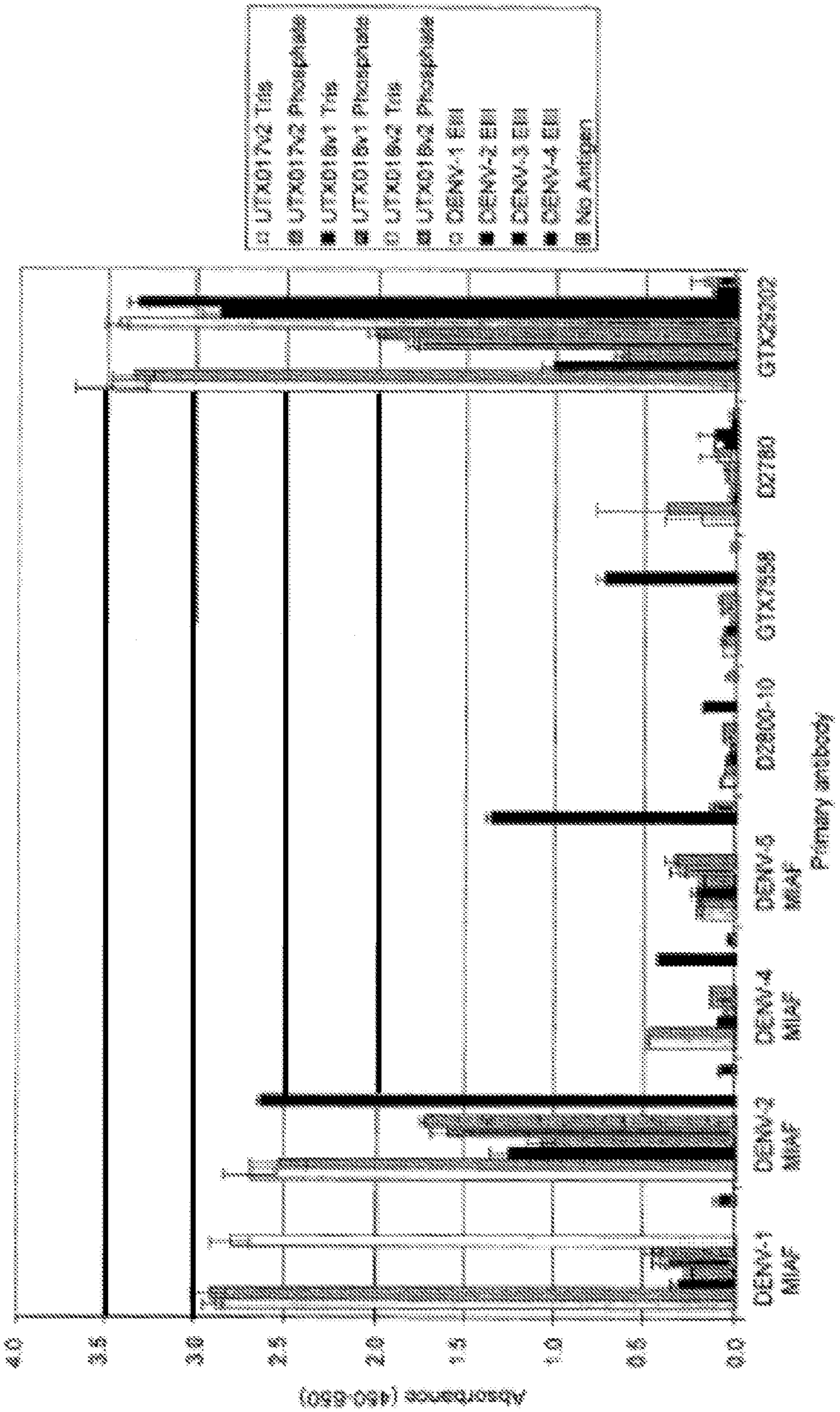
FIGS. 10A-10B shows that PCP-consensus DENV-EIII domain sequences UTX017v2, UTX18v1 and UTX18v2 bind antibodies to DENV serotypes neutralizing antibodies to 3 of the 4 DENV serotypes.
Figure 10B:
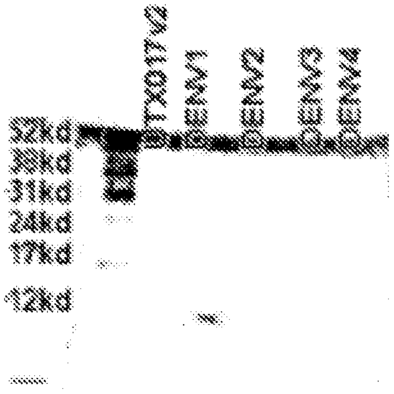

The conEIII protein UTX017v2 was produced in good yield in *E. coli* from a synthetic gene. In a 20% PAGE gel of UTX017v2, DENV1, DENV2, DENV3, and DENV4 with 175 ng total protein per lane, the molecular mass of UTX017v2 was calculated at 12.3 kDa (FIG. 10A). UTX017v2 appears to fold properly and could bind antibodies against Dengue virus (DENV) serotypes 1-3 (FIG. 10B). These results indicated that PCP-consensus proteins can indeed fold like the wild-type proteins they were based on. A tetravalent vaccine of the EconDomIII antigens must demonstrate reactivity with DENV4 as well. UTX18v1 and UTX18v2 bind DENV4 polyclonal antibodies while retaining at least some reactivity with DENV1-3. It is contemplated that recombinants between UTX017v2 and UTX18v2 could restore some of the binding to DENV1 and 3. Only 10 amino acid changes in the 112 amino acid UTX017v2 domain control reactivity to DENV4.

Figure 11A:
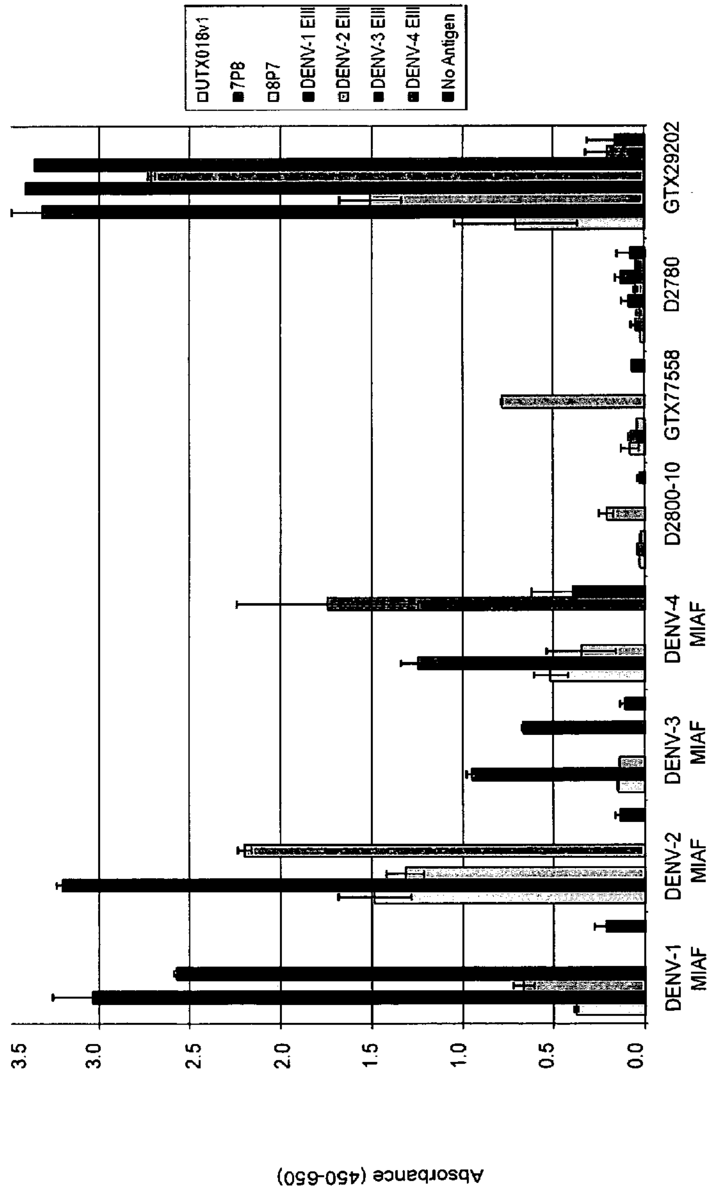
FIGS. 11A-11B show the PCP-consensus DENV-EIII domain protein UTX017PB18 (7P8; for short; maroon bars; 112 amino acids) binding neutralizing antibodies to all 4 DENV serotypes in vitro (FIG. 11A) and Western blots of UTX017PB18 (yellow arrows) demonstrating detection by MIAF antibodies generated to the 4 individual wild type DENV envelope proteins (last lane in each blot, blue arrows) (FIG. 11B).
Figure 11B:
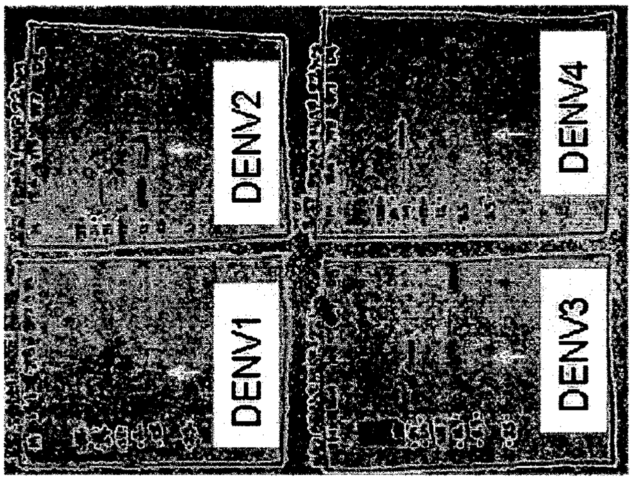

The purified, recombinant UTX017PB18 protein is as well recognized as the wild type domains by type-specific murine sera (MIAF) generated against the 4 individual envelope proteins. The DENV-2 specific monoclonal antibodies, D2800-10 and GTX77578, recognize epitopes not in UTX017PB18, while the cross-reactive epitopes recognized by the neutralizing monoclonal, GTX29202, is clearly retained in our PCP-consensus antigen (FIGS. 11A-11B).

Figure 12:
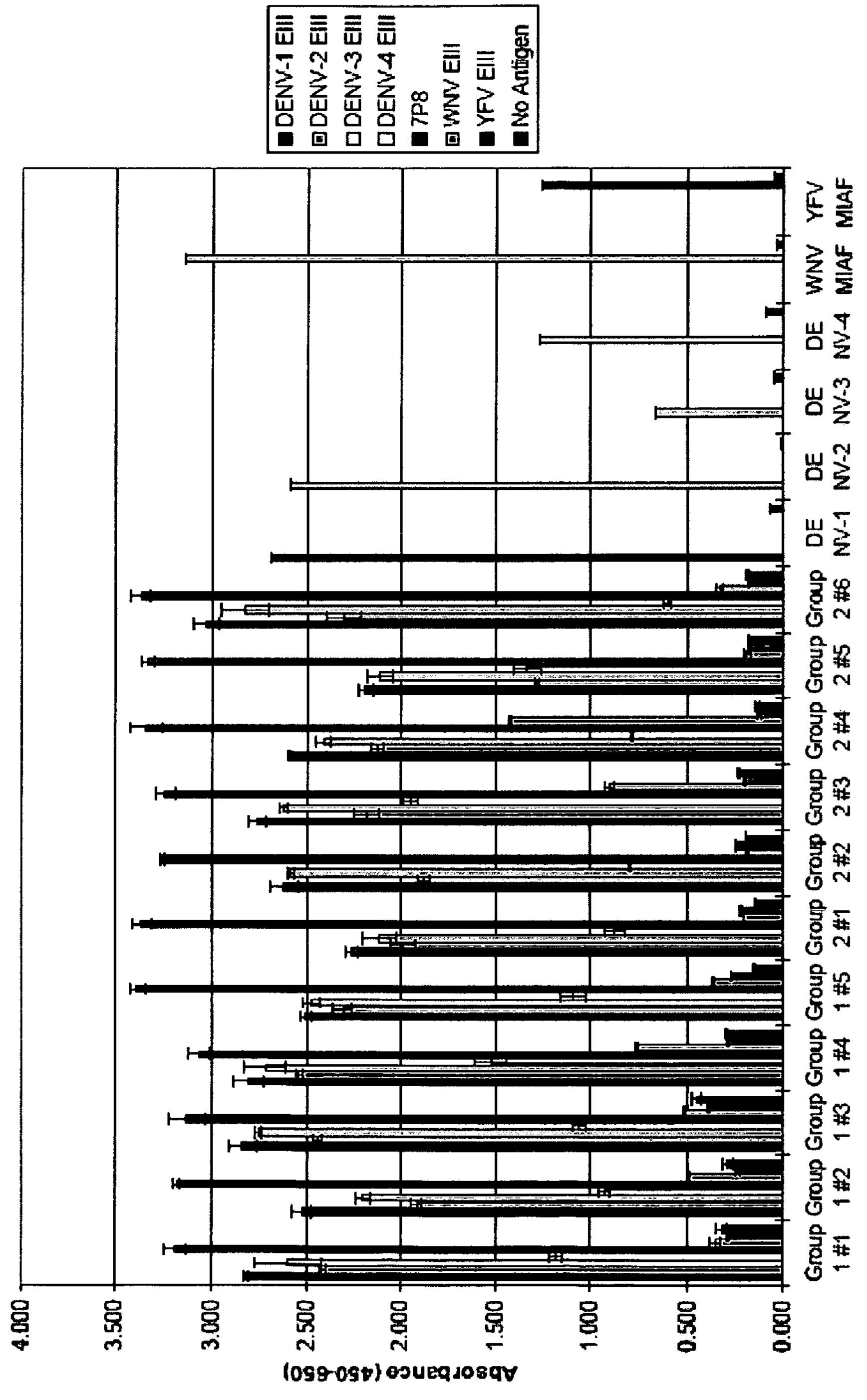
FIG. 12 demonstrates in an ELISA, using sera from mice vaccinated with the PCP-consensus protein, that these contain antibodies that recognize wild type EdomIII from all 4 DENV serotypes and from WNV. Controls (right) are murine immune ascites fluid from mice immunized with a wild type EdomIII protein from DENV 1, 2, 3 or 4, West Nile (WNV) or Yellow fever (YFV) viruses, diluted 1:500. Only the reactivity of these MIAFs with the related immunizing antigen was measured.

Also, mice were vaccinated with the PCP-consensus DENV EdomIII protein UTX017PB18 as described in Example 1. FIG. 12 demonstrates that the vaccinated mice recognize the wild type EdomIII protein from DENV 1, 2, 3 or 4, and West Nile (WNV). It is interesting to note the cross reactivity of the antibodies with the appropriate protein from West Nile virus because WNV is only about 50% identical to UTX017PB18. Yellow fever envelope domain III was also included and no antibodies detected it, which is consistent with its being quite distant from the DENV.

Example 8

Consensus Enteroviral VPq as a Basis for Multivalent Inhibitors of Enteroviral Polymerases The PCP-consensus program was used to design a consensus "viral peptide linked to the genome" (VPg) for the enteroviral group of picornaviruses. To initiate RNA synthesis, *enterovirus* polymerases (3D-pol) uridylylate the 22 amino acid long VPg to form VPgpU. As this reaction is not found in normal cells, it is a target for antiviral drug design.

The sequences of 33 unique enteroviral VPgs were aligned and a PCP consensus protein, VP-cons (SEQ ID NO: 332) was designed from them. FIG. 12A shows that despite the amino acid sequence diversity, i.e., as many as half the residues are different in the HEV-71 VPg compared to that of poliovirus, the pI of the peptides are all the same, and this same pI is found in the consensus VPg and which is not identical to any naturally encoded sequence. The consensus VPg also has the same average pI as that for all the other VPgs in FIG. 13A. The pI is the only really conserved feature of all picornavirus VPgs.

Figure 13B:
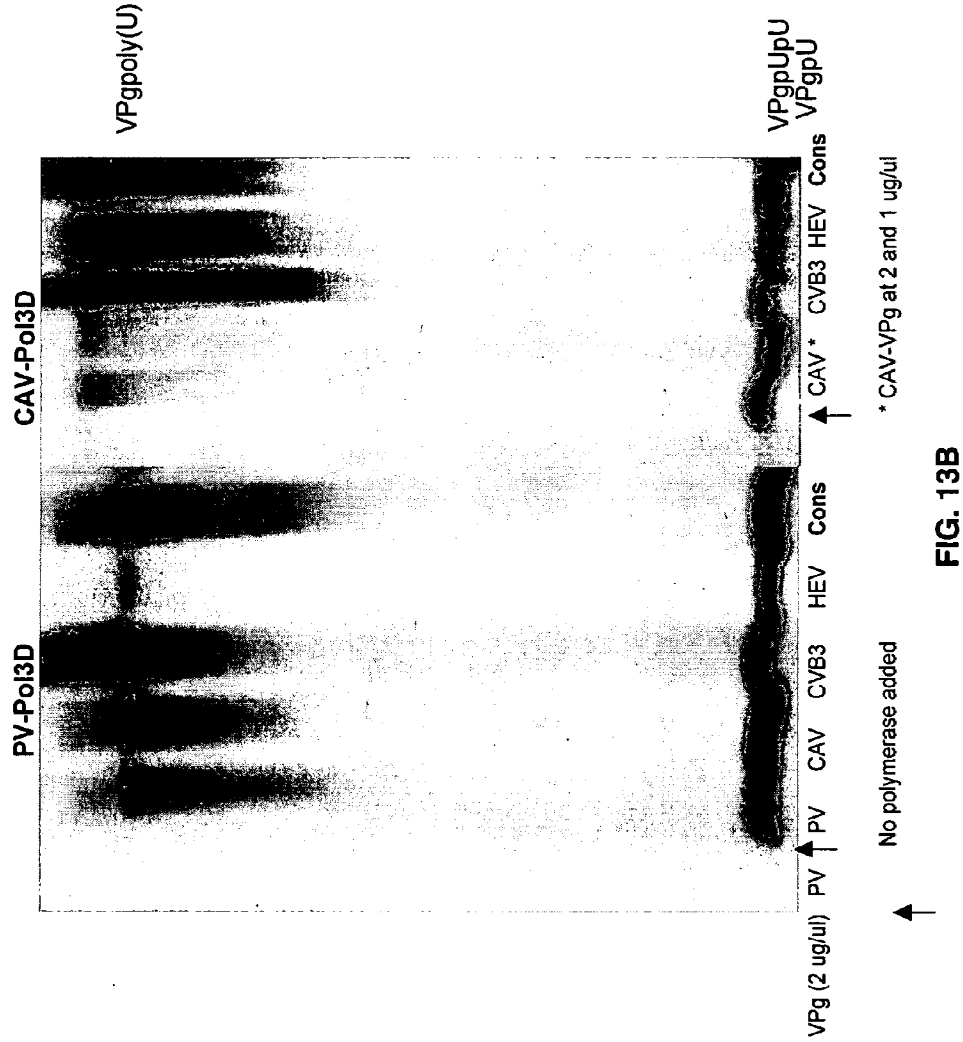

The PCP-consensus (SEQ ID NO: 332) and several diverse VPgs, PV (SEQ ID NO: 328), CVA24 (SEQ ID NO: 329), CVB3 (SEQ ID NO: 330), and HEV71 (SEQ ID NO: 331) were synthesized, and tested for their ability to be uridylylated by two different enteroviral polymerases (Pol3D), that of poliovirus (PV) and of Coxsackie virus A25 (CVA). FIG. 13B demonstrates that both the PV-Pol3D and that of CVA uridylylated the PCP-consensus VPg as well or better than the one encoded in their respective genomes and that VPg-cons is recognized much better by the enzymes than by the VPgs for the more distantly related *enteroviruses*, coxsackie virus B3 and human *enterovirus* 71. Thus the PCP-consensus VPg represents the conserved properties of that for all the enteroviruses, but functions in a multivalent manner. Inhibitors based on this consensus sequence should be multivalent, and should prevent replication of enteroviruses as a group.

The following references are cited herein.

1. Venkatarajan, M. S. & Braun, W. (2001). *Journal of Molecular Modeling* 7, 445-453.
2. Danecek, P. & Schein, C. H. (2009). *Int. J. of Bioinformatics Res. Appl. In press.*
3. Mathura et al. (2003). *Bioinformatics* 19, 1381-1390.
4. Schein et al. (2005). *Proteins-Structure Function and Bioinformatics* 58, 200-210.
5. Schein et al. (2002). *Bmc Bioinformatics* 3.
6. Zell et al. (2008). *Current Opinion in Biotechnology* 19, 652-660.
7. Gaunt, M. W. & Gould, E. A. (2005). *Journal of Virological Methods* 128, 113-127.
8. Thiel et al. (2005). Family Flaviviridae. *Virus Taxonomy, Eight Report of the International Committee for the Taxonomy of Viruses,* 981-998.
9. Gaunt et al. (2001). *J Gen Virol* 82, 1867-1876.
10. Mackenzie et al. (1994). *Archives of Virology* 136, 447-467.
11. Nisbet et al. (2005). *J Gen Virol* 86, 121-124.
12. Gromowski et al. (2008). *J Virol* 82, 8828-37.
13. Monath et al. (2005). *Vaccine* 23, 2956-8.
14. Ishikawa et al. (2008). *Vaccine* 26, 2772-2781.
15. Beasley et al. (2008). *Expert Opinion on Biological Therapy* 8, 95-106.
16. Widman et al. (2008). *Vaccine* 26, 2762-2771.
17. Tang et al. (2008). *American Journal of Tropical Medicine and Hygiene* 78, 999-1001.
18. Barrett, A. D. T. (2008). *Nature Biotechnology* 26, 525-526.
19. Wiggan et al. (2007). *American Journal of Tropical Medicine and Hygiene* 77, 135-135.
20. El Garch et al. (2008). *Veterinary Immunology and Immunopathology* 123, 230-239.
21. Rico-Hesse et al. (1998). *Am J Trop Med Hyg* 58, 96-101.
22. Misra, M. & Schein, C. H. (2007). *Bioinformatics* 23, 2645-2647.
23. Oezguen et al. (2008). *Mol lmmunol* 45, 3740-7.
24. Schein et al. (2001). *Biophysical Journal* 81, 463-472.
25. Soman et al. (2000). *Biophys. J.* 79, 1601-1609.
26. DeLano, W. L. (2002). The PyMOL Molecular Graphics System. *DeLano Scientific*, Palo Alto, Calif., USA.
27. Modis et al. (2005). *J Virol* 79, 1223-31.
28. Oliphant et al. (2007). *J Virol* 81, 11828-39.
29. Stoermer et al. (2008). *Journal of Medicinal Chemistry* 51, 5714-5721.
30. Sukupolvi-Petty et al. (2007). *J Virol* 81, 12816-26.
31. Schein et al. (2005). *Virol J* 2, 40.
32. Kristensen et al. (2008). *Bmc Bioinformatics* 9.
33. Murthy et al. (1999). *J Biol Chem* 274, 5573-80.

One skilled in the art will appreciate readily that the present invention is well adapted to carry out the objects and obtain the ends and advantages mentioned, as well as those objects, ends and advantages inherent herein. The present examples, along with the methods, systems procedures and treatments described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A physicochemical properties (PCP)-consensus protein, comprising:

an isolated polypeptide having the sequence of SEQ ID NO:329, SEQ ID NO:326, SEQ ID NO:327, or SEQ ID NO:328.

2. A physicochemical properties (PCP)-consensus protein comprising isolated polypeptide having the sequence of SEQ ID NO:328.

3. A method for inducing an immune response in a subject against one or more strains of Dengue virus, comprising:

administering an isolated polypeptide of claim 1 to a subject, wherein the subject produces an immune response to Dengue virus.

4. A kit, comprising:

one or more isolated viral physicochemical properties (PCP)-consensus proteins having the sequence of SEQ ID NO:329, SEQ ID NO:326, SEQ ID NO:327, SEQ ID NO:328, or SEQ ID NO:333;

one or more isolated antibodies directed against the viral PCP-consensus proteins; or a combination thereof.

* * * * *

SEQUENCE LISTING

```
<160> NUMBER OF SEQ ID NOS: 334

<210> SEQ ID NO 1
<211> LENGTH: 63
<212> TYPE: PRT
<213> ORGANISM: Flavivirus

<400> SEQUENCE: 1

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Asn Glu Glu Gln
            20                  25                  30

Asp Lys Arg Phe Ile Cys Lys His Ser Met Val Asp Arg Gly Trp Gly
        35                  40                  45

Asn Gly Cys Gly Leu Phe Gly Lys Gly Gly Ile Val Thr Cys Ala
    50                  55                  60


<210> SEQ ID NO 2
<211> LENGTH: 63
<212> TYPE: PRT
<213> ORGANISM: Flavivirus

<400> SEQUENCE: 2

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Asn Glu Glu Gln
            20                  25                  30

Asp Lys Arg Phe Ile Cys Lys His Ser Met Val Asp Arg Gly Trp Gly
        35                  40                  45
```

Asn Gly Cys Gly Leu Phe Gly Lys Gly Gly Ile Val Thr Cys Ala
    50                  55                  60

<210> SEQ ID NO 3
<211> LENGTH: 63
<212> TYPE: PRT
<213> ORGANISM: Flavivirus

<400> SEQUENCE: 3

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Asn Glu Glu Gln
            20                  25                  30

Asp Lys Arg Phe Ile Cys Lys His Ser Met Val Asp Arg Gly Trp Gly
        35                  40                  45

Asn Gly Cys Gly Leu Phe Gly Lys Gly Gly Ile Val Thr Cys Ala
    50                  55                  60

<210> SEQ ID NO 4
<211> LENGTH: 63
<212> TYPE: PRT
<213> ORGANISM: Flavivirus

<400> SEQUENCE: 4

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Asn Glu Glu Gln
            20                  25                  30

Asp Lys Arg Phe Ile Cys Lys His Ser Met Val Asp Arg Gly Trp Gly
        35                  40                  45

Asn Gly Cys Gly Leu Phe Gly Lys Gly Gly Ile Val Thr Cys Ala
    50                  55                  60

<210> SEQ ID NO 5
<211> LENGTH: 63
<212> TYPE: PRT
<213> ORGANISM: Flavivirus

<400> SEQUENCE: 5

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Asn Glu Glu Gln
            20                  25                  30

Asp Lys Arg Phe Ile Cys Lys His Ser Met Val Asp Arg Gly Trp Gly
        35                  40                  45

Asn Gly Cys Gly Leu Phe Gly Lys Gly Gly Ile Val Thr Cys Ala
    50                  55                  60

<210> SEQ ID NO 6
<211> LENGTH: 63
<212> TYPE: PRT
<213> ORGANISM: Flavivirus

<400> SEQUENCE: 6

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Asn Glu Glu Gln
            20                  25                  30

Asp Lys Arg Phe Ile Cys Lys His Ser Met Val Asp Arg Gly Trp Gly
        35                  40                  45

Asn Gly Cys Gly Leu Phe Gly Lys Gly Gly Ile Val Thr Cys Ala
    50                  55                  60

<210> SEQ ID NO 7
<211> LENGTH: 63
<212> TYPE: PRT
<213> ORGANISM: Flavivirus

<400> SEQUENCE: 7

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Asn Glu Glu Gln
            20                  25                  30

Asp Lys Arg Phe Val Cys Lys His Ser Met Val Asp Arg Gly Trp Gly
        35                  40                  45

Asn Gly Cys Gly Leu Phe Gly Lys Gly Gly Ile Val Thr Cys Ala
    50                  55                  60

<210> SEQ ID NO 8
<211> LENGTH: 63
<212> TYPE: PRT
<213> ORGANISM: Flavivirus

<400> SEQUENCE: 8

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Lys Glu Glu Gln
            20                  25                  30

Asp Lys Arg Phe Val Cys Lys His Ser Ile Val Asp Arg Gly Trp Gly
        35                  40                  45

Asn Gly Cys Gly Leu Phe Gly Lys Gly Gly Ile Val Thr Cys Ala
    50                  55                  60

<210> SEQ ID NO 9
<211> LENGTH: 63
<212> TYPE: PRT
<213> ORGANISM: Flavivirus

<400> SEQUENCE: 9

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Lys Glu Glu Gln
            20                  25                  30

Asp Lys Arg Phe Val Cys Lys His Ser Met Val Asp Arg Gly Trp Gly
        35                  40                  45

Asn Gly Cys Gly Leu Phe Gly Lys Gly Gly Ile Val Thr Cys Ala
    50                  55                  60

<210> SEQ ID NO 10
<211> LENGTH: 63
<212> TYPE: PRT
<213> ORGANISM: Flavivirus

<400> SEQUENCE: 10

Thr Leu Arg Lys Tyr Cys Ile Glu Ala Lys Leu Thr Asn Thr Thr Thr
1               5                   10                  15

Glu Ser Arg Cys Pro Thr Gln Gly Glu Pro Ser Leu Lys Glu Glu Gln
            20                  25                  30

Asp Lys Arg Phe Val Cys Lys His Ser Met Val Asp Arg Gly Trp Gly 35 40 45

Asn Gly Cys Gly Leu Phe Gly Lys Gly Gly Ile Val Thr Cys Ala
50 55 60

<210> SEQ ID NO 11
<211> LENGTH: 63
<212> TYPE: PRT
<213> ORGANISM: Flavivirus

<400> SEQUENCE: 11

Thr Leu Arg Lys Tyr Cys Ile Glu Ala Lys Leu Thr Asn Thr Thr Thr
1 5 10 15

Glu Ser Phe Cys Pro Thr Gln Gly Glu Pro Ser Leu Asn Glu Glu Gln
20 25 30

Asp Lys Phe Phe Ile Cys Lys His Ser Met Val Asp Phe Gly Trp Gly
35 40 45

Asn Gly Cys Gly Leu Phe Gly Lys Gly Gly Ile Val Thr Cys Ala
50 55 60

<210> SEQ ID NO 12
<211> LENGTH: 496
<212> TYPE: PRT
<213> ORGANISM: Flavivirus

<400> SEQUENCE: 12

Thr Arg Cys Thr His Leu Gln Asn Arg Asp Phe Val Ser Gly Ile Gln
1 5 10 15

Gly Thr Thr Arg Val Ser Leu Val Leu Glu Leu Gly Gly Cys Val Thr
20 25 30

Leu Thr Ala Glu Gly Lys Pro Ser Val Asp Val Trp Leu Asp Asp Ile
35 40 45

His Gln Glu Asn Pro Ala Lys Thr Arg Glu Tyr Cys Leu His Ala Lys
50 55 60

Leu Ala Ser Ser Lys Val Val Ala Arg Cys Pro Ala Met Gly Pro Ala
65 70 75 80

Thr Leu Pro Glu Glu His Gln Ala Ser Thr Val Cys Arg Arg Asp Gln
85 90 95

Ser Asp Arg Gly Trp Gly Asn His Cys Gly Leu Phe Gly Lys Gly Ser
100 105 110

Ile Val Ala Cys Ala Lys Phe Ala Cys Glu Ala Lys Lys Lys Ala Thr
115 120 125

Gly Tyr Val Tyr Asp Val Asn Lys Ile Thr Tyr Val Val Lys Val Glu
130 135 140

Pro His Thr Gly Asp Tyr Leu Ala Ala Asn Glu Ser His Ser Asn Arg
145 150 155 160

Lys Thr Ala Ser Phe Thr Thr Gln Ser Glu Lys Thr Ile Leu Thr Leu
165 170 175

Gly Asp Tyr Gly Asp Ile Ser Leu Thr Cys Arg Val Thr Ser Gly Val
180 185 190

Asp Pro Ala Gln Thr Val Val Leu Glu Leu Asp Lys Thr Ala Glu His
195 200 205

Leu Pro Lys Ala Trp Gln Val His Arg Asp Trp Phe Glu Asp Leu Ser
210 215 220

Leu Pro Trp Arg His Glu Gly Ala His Glu Trp Asn His Ala Asp Arg
225 230 235 240

Leu Val Glu Phe Gly Glu Pro His Ala Val Lys Met Asp Ile Phe Asn

-continued

```
                245                 250                 255

Leu Gly Asp Gln Thr Gly Ile Leu Leu Lys Ser Leu Ala Gly Val Pro
            260                 265                 270

Val Ala Asn Ile Glu Gly Ser Lys Tyr His Leu Gln Ser Gly His Val
        275                 280                 285

Thr Cys Asp Val Gly Leu Glu Lys Leu Lys Met Lys Gly Met Thr Tyr
    290                 295                 300

Thr Val Cys Glu Gly Ser Lys Phe Ala Trp Lys Arg Pro Pro Thr Asp
305                 310                 315                 320

Ser Gly His Asp Thr Val Val Met Glu Val Thr Tyr Thr Gly Ser Lys
                325                 330                 335

Pro Cys Arg Ile Pro Val Arg Ala Val Ala His Gly Glu Pro Asn Val
            340                 345                 350

Asn Val Ala Ser Leu Ile Thr Pro Asn Pro Ser Met Glu Thr Thr Gly
        355                 360                 365

Gly Gly Phe Val Glu Leu Gln Leu Pro Pro Gly Asp Asn Ile Ile Tyr
    370                 375                 380

Val Gly Glu Leu Ser His Gln Trp Phe Gln Lys Gly Ser Thr Ile Gly
385                 390                 395                 400

Arg Val Leu Glu Lys Thr Arg Arg Gly Ile Glu Arg Leu Thr Val Val
                405                 410                 415

Gly Glu His Ala Trp Asp Phe Gly Ser Val Gly Gly Val Leu Ser Ser
            420                 425                 430

Val Gly Lys Ala Leu His Thr Ala Phe Gly Ala Ala Phe Asn Thr Ile
        435                 440                 445

Phe Gly Gly Val Gly Phe Leu Pro Arg Ile Leu Leu Gly Val Ala Leu
    450                 455                 460

Ala Trp Leu Gly Leu Asn Ser Arg Asn Pro Thr Leu Ser Val Gly Phe
465                 470                 475                 480

Leu Ile Thr Gly Gly Leu Val Leu Thr Met Thr Leu Gly Val Gly Ala
                485                 490                 495


<210> SEQ ID NO 13
<211> LENGTH: 497
<212> TYPE: PRT
<213> ORGANISM: Flavivirus

<400> SEQUENCE: 13

Thr Arg Cys Thr His Leu Glu Asn Arg Asp Phe Val Thr Gly Val Gln
1               5                   10                  15

Gly Thr Thr Arg Val Ser Leu Val Leu Glu Leu Gly Gly Cys Val Thr
            20                  25                  30

Ile Thr Ala Glu Gly Lys Pro Ser Ile Asp Val Trp Leu Glu Asp Ile
        35                  40                  45

Phe Gln Glu Ser Pro Ala Glu Thr Arg Glu Tyr Cys Leu His Ala Lys
    50                  55                  60

Leu Ser Asn Thr Lys Val Glu Ala Arg Cys Pro Thr Thr Gly Pro Ala
65                  70                  75                  80

Thr Leu Pro Glu Glu His Gln Ala Asn Met Val Cys Lys Arg Asp Gln
                85                  90                  95

Ser Asp Arg Gly Trp Gly Asn His Cys Gly Phe Phe Gly Lys Gly Ser
            100                 105                 110

Ile Val Ala Cys Ala Lys Phe Glu Cys Glu Glu Ala Lys Lys Ala Val
        115                 120                 125
```

-continued

```
Gly His Val Tyr Asp Ser Thr Lys Ile Thr Tyr Val Val Lys Val Glu
    130                 135                 140

Pro His Thr Gly Asp Tyr Gln Ala Ala Asn Glu Thr Asn Glu Asn Arg
145                 150                 155                 160

Lys Thr Ala Gln Phe Thr Val Ala Ser Glu Lys Val Ile Leu Asp Leu
                165                 170                 175

Gly Asp Tyr Gly Asp Val Ser Leu Thr Cys Lys Val Ala Ser Gly Ile
            180                 185                 190

Asp Val Ala Gln Thr Val Val Met Ser Leu Gly Ser Ser Lys Asp His
        195                 200                 205

Leu Pro Ser Ala Trp Gln Leu His Arg Asp Trp Phe Glu Asp Leu Ala
    210                 215                 220

Leu Pro Trp Lys His Lys Asp Asn Gln Asp Trp Asn Ser Val Glu Lys
225                 230                 235                 240

Leu Val Glu Phe Gly Pro Pro His Ala Val Lys Met Asp Ile Phe Asn
                245                 250                 255

Leu Gly Asp Gln Thr Ala Val Leu Leu Lys Ser Leu Ala Gly Val Pro
            260                 265                 270

Leu Ala Ser Val Asp Asn Gln Lys Tyr His Leu Lys Ser Gly His Val
        275                 280                 285

Thr Cys Asp Val Gly Leu Glu Lys Leu Lys Leu Lys Gly Thr Thr Tyr
    290                 295                 300

Ser Met Cys Asp Lys Thr Lys Phe Lys Trp Lys Arg Val Pro Val Asp
305                 310                 315                 320

Ser Gly His Asp Thr Val Val Met Glu Val Ser Tyr Thr Gly Ser Asp
                325                 330                 335

Lys Pro Cys Arg Ile Pro Val Arg Ala Val Ala His Gly Val Pro Thr
            340                 345                 350

Ile Asn Val Ala Met Leu Ile Thr Pro Asn Pro Thr Ile Glu Thr Ser
        355                 360                 365

Gly Gly Gly Phe Ile Glu Met Gln Leu Pro Pro Gly Asp Asn Ile Ile
    370                 375                 380

Tyr Val Gly Asp Leu Ser Gln Gln Trp Phe Gln Lys Gly Ser Thr Ile
385                 390                 395                 400

Gly Arg Met Phe Glu Lys Ile Arg Lys Gly Leu Glu Arg Val Ser Val
                405                 410                 415

Val Gly Glu His Ala Trp Asp Phe Gly Ser Val Gly Gly Ile Leu Ser
            420                 425                 430

Ser Val Gly Lys Ala Ile His Thr Val Leu Gly Gly Ala Phe Asn Thr
        435                 440                 445

Leu Phe Gly Gly Val Gly Phe Ile Pro Lys Met Leu Leu Gly Val Ala
    450                 455                 460

Leu Val Trp Leu Gly Leu Asn Ala Arg Asn Pro Thr Met Ser Met Thr
465                 470                 475                 480

Phe Leu Val Val Gly Ala Leu Thr Leu Met Met Thr Met Gly Val Gly
                485                 490                 495

Ala
```

<210> SEQ ID NO 14
<211> LENGTH: 496
<212> TYPE: PRT
<213> ORGANISM: Flavivirus

<400> SEQUENCE: 14

-continued

```
Ser Arg Cys Thr His Leu Glu Asn Arg Asp Phe Val Thr Gly Thr Gln
1               5                   10                  15

Gly Thr Thr Arg Val Thr Leu Val Leu Glu Leu Gly Gly Cys Val Thr
            20                  25                  30

Ile Thr Ala Glu Gly Lys Pro Ser Met Asp Val Trp Leu Asp Ala Ile
        35                  40                  45

Tyr Gln Glu Ser Pro Ala Lys Thr Arg Glu Tyr Cys Leu His Ala Lys
    50                  55                  60

Leu Ser Asp Thr Lys Val Ala Ala Arg Cys Pro Thr Met Gly Pro Ala
65                  70                  75                  80

Ile Leu Ala Glu Glu His Gln Gly Gly Thr Val Cys Lys Arg Asp Gln
                85                  90                  95

Ser Asp Arg Gly Trp Gly Asn His Cys Gly Leu Phe Gly Lys Gly Ser
            100                 105                 110

Ile Val Ala Cys Val Lys Ala Ala Cys Glu Ala Lys Lys Lys Ala Thr
        115                 120                 125

Gly His Val Tyr Asp Ala Asn Lys Ile Val Tyr Thr Val Lys Val Glu
    130                 135                 140

Pro His Thr Gly Asp Tyr Val Ala Ala Asn Glu Thr His Ser Gly Arg
145                 150                 155                 160

Lys Thr Ala Ser Phe Thr Val Ser Ser Glu Lys Thr Ile Leu Thr Met
                165                 170                 175

Gly Glu Tyr Gly Asp Val Ser Leu Leu Cys Arg Val Ala Ser Gly Val
            180                 185                 190

Asp Leu Ala Gln Thr Val Ile Leu Glu Leu Asp Lys Thr Val Glu His
        195                 200                 205

Leu Pro Thr Ala Trp Gln Val His Arg Asp Trp Phe Asn Asp Leu Ala
    210                 215                 220

Leu Pro Trp Lys His Glu Gly Ala Gln Asn Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
        275                 280                 285

Thr Cys Glu Val Gly Leu Glu Lys Leu Lys Met Lys Gly Leu Thr Tyr
    290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
    370                 375                 380

Val Gly Glu Leu Ser His Gln Trp Phe Gln Lys Gly Ser Ser Ile Gly
385                 390                 395                 400

Arg Val Phe Gln Lys Thr Lys Lys Gly Ile Glu Arg Leu Thr Val Ile
                405                 410                 415

Gly Glu His Ala Trp Asp Phe Gly Ser Ala Gly Gly Phe Leu Ser Ser
```

420 425 430

Ile Gly Lys Ala Val His Thr Val Leu Gly Gly Ala Phe Asn Ser Ile
435 440 445

Phe Gly Gly Val Gly Phe Leu Pro Arg Leu Leu Leu Gly Val Ala Leu
450 455 460

Ala Trp Leu Gly Leu Asn Met Arg Asn Pro Thr Met Ser Met Ser Phe
465 470 475 480

Leu Leu Ala Gly Gly Leu Val Leu Ala Met Thr Leu Gly Val Gly Ala
485 490 495

<210> SEQ ID NO 15
<211> LENGTH: 497
<212> TYPE: PRT
<213> ORGANISM: Flavivirus

<400> SEQUENCE: 15

Thr Lys Cys Thr His Leu Glu Asn Arg Asp Phe Val Thr Gly Val Gln
1 5 10 15

Gly Thr Thr Arg Val Ser Leu Val Leu Glu Leu Gly Gly Cys Val Thr
20 25 30

Ile Thr Ala Glu Gly Lys Pro Ser Ile Asp Val Trp Leu Glu Asp Ile
35 40 45

Phe Gln Glu Ser Pro Ala Glu Thr Arg Glu Tyr Cys Leu His Ala Lys
50 55 60

Leu Ser Asn Thr Lys Val Glu Ala Arg Cys Pro Thr Thr Gly Pro Ala
65 70 75 80

Thr Leu Pro Glu Glu His Gln Ala Asn Met Val Cys Lys Arg Asp Gln
85 90 95

Ser Asp Arg Gly Trp Gly Asn His Cys Gly Phe Phe Gly Lys Gly Ser
100 105 110

Ile Val Ala Cys Ala Lys Phe Glu Cys Glu Glu Ala Lys Lys Ala Val
115 120 125

Gly His Val Tyr Asp Ser Thr Lys Ile Thr Tyr Val Val Lys Val Glu
130 135 140

Pro His Thr Gly Asp Tyr Gln Ala Ala Asn Glu Thr Asn Glu Asn Arg
145 150 155 160

Lys Thr Ala Gln Phe Thr Val Ala Ser Glu Lys Val Ile Leu Asn Leu
165 170 175

Gly Asp Tyr Gly Asp Val Ser Leu Thr Cys Lys Val Ala Ser Gly Ile
180 185 190

Asp Val Ala Gln Thr Val Val Met Ser Leu Gly Ser Ser Lys Asp His
195 200 205

Leu Pro Ser Ala Trp Gln Val His Arg Asp Trp Phe Glu Asp Leu Ala
210 215 220

Leu Pro Trp Lys His Lys Asp Asn Gln Asp Trp Asn Ser Val Glu Lys
225 230 235 240

Leu Val Glu Phe Gly Pro Pro His Ala Val Lys Met Asp Ile Phe Asn
245 250 255

Leu Gly Asp Gln Thr Ala Val Leu Leu Lys Ser Leu Ala Gly Val Pro
260 265 270

Leu Ala Ser Val Asp Asn Gln Lys Tyr His Leu Lys Ser Gly His Val
275 280 285

Thr Cys Asp Val Gly Leu Glu Lys Leu Lys Leu Lys Gly Thr Thr Tyr
290 295 300

-continued

Ser Met Cys Asp Lys Thr Lys Phe Lys Trp Lys Arg Val Pro Val Asp
305 310 315 320

Ser Gly His Asp Thr Val Val Met Glu Val Ser Tyr Thr Gly Ser Asp
325 330 335

Lys Pro Cys Arg Ile Pro Val Arg Ala Val Ala His Gly Val Pro Thr
340 345 350

Ile Asn Val Ala Met Leu Ile Thr Pro Asn Pro Thr Ile Glu Thr Ser
355 360 365

Gly Gly Gly Phe Ile Glu Met Gln Leu Pro Pro Gly Asp Asn Ile Ile
370 375 380

Tyr Val Gly Asp Leu Ser Gln Gln Trp Phe Gln Lys Gly Ser Thr Ile
385 390 395 400

Gly Arg Met Phe Glu Lys Thr Arg Lys Gly Leu Glu Arg Phe Ser Val
405 410 415

Val Gly Glu His Ala Trp Asp Phe Gly Ser Val Gly Gly Ile Leu Ser
420 425 430

Ser Val Gly Lys Ala Val His Thr Val Leu Gly Gly Ala Phe Asn Thr
435 440 445

Leu Phe Gly Gly Val Gly Phe Ile Pro Lys Met Leu Leu Gly Val Ala
450 455 460

Leu Val Trp Leu Gly Leu Asn Ala Arg Asn Pro Thr Met Ser Met Thr
465 470 475 480

Phe Leu Ala Val Gly Val Leu Thr Leu Met Met Thr Met Gly Val Gly
485 490 495

Ala

<210> SEQ ID NO 16
<211> LENGTH: 496
<212> TYPE: PRT
<213> ORGANISM: Flavivirus

<400> SEQUENCE: 16

Thr Arg Cys Thr His Leu Gln Asn Arg Asp Phe Val Ser Gly Thr Gln
1 5 10 15

Gly Thr Thr Arg Val Ser Leu Val Leu Glu Leu Gly Gly Cys Val Thr
20 25 30

Leu Thr Ala Glu Gly Lys Pro Ser Val Asp Val Trp Leu Asp Asp Ile
35 40 45

His Gln Glu Asn Pro Ala Lys Thr Arg Glu Tyr Cys Leu His Ala Lys
50 55 60

Leu Ala Asn Ser Lys Val Ala Ala Arg Cys Pro Ala Met Gly Pro Ala
65 70 75 80

Thr Leu Pro Glu Glu His Gln Ala Ser Thr Val Cys Arg Arg Asp Gln
85 90 95

Ser Asp Arg Gly Trp Gly Asn His Cys Gly Leu Phe Gly Lys Gly Ser
100 105 110

Ile Val Ala Cys Ala Lys Phe Ser Cys Glu Thr Lys Lys Lys Ala Thr
115 120 125

Gly Tyr Val Tyr Asp Val Asn Lys Ile Thr Tyr Val Val Lys Val Glu
130 135 140

Pro His Thr Gly Asp Tyr Leu Ala Ala Asn Glu Ser His Ser Asn Arg
145 150 155 160

Lys Thr Ala Ser Phe Thr Thr Gln Ser Glu Lys Thr Ile Leu Thr Leu
165 170 175

-continued

```
Gly Asp Tyr Gly Asp Ile Ser Leu Thr Cys Arg Val Thr Ser Gly Val
            180                 185                 190

Asp Pro Ala Gln Thr Val Val Leu Glu Leu Asp Lys Thr Ala Glu His
        195                 200                 205

Leu Pro Lys Ala Trp Gln Val His Arg Asp Trp Phe Glu Asp Leu Ser
    210                 215                 220

Leu Pro Trp Arg His Glu Gly Ala Gln Glu Trp Asn His Ala Asp Arg
225                 230                 235                 240

Leu Val Glu Phe Gly Glu Pro His Ala Val Lys Met Asp Ile Phe Asn
                245                 250                 255

Leu Gly Asp Gln Thr Gly Ile Leu Leu Lys Ser Leu Ala Gly Val Pro
            260                 265                 270

Val Ala Asn Ile Glu Gly Ser Lys Tyr His Leu Gln Ser Gly His Val
        275                 280                 285

Thr Cys Asp Val Gly Leu Glu Lys Leu Lys Met Lys Gly Met Thr Tyr
    290                 295                 300

Thr Val Cys Glu Gly Ser Lys Phe Ala Trp Lys Arg Pro Pro Thr Asp
305                 310                 315                 320

Ser Gly His Asp Thr Val Val Met Glu Val Thr Tyr Thr Gly Ser Lys
                325                 330                 335

Pro Cys Arg Ile Pro Val Arg Ala Val Ala His Gly Glu Pro Asn Val
            340                 345                 350

Asn Val Ala Ser Leu Ile Thr Pro Asn Pro Ser Met Glu Thr Thr Gly
        355                 360                 365

Gly Gly Phe Val Glu Leu Gln Leu Pro Pro Gly Asp Asn Ile Ile Tyr
    370                 375                 380

Val Gly Glu Leu Ser His Gln Trp Phe Gln Lys Gly Ser Thr Ile Gly
385                 390                 395                 400

Arg Val Leu Glu Lys Thr Arg Arg Gly Ile Glu Arg Leu Thr Val Val
                405                 410                 415

Gly Glu His Ala Trp Asp Phe Gly Ser Val Gly Gly Met Leu Ser Ser
            420                 425                 430

Val Gly Lys Ala Leu His Thr Ala Phe Gly Ala Ala Phe Asn Thr Ile
        435                 440                 445

Phe Gly Gly Val Gly Phe Leu Pro Arg Ile Leu Leu Gly Val Ala Leu
    450                 455                 460

Ala Trp Leu Gly Leu Asn Ser Arg Asn Pro Thr Leu Ser Val Gly Phe
465                 470                 475                 480

Leu Ile Thr Gly Gly Leu Val Leu Thr Met Thr Leu Gly Val Gly Ala
                485                 490                 495
```

<210> SEQ ID NO 17
<211> LENGTH: 496
<212> TYPE: PRT
<213> ORGANISM: Flavivirus

<400> SEQUENCE: 17

```
Ser Arg Cys Val His Leu Glu Asn Arg Asp Phe Val Thr Gly Thr Gln
1               5                   10                  15

Gly Thr Thr Ala Val Thr Leu Val Leu Glu Leu Gly Gly Cys Val Thr
            20                  25                  30

Leu Ser Ala Glu Gly Lys Pro Ser Ile Asp Leu Trp Leu Lys Ser Ile
        35                  40                  45

His Gln Asp Ser Leu Ala Ile Thr Arg Glu Tyr Cys Leu His Ala Lys
    50                  55                  60
```

-continued

Leu Thr Asp Thr Lys Val Ala Ala Arg Cys Pro Thr Thr Gly Pro Ala
65 70 75 80

Thr Leu Pro Glu Glu His Gln Lys Asn Met Val Cys Lys Arg Asp Gln
85 90 95

Ser Asp Arg Gly Trp Gly Asn His Cys Gly Leu Phe Gly Lys Gly Ser
100 105 110

Ile Val Gly Cys Thr Lys Phe Asp Cys Glu Val Asn Lys Lys Ala Thr
115 120 125

Gly Arg Val Phe Asp Ile Thr Lys Ile Val Tyr Thr Val Lys Val Glu
130 135 140

Pro His Thr Gly Thr Tyr Val Ala Ala Asn Glu Thr Asn Ser Asp Arg
145 150 155 160

Lys Ser Val Glu Phe Thr Ala Gln Ser Glu Lys Lys Thr Ile Ser Leu
165 170 175

Gly Ser Tyr Gly Glu Val Gly Leu Ser Cys Arg Val Asn Ser Gly Ile
180 185 190

Asp Val Asp Gln Thr Val Val Leu Glu Leu Glu Gly Gln Ala Leu His
195 200 205

Pro Lys Gly Trp Ala Val His Lys Asp Trp Phe Gly Asp Leu Ala Leu
210 215 220

Pro Trp Lys His His Glu Ala Glu Ile Trp Glu Asp Lys Glu Arg Leu
225 230 235 240

Val Glu Phe Gly Pro Pro His Ala Val Lys Met Asp Val Tyr Asn Leu
245 250 255

Gly Asp Gln Thr Gly Ile Leu Met Arg Ser Leu Ala Gly Ala Ser Val
260 265 270

Val Asp Val Gln Gly Thr Lys Val Phe Leu Gln Ser Gly His Val Thr
275 280 285

Cys Asn Val Gly Leu Glu Lys Leu Lys Leu Lys Gly Met Thr Tyr Ser
290 295 300

Met Cys Glu Glu Gly Lys Phe Ala Trp Lys Arg Pro Pro Thr Asp Ser
305 310 315 320

Gly His Asp Thr Val Val Met Glu Val Thr Tyr Thr Gly Thr Val Lys
325 330 335

Pro Cys Arg Ile Gln Val Arg Ala Glu Ala Lys Gly Ala Pro Asn Val
340 345 350

Asp Val Ala Asn Leu Ile Thr Pro Asn Pro Thr Ile Glu Asn Glu Gly
355 360 365

Gly Gly Tyr Ile Glu Met Gln Leu Pro Pro Gly Asp Asn Thr Ile Tyr
370 375 380

Ile Gly Asn Leu His Gln Ala Trp Phe Gln Lys Gly Ser Ser Ile Gly
385 390 395 400

Arg Val Phe Glu Lys Thr Arg Lys Gly Ile Gln Arg Leu Ala Ala Val
405 410 415

Gly Glu His Ala Trp Asp Phe Gly Ser Val Gly Gly Phe Phe Gly Ser
420 425 430

Ile Gly Lys Ala Val His Met Val Leu Gly Gly Leu Phe Gly Val Leu
435 440 445

Phe Gly Gly Ile Gly Phe Ile Pro Lys Met Leu Met Gly Ala Ala Leu
450 455 460

Ile Trp Leu Gly Ile Asn Met Lys Asn Thr Thr Leu Ser Leu Ser Phe
465 470 475 480

Leu Ala Thr Gly Gly Leu Ile Leu Met Met Thr Leu Gly Val Gly Ala
485 490 495

<210> SEQ ID NO 18
<211> LENGTH: 496
<212> TYPE: PRT
<213> ORGANISM: Flavivirus

<400> SEQUENCE: 18

Ser Arg Cys Thr His Leu Glu Asn Arg Asp Phe Val Thr Gly Val Gln
1 5 10 15

Gly Thr Thr Arg Leu Thr Leu Val Leu Glu Leu Gly Gly Cys Val Thr
20 25 30

Val Thr Ala Asp Gly Lys Pro Ser Leu Asp Val Trp Leu Asp Ser Ile
35 40 45

Tyr Gln Glu Ser Pro Ala Gln Thr Arg Glu Tyr Cys Leu His Ala Lys
50 55 60

Leu Thr Gly Thr Lys Val Ala Ala Arg Cys Pro Thr Met Gly Pro Ala
65 70 75 80

Thr Leu Pro Glu Glu His Gln Ser Gly Thr Val Cys Lys Arg Asp Gln
85 90 95

Ser Asp Arg Gly Trp Gly Asn His Cys Gly Leu Phe Gly Lys Gly Ser
100 105 110

Ile Val Thr Cys Val Lys Phe Thr Cys Glu Asp Lys Lys Lys Ala Thr
115 120 125

Gly His Val Tyr Asp Val Asn Lys Ile Thr Tyr Thr Ile Lys Val Glu
130 135 140

Pro His Thr Gly Glu Phe Val Ala Ala Asn Glu Thr His Ser Gly Arg
145 150 155 160

Lys Ser Ala Ser Phe Thr Val Ser Ser Glu Lys Thr Ile Leu Thr Leu
165 170 175

Gly Asp Tyr Gly Asp Val Ser Leu Leu Cys Arg Val Ala Ser Gly Val
180 185 190

Asp Leu Ala Gln Thr Val Val Leu Ala Leu Asp Lys Thr His Glu His
195 200 205

Leu Pro Thr Ala Trp Gln Val His Arg Asp Trp Phe Asn Asp Leu Ala
210 215 220

Leu Pro Trp Lys His Asp Gly Ala Glu Ala Trp Asn Glu Ala Gly Arg
225 230 235 240

Leu Val Glu Phe Gly Thr Pro His Ala Val Lys Met Asp Val Phe Asn
245 250 255

Leu Gly Asp Gln Thr Gly Val Leu Leu Lys Ser Leu Ala Gly Val Pro
260 265 270

Val Ala Ser Ile Glu Gly Thr Lys Tyr His Leu Lys Ser Gly His Val
275 280 285

Thr Cys Glu Val Gly Leu Glu Lys Leu Lys Met Lys Gly Leu Thr Tyr
290 295 300

Thr Val Cys Asp Lys Thr Lys Phe Thr Trp Lys Arg Ala Pro Thr Asp
305 310 315 320

Ser Gly His Asp Thr Val Val Met Glu Val Gly Phe Ser Gly Thr Arg
325 330 335

Pro Cys Arg Ile Pro Val Arg Ala Val Ala His Gly Val Pro Glu Val
340 345 350

Asn Val Ala Met Leu Ile Thr Pro Asn Pro Thr Met Glu Asn Asn Gly
355 360 365

-continued

Gly Gly Phe Ile Glu Met Gln Leu Pro Pro Gly Asp Asn Ile Ile Tyr
370 375 380

Val Gly Asp Leu Asn His Gln Trp Phe Gln Lys Gly Ser Ser Ile Gly
385 390 395 400

Arg Val Leu Gln Lys Thr Arg Lys Gly Ile Glu Arg Leu Thr Val Leu
405 410 415

Gly Glu His Ala Trp Asp Phe Gly Ser Val Gly Gly Val Met Thr Ser
420 425 430

Ile Gly Arg Ala Met His Thr Val Leu Gly Gly Ala Phe Asn Thr Leu
435 440 445

Leu Gly Gly Val Gly Phe Leu Pro Lys Ile Leu Leu Gly Val Ala Met
450 455 460

Ala Trp Leu Gly Leu Asn Met Arg Asn Pro Thr Leu Ser Met Gly Phe
465 470 475 480

Leu Leu Ser Gly Gly Leu Val Leu Ala Met Thr Leu Gly Val Gly Ala
485 490 495

<210> SEQ ID NO 19
<211> LENGTH: 496
<212> TYPE: PRT
<213> ORGANISM: Flavivirus

<400> SEQUENCE: 19

Ser Arg Cys Thr His Leu Glu Asn Arg Asp Phe Val Thr Gly Thr Gln
1 5 10 15

Gly Thr Thr Arg Val Thr Leu Val Leu Glu Leu Gly Gly Cys Val Thr
20 25 30

Ile Thr Ala Glu Gly Lys Pro Ser Met Asp Val Trp Leu Asp Ala Ile
35 40 45

Tyr Gln Glu Ser Pro Ala Lys Thr Arg Glu Tyr Cys Leu His Ala Lys
50 55 60

Leu Ser Asp Thr Lys Val Ala Ala Arg Cys Pro Thr Met Gly Pro Ala
65 70 75 80

Thr Leu Ala Glu Glu His Gln Gly Gly Thr Val Cys Lys Arg Asp Gln
85 90 95

Ser Asp Arg Gly Trp Gly Asn His Cys Gly Leu Phe Gly Lys Gly Ser
100 105 110

Ile Val Ala Cys Val Lys Ala Ala Cys Glu Ala Lys Lys Lys Ala Thr
115 120 125

Gly His Val Tyr Asp Ala Asn Lys Ile Val Tyr Thr Val Lys Val Glu
130 135 140

Pro His Thr Gly Asp Tyr Val Ala Ala Asn Glu Thr His Ser Gly Arg
145 150 155 160

Lys Thr Ala Ser Phe Thr Val Ser Ser Glu Lys Thr Ile Leu Thr Met
165 170 175

Gly Glu Tyr Gly Asp Val Ser Leu Leu Cys Arg Val Ala Ser Gly Val
180 185 190

Asp Leu Pro Gln Thr Val Ile Leu Glu Leu Asp Lys Thr Val Glu His
195 200 205

Leu Pro Thr Ala Trp Gln Val His Arg Asp Trp Phe Asn Asp Leu Ala
210 215 220

Leu Pro Trp Lys His Glu Gly Ala Gln Asn Trp Asn Asn Ala Glu Arg
225 230 235 240

Leu Val Glu Phe Gly Ala Pro His Ala Val Lys Met Asp Val Tyr Asn

-continued

```
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
        275                 280                 285

Thr Cys Glu Val Gly Leu Glu Lys Leu Lys Met Lys Gly Leu Thr Tyr
    290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
    370                 375                 380

Val Gly Glu Leu Ser His Gln Trp Phe Gln Lys Gly Ser Ser Ile Gly
385                 390                 395                 400

Arg Val Phe Gln Lys Thr Lys Lys Gly Ile Glu Arg Leu Thr Val Ile
                405                 410                 415

Gly Glu His Ala Trp Asp Phe Gly Ser Ala Gly Gly Phe Leu Ser Ser
            420                 425                 430

Ile Gly Lys Ala Val His Thr Val Leu Gly Gly Ala Phe Asn Ser Ile
        435                 440                 445

Phe Gly Gly Val Gly Phe Leu Pro Lys Leu Leu Leu Gly Val Ala Leu
    450                 455                 460

Ala Trp Leu Gly Leu Asn Met Arg Asn Pro Thr Met Ser Met Ser Phe
465                 470                 475                 480

Leu Leu Ala Gly Gly Leu Val Leu Ala Met Thr Leu Gly Val Gly Ala
                485                 490                 495


<210> SEQ ID NO 20
<211> LENGTH: 496
<212> TYPE: PRT
<213> ORGANISM: Flavivirus

<400> SEQUENCE: 20

Ser Arg Cys Thr His Leu Glu Asn Arg Asp Phe Val Thr Gly Thr Gln
1               5                   10                  15

Gly Thr Thr Arg Val Thr Leu Val Leu Glu Leu Gly Gly Cys Val Thr
            20                  25                  30

Ile Thr Ala Glu Gly Lys Pro Ser Met Asp Val Trp Leu Asp Ser Ile
        35                  40                  45

Tyr Gln Glu Asn Pro Ala Lys Thr Arg Glu Tyr Cys Leu His Ala Lys
    50                  55                  60

Leu Ser Asp Thr Lys Val Ala Ala Arg Cys Pro Thr Met Gly Pro Ala
65                  70                  75                  80

Thr Leu Ala Glu Glu His Gln Gly Gly Thr Val Cys Lys Arg Asp Gln
                85                  90                  95

Ser Asp Arg Gly Trp Gly Asn His Cys Gly Leu Phe Gly Lys Gly Ser
            100                 105                 110

Ile Val Ala Cys Val Lys Ala Ala Cys Glu Ala Lys Lys Lys Ala Thr
        115                 120                 125
```

```
Gly His Val Tyr Asp Ala Asn Lys Ile Val Tyr Thr Val Lys Val Glu
    130                 135                 140

Pro His Thr Gly Asp Tyr Val Ala Ala Asn Glu Thr His Ser Gly Arg
145                 150                 155                 160

Lys Thr Ala Ser Phe Thr Val Ser Ser Glu Lys Thr Ile Leu Thr Met
                165                 170                 175

Gly Glu Tyr Gly Asp Val Ser Leu Leu Cys Arg Val Ala Ser Gly Val
            180                 185                 190

Asp Leu Ala Gln Thr Val Ile Leu Glu Leu Asp Lys Thr Val Glu His
        195                 200                 205

Leu Pro Thr Ala Trp Gln Val His Arg Asp Trp Phe Asn Asp Leu Ala
    210                 215                 220

Leu Pro Trp Lys His Glu Gly Ala Gln Asn Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
        275                 280                 285

Thr Cys Glu Val Gly Leu Glu Lys Leu Lys Met Lys Gly Leu Thr Tyr
    290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Thr Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
    370                 375                 380

Val Gly Glu Leu Ser His Gln Trp Phe Gln Lys Gly Ser Ser Ile Gly
385                 390                 395                 400

Arg Val Phe Gln Lys Thr Lys Lys Gly Ile Glu Arg Leu Thr Val Ile
                405                 410                 415

Gly Glu His Ala Trp Asp Phe Gly Ser Ala Gly Gly Phe Leu Ser Ser
            420                 425                 430

Ile Gly Lys Ala Val His Thr Val Leu Gly Gly Ala Phe Asn Ser Ile
        435                 440                 445

Phe Gly Gly Val Gly Phe Leu Pro Lys Leu Leu Leu Gly Val Ala Leu
    450                 455                 460

Ala Trp Leu Gly Leu Asn Met Arg Asn Pro Thr Met Ser Met Ser Phe
465                 470                 475                 480

Leu Leu Ala Gly Gly Leu Val Leu Ala Met Thr Leu Gly Val Gly Ala
                485                 490                 495
```

<210> SEQ ID NO 21
<211> LENGTH: 497
<212> TYPE: PRT
<213> ORGANISM: Flavivirus

<400> SEQUENCE: 21

```
Thr Arg Cys Thr His Leu Glu Asn Arg Asp Phe Val Thr Gly Thr Gln
1               5                   10                  15
```

-continued

```
Gly Thr Thr Arg Val Ser Leu Val Leu Glu Leu Gly Gly Cys Val Thr
            20                  25                  30

Ile Thr Ala Glu Gly Lys Pro Ser Ile Asp Val Trp Leu Glu Asp Ile
        35                  40                  45

Phe Gln Glu Ser Pro Ala Glu Thr Arg Glu Tyr Cys Leu His Ala Lys
    50                  55                  60

Leu Thr Asn Thr Lys Val Glu Ala Arg Cys Pro Thr Thr Gly Pro Ala
65                  70                  75                  80

Thr Leu Pro Glu Glu His Gln Ala Asn Met Val Cys Lys Arg Asp Gln
                85                  90                  95

Ser Asp Arg Gly Trp Gly Asn His Cys Gly Phe Phe Gly Lys Gly Ser
            100                 105                 110

Ile Val Ala Cys Ala Lys Phe Glu Cys Glu Glu Ala Lys Lys Ala Val
        115                 120                 125

Gly His Val Tyr Asp Ser Thr Lys Ile Thr Tyr Val Val Lys Val Glu
    130                 135                 140

Pro His Thr Gly Asp Tyr Leu Ala Ala Asn Glu Thr Asn Ser Asn Arg
145                 150                 155                 160

Lys Ser Ala Gln Phe Thr Val Ala Ser Glu Lys Val Ile Leu Arg Leu
                165                 170                 175

Gly Asp Tyr Gly Asp Val Ser Leu Thr Cys Lys Val Ala Ser Gly Ile
            180                 185                 190

Asp Val Ala Gln Thr Val Val Met Ser Leu Asp Ser Ser Lys Asp His
        195                 200                 205

Leu Pro Ser Ala Trp Gln Val His Arg Asp Trp Phe Glu Asp Leu Ala
    210                 215                 220

Leu Pro Trp Lys His Lys Asp Asn Gln Asp Trp Asn Ser Val Glu Lys
225                 230                 235                 240

Leu Val Glu Phe Gly Pro Pro His Ala Val Lys Met Asp Val Phe Asn
                245                 250                 255

Leu Gly Asp Gln Thr Ala Val Leu Leu Lys Ser Leu Ala Gly Val Pro
            260                 265                 270

Leu Ala Ser Val Glu Gly Gln Lys Tyr His Leu Lys Ser Gly His Val
        275                 280                 285

Thr Cys Asp Val Gly Leu Glu Lys Leu Lys Leu Lys Gly Thr Thr Tyr
    290                 295                 300

Ser Met Cys Asp Lys Ala Lys Phe Lys Trp Lys Arg Val Pro Val Asp
305                 310                 315                 320

Ser Gly His Asp Thr Val Val Met Glu Val Ser Tyr Thr Gly Ser Asp
                325                 330                 335

Lys Pro Cys Arg Ile Pro Val Arg Ala Val Ala His Gly Val Pro Ala
            340                 345                 350

Val Asn Val Ala Met Leu Ile Thr Pro Asn Pro Thr Ile Glu Thr Asn
        355                 360                 365

Gly Gly Gly Phe Ile Glu Met Gln Leu Pro Pro Gly Asp Asn Ile Ile
    370                 375                 380

Tyr Val Gly Asp Leu Ser Gln Gln Trp Phe Gln Lys Gly Ser Thr Ile
385                 390                 395                 400

Gly Arg Met Phe Glu Lys Thr Arg Arg Gly Leu Glu Arg Leu Ser Val
                405                 410                 415

Val Gly Glu His Ala Trp Asp Phe Gly Ser Val Gly Gly Val Leu Ser
            420                 425                 430
```

Ser Val Gly Lys Ala Ile His Thr Val Leu Gly Gly Ala Phe Asn Thr
        435                 440                 445

Leu Phe Gly Gly Val Gly Phe Ile Pro Lys Met Leu Leu Gly Val Ala
    450                 455                 460

Leu Val Trp Leu Gly Leu Asn Ala Arg Asn Pro Thr Met Ser Met Thr
465                 470                 475                 480

Phe Leu Ala Val Gly Ala Leu Thr Leu Met Met Thr Met Gly Val Gly
                485                 490                 495

Ala

<210> SEQ ID NO 22
<211> LENGTH: 496
<212> TYPE: PRT
<213> ORGANISM: Flavivirus

<400> SEQUENCE: 22

Ser Arg Cys Thr His Leu Glu Asn Arg Asp Phe Val Glu Gly Val Thr
1               5                   10                  15

Gly Thr Thr Lys Val Thr Leu Val Leu Glu Leu Gly Gly Cys Val Thr
            20                  25                  30

Val Thr Ala Glu Gly Arg Pro Ser Val Asp Val Trp Leu Asp Ser Ile
        35                  40                  45

Tyr Gln Glu Ser Leu Ala Gln Val Arg Glu Tyr Cys Leu His Ala Lys
    50                  55                  60

Leu Ser Asn Ser Lys Val Ala Ala Arg Cys Pro Thr Met Gly Pro Ala
65                  70                  75                  80

Thr Leu Pro Glu Glu His Gln Ala Asp Met Val Cys Lys Arg Asp Gln
                85                  90                  95

Ser Asp Arg Gly Trp Gly Asn His Cys Gly Leu Phe Gly Lys Gly Ser
            100                 105                 110

Ile Val Ala Cys Thr Lys Phe Thr Cys Glu Glu Lys Arg Thr Ala Ala
        115                 120                 125

Gly Tyr Val Phe Asp Ser Ser Lys Val Thr Phe Ala Val Lys Val Glu
    130                 135                 140

Pro His Thr Gly Thr Tyr Leu Ala Ala Asn Asp Thr His Val Asp Arg
145                 150                 155                 160

Lys Glu Ala Lys Phe Thr Ala Ala Ala Glu Lys Val Ile Leu Thr Leu
                165                 170                 175

Gly Asp Tyr Gly Asp Met Ser Leu Val Cys Arg Val Thr Ser Gly Met
            180                 185                 190

Asp Met Ala Gln Thr Val Ile Leu Glu Met Asp Lys Thr Asn Glu His
        195                 200                 205

Leu Pro Gln Ala Trp Gln Val His Arg Ser Trp Phe Glu Asp Leu Ser
    210                 215                 220

Leu Pro Trp Arg His Lys Gly Glu Ser Ala Trp Arg Glu Ala Gln Arg
225                 230                 235                 240

Leu Val Glu Phe Gly Pro Pro His Ala Val Lys Met Asp Val Tyr Asn
                245                 250                 255

Leu Gly Asp Gln Thr Ser Val Met Leu Lys Ser Leu Thr Gly Ala Gly
            260                 265                 270

Met Val Arg Leu Glu Gly Thr Lys Val Phe Met Gln Ser Gly His Ile
        275                 280                 285

Thr Cys Asp Val Gly Leu Glu Lys Leu Lys Leu Lys Gly Ile Thr Tyr
    290                 295                 300

Ser Met Cys Glu Ser Gly Lys Phe Ser Trp Lys Arg Pro Pro Thr Asp
305 310 315 320

Ser Gly His Asp Thr Val Val Met Glu Val Ser Tyr Ser Gly Ala Thr
325 330 335

Lys Pro Cys Arg Ile Pro Val Met Ala Thr Ala His Gly Glu Glu Ser
340 345 350

Asn Val Ala Met Leu Ile Thr Ser Asn Pro Thr Ile Glu Thr Asp Lys
355 360 365

Gly Gly Phe Ile Glu Met Gln Val Pro Pro Gly Asp Ile Thr Ile Lys
370 375 380

Ile Gly Asp Leu Lys Gln Gln Trp Phe Gln Lys Gly Ser Thr Ile Gly
385 390 395 400

Arg Val Phe Gln Lys Thr Arg Arg Gly Val Glu Arg Leu Val Ala Val
405 410 415

Gly Glu His Ala Trp Asp Phe Gly Ser Val Gly Gly Val Phe Ser Ser
420 425 430

Val Ala Lys Ala Cys His Met Val Leu Gly Asn Leu Phe Gly Ala Val
435 440 445

Phe Gly Gly Phe Gly Phe Leu Pro Arg Ile Leu Ile Gly Ala Gly Leu
450 455 460

Val Trp Leu Gly Leu Asn Ala Arg Asn Val Thr Leu Ser Val Gly Phe
465 470 475 480

Leu Ala Val Gly Gly Ile Leu Leu Ala Leu Thr Leu Gly Val Gly Ala
485 490 495

<210> SEQ ID NO 23
<211> LENGTH: 496
<212> TYPE: PRT
<213> ORGANISM: Flavivirus

<400> SEQUENCE: 23

Ser Arg Cys Thr His Leu Glu Asn Arg Asp Phe Val Thr Gly Thr Gln
1 5 10 15

Gly Thr Thr Arg Val Thr Leu Val Leu Glu Leu Gly Gly Cys Val Thr
20 25 30

Ile Thr Ala Glu Gly Lys Pro Ser Met Asp Val Trp Leu Asp Ala Ile
35 40 45

Tyr Gln Glu Ser Pro Ala Lys Thr Arg Glu Tyr Cys Leu His Ala Lys
50 55 60

Leu Ser Asp Thr Lys Val Ala Ala Arg Cys Pro Thr Met Gly Pro Ala
65 70 75 80

Thr Leu Ala Glu Glu His Gln Gly Gly Thr Val Cys Lys Arg Asp Gln
85 90 95

Ser Asp Arg Gly Trp Gly Asn His Cys Gly Leu Phe Gly Lys Gly Ser
100 105 110

Ile Val Ala Cys Val Lys Ala Ala Cys Glu Ala Lys Lys Lys Ala Thr
115 120 125

Gly His Val Tyr Asp Ala Asn Lys Ile Val Tyr Thr Val Lys Val Glu
130 135 140

Pro His Thr Gly Asp Tyr Val Ala Ala Asn Glu Thr His Ser Gly Arg
145 150 155 160

Lys Thr Ala Ser Phe Thr Val Ser Ser Glu Lys Thr Ile Leu Thr Met
165 170 175

Gly Glu Tyr Gly Asp Val Ser Leu Leu Cys Arg Val Ala Ser Gly Val
180 185 190

Asp Leu Ala Gln Thr Val Ile Leu Glu Leu Asp Lys Thr Val Glu His
195 200 205

Leu Pro Thr Ala Trp Gln Val His Arg Asp Trp Phe Asn Asp Leu Ala
210 215 220

Leu Pro Trp Lys His Glu Gly Ala Gln Asn Trp Asn Asn Ala Glu Arg
225 230 235 240

Leu Val Glu Phe Gly Ala Pro His Ala Val Lys Met Asp Val Tyr Asn
245 250 255

Leu Gly Asp Gln Thr Gly Val Leu Leu Lys Ala Leu Ala Gly Val Pro
260 265 270

Val Ala His Ile Glu Gly Thr Lys Tyr His Leu Lys Ser Gly Pro Val
275 280 285

Thr Cys Glu Val Gly Leu Glu Lys Leu Lys Met Lys Gly Leu Thr Tyr
290 295 300

Thr Met Cys Asp Lys Thr Lys Phe Thr Trp Lys Arg Ala Pro Thr Asp
305 310 315 320

Ser Gly His Asp Thr Val Val Met Glu Val Thr Phe Ser Gly Thr Lys
325 330 335

Pro Cys Arg Ile Pro Val Arg Ala Val Ala His Gly Ser Pro Asp Ala
340 345 350

Asn Val Ala Met Leu Ile Thr Pro Asn Pro Thr Ile Glu Asn Asn Gly
355 360 365

Gly Gly Phe Ile Glu Met Gln Leu Pro Pro Gly Asp Asn Ile Ile Tyr
370 375 380

Val Gly Glu Leu Ser His Gln Trp Phe Gln Lys Gly Ser Ser Ile Gly
385 390 395 400

Arg Val Phe Gln Lys Thr Lys Lys Gly Ile Glu Arg Leu Thr Val Met
405 410 415

Gly Glu His Ala Trp Asp Phe Gly Ser Ala Gly Gly Phe Leu Ser Ser
420 425 430

Ile Gly Lys Ala Val His Thr Val Leu Gly Gly Ala Phe Asn Ser Ile
435 440 445

Phe Gly Gly Val Gly Phe Leu Pro Lys Leu Leu Leu Gly Val Ala Leu
450 455 460

Ala Trp Leu Gly Leu Asn Met Arg Asn Pro Thr Met Ser Met Ser Phe
465 470 475 480

Leu Leu Ala Gly Gly Leu Val Leu Ala Met Thr Leu Gly Val Gly Ala
485 490 495

<210> SEQ ID NO 24
<211> LENGTH: 496
<212> TYPE: PRT
<213> ORGANISM: Flavivirus

<400> SEQUENCE: 24

Ser Arg Cys Thr His Leu Glu Asn Arg Asp Phe Val Thr Gly Thr Gln
1 5 10 15

Gly Thr Thr Arg Val Thr Leu Val Leu Glu Leu Gly Gly Cys Val Thr
20 25 30

Ile Thr Ala Glu Gly Lys Pro Ser Met Asp Val Trp Leu Asp Ala Ile
35 40 45

Tyr Gln Glu Ser Pro Ala Lys Thr Arg Glu Tyr Cys Leu His Ala Lys
50 55 60

Leu Ser Asp Thr Lys Val Ala Ala Arg Cys Pro Thr Met Gly Pro Ala

-continued

```
65                  70                  75                  80

Thr Leu Ala Glu Glu His Gln Gly Gly Thr Val Cys Lys Arg Asp Gln
                85                  90                  95

Ser Asp Arg Gly Trp Gly Asn His Cys Gly Leu Phe Gly Lys Gly Ser
            100                 105                 110

Ile Val Ala Cys Val Lys Ala Ala Cys Glu Ala Lys Lys Lys Ala Thr
        115                 120                 125

Gly His Val Tyr Asp Ala Asn Lys Ile Val Tyr Thr Val Lys Val Glu
    130                 135                 140

Pro His Thr Gly Asp Tyr Val Ala Ala Asn Glu Thr His Ser Gly Arg
145                 150                 155                 160

Lys Thr Ala Ser Phe Thr Val Ser Leu Glu Lys Thr Ile Leu Thr Met
                165                 170                 175

Gly Glu Tyr Gly Asp Val Ser Leu Leu Cys Arg Val Ala Ser Gly Val
            180                 185                 190

Asp Leu Ala Gln Thr Val Ile Leu Glu Leu Asp Lys Thr Val Glu His
        195                 200                 205

Leu Pro Thr Ala Trp Gln Val His Arg Asp Trp Phe Asn Asp Leu Ala
    210                 215                 220

Leu Pro Trp Lys His Glu Gly Ala Gln Asn Trp Asn Asn Ala Glu Arg
225                 230                 235                 240

Leu Val Glu Phe Gly Ala Pro His Ala Val Lys Met Asp Val Tyr Asn
                245                 250                 255

Leu Gly Asp Gln Thr Gly Val Leu Leu Lys Ala Leu Ala Gly Val Pro
            260                 265                 270

Val Ala His Ile Glu Gly Thr Lys Tyr His Leu Lys Ser Gly His Val
        275                 280                 285

Thr Cys Lys Val Gly Leu Glu Lys Leu Lys Met Lys Gly Leu Thr Tyr
    290                 295                 300

Thr Met Cys Asp Lys Thr Lys Phe Thr Trp Lys Arg Ala Pro Thr Asp
305                 310                 315                 320

Ser Gly His Asp Thr Val Val Met Glu Val Ser Phe Ser Gly Thr Lys
                325                 330                 335

Pro Cys Arg Ile Pro Val Arg Ala Val Ala His Gly Ser Pro Asp Val
            340                 345                 350

Asn Val Ala Met Leu Ile Thr Pro Asn Pro Thr Ile Glu Asn Asn Gly
        355                 360                 365

Gly Gly Phe Ile Glu Met Gln Leu Pro Pro Gly Asp Asn Ile Ile Tyr
    370                 375                 380

Val Gly Glu Leu Ser His Gln Trp Phe Gln Lys Gly Ser Ser Ile Gly
385                 390                 395                 400

Arg Val Phe Gln Lys Thr Lys Lys Gly Ile Glu Arg Leu Thr Val Ile
                405                 410                 415

Gly Glu His Ala Trp Asp Phe Gly Ser Ala Gly Gly Phe Leu Ser Ser
            420                 425                 430

Ile Gly Lys Ala Val His Thr Val Leu Gly Gly Ala Phe Asn Ser Ile
        435                 440                 445

Phe Gly Gly Val Gly Phe Leu Pro Lys Leu Leu Leu Gly Val Ala Leu
    450                 455                 460

Ala Trp Leu Gly Leu Asn Met Arg Asn Pro Thr Met Ser Met Ser Phe
465                 470                 475                 480

Leu Leu Ala Gly Gly Leu Val Leu Ala Met Thr Leu Gly Val Gly Ala
                485                 490                 495
```

<210> SEQ ID NO 25
<211> LENGTH: 495
<212> TYPE: PRT
<213> ORGANISM: Flavivirus

<400> SEQUENCE: 25

```
Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Thr Val Gln Tyr Glu Asn Leu Lys Tyr Ser Val Ile Val Thr Val His
    130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Thr Glu Ile Gln Leu Thr
                165                 170                 175

Asp Tyr Gly Ala Leu Thr Leu Asp Tyr Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Ala
305                 310                 315                 320

Leu Val Gln Ile Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Ser Gly Glu Ser Tyr Ile Val Met Gly Ala Gly Glu
```

```
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Ile Gly Ser Ile Gly Gly Val Phe Thr Ser Val
            420                 425                 430

Gly Lys Leu Val His Gln Ile Phe Gly Thr Ala Tyr Gly Val Leu Phe
        435                 440                 445

Ser Gly Val Ser Trp Thr Met Lys Ile Gly Ile Gly Val Leu Leu Thr
    450                 455                 460

Trp Leu Gly Leu Asn Ser Arg Ser Thr Ser Leu Ser Met Thr Cys Ile
465                 470                 475                 480

Ala Val Gly Leu Val Thr Leu Tyr Leu Gly Val Met Val Gln Ala
                485                 490                 495


<210> SEQ ID NO 26
<211> LENGTH: 495
<212> TYPE: PRT
<213> ORGANISM: Flavivirus

<400> SEQUENCE: 26

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Lys Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Ile Val Val Thr Pro His
    130                 135                 140

Ser Gly Glu Glu His Ala Val Gly Asn Asp Thr Gly Lys His Gly Gln
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Lys Gln Glu Ser Asn Trp Ile Gln Lys Glu Thr Leu Val Thr Phe
225                 230                 235                 240

Lys Asn Pro Pro Pro Lys Lys Gln Asp Val Val Val Leu Gly Ser Gln
                245                 250                 255
```

-continued

Glu Gly Ala Met His Thr Ala Leu Thr Gly Ala Thr Glu Ile Gln Met
260 265 270

Ser Ser Gly Asn Leu Leu Phe Thr Gly His Leu Lys Cys Arg Leu Arg
275 280 285

Met Asp Lys Leu Gln Leu Lys Gly Met Ser Tyr Ser Met Cys Thr Gly
290 295 300

Lys Phe Lys Val Val Lys Glu Ile Ala Glu Thr Gln His Gly Thr Ile
305 310 315 320

Val Ile Arg Val Gln Tyr Glu Gly Asp Gly Ser Pro Cys Lys Ile Pro
325 330 335

Phe Glu Ile Met Asp Leu Glu Lys Arg Tyr Val Leu Gly Arg Val Ile
340 345 350

Thr Val Asn Pro Ile Val Thr Glu Lys Asp Ser Pro Val Asn Ile Glu
355 360 365

Ala Glu Pro Pro Phe Gly Asp Ser Tyr Leu Ile Ile Gly Leu Asp Pro
370 375 380

Gly Gln Leu Lys Leu Asn Gly Phe Lys Lys Gly Ser Ser Ile Gly Gln
385 390 395 400

Met Phe Glu Thr Thr Ile Arg Gly Met Arg Arg Met Ala Ile Leu Gly
405 410 415

Ala Thr Ala Trp Asp Phe Gly Ser Leu Gly Gly Val Phe Thr Ser Ile
420 425 430

Gly Lys Ala Leu His Gln Val Phe Gly Ala Ile Phe Gly Ala Ala Phe
435 440 445

Ser Gly Val Ser Trp Thr Met Lys Ile Leu Ile Gly Val Ile Ile Thr
450 455 460

Trp Ile Gly Met Asn Ser Arg Ser Thr Ser Leu Ser Val Ser Leu Val
465 470 475 480

Leu Val Gly Ile Val Thr Leu Tyr Leu Gly Val Met Val Gln Ala
485 490 495

<210> SEQ ID NO 27
<211> LENGTH: 493
<212> TYPE: PRT
<213> ORGANISM: Flavivirus

<400> SEQUENCE: 27

Met Arg Cys Val Gly Val Gly Asn Arg Asp Phe Val Glu Gly Leu Ser
1 5 10 15

Gly Ala Thr Trp Val Asp Val Val Leu Glu His Gly Gly Cys Val Thr
20 25 30

Thr Met Ala Lys Asn Lys Pro Thr Leu Asp Ile Glu Leu Gln Lys Thr
35 40 45

Glu Ala Thr Gln Leu Ala Thr Leu Arg Lys Leu Cys Ile Glu Gly Lys
50 55 60

Ile Thr Asn Ile Thr Thr Asp Ser Arg Cys Pro Thr Gln Gly Glu Ala
65 70 75 80

Val Leu Pro Glu Glu Gln Asp Gln Asn Tyr Val Cys Lys His Thr Tyr
85 90 95

Val Asp Arg Gly Trp Gly Asn Gly Cys Gly Leu Phe Gly Lys Gly Ser
100 105 110

Leu Val Thr Cys Ala Lys Phe Gln Cys Leu Glu Pro Ile Glu Gly Lys
115 120 125

Val Val Gln Tyr Glu Asn Leu Lys Tyr Thr Val Ile Ile Thr Val His
130 135 140

Thr Gly Asp Gln His Gln Val Gly Asn Glu Thr Gln Gly Val Thr Ala
145 150 155 160

Glu Ile Thr Pro Gln Ala Ser Thr Thr Glu Ala Ile Leu Pro Glu Tyr
165 170 175

Gly Thr Leu Gly Leu Glu Cys Ser Pro Arg Thr Gly Leu Asp Phe Asn
180 185 190

Glu Met Ile Leu Leu Thr Met Lys Asn Lys Ala Trp Met Val His Arg
195 200 205

Gln Trp Phe Phe Asp Leu Pro Leu Pro Trp Thr Ser Gly Ala Thr Thr
210 215 220

Glu Thr Pro Thr Trp Asn Arg Lys Glu Leu Leu Val Thr Phe Lys Asn
225 230 235 240

Ala His Ala Lys Lys Gln Glu Val Val Val Leu Gly Ser Gln Glu Gly
245 250 255

Ala Met His Thr Ala Leu Thr Gly Ala Thr Glu Ile Gln Asn Ser Gly
260 265 270

Gly Thr Ser Ile Phe Ala Gly His Leu Lys Cys Arg Leu Lys Met Asp
275 280 285

Lys Leu Glu Leu Lys Gly Met Ser Tyr Ala Met Cys Thr Asn Thr Phe
290 295 300

Val Leu Lys Lys Glu Val Ser Glu Thr Gln His Gly Thr Ile Leu Ile
305 310 315 320

Lys Val Glu Tyr Lys Gly Glu Asp Ala Pro Cys Lys Ile Pro Phe Ser
325 330 335

Thr Glu Asp Glu Gln Gly Lys Ala His Asn Gly Arg Leu Ile Thr Ala
340 345 350

Asn Pro Val Val Thr Lys Lys Glu Glu Pro Val Asn Ile Glu Ala Glu
355 360 365

Pro Pro Phe Gly Glu Ser Asn Ile Val Ile Gly Ile Gly Asp Asn Ala
370 375 380

Leu Lys Ile Asn Trp Tyr Lys Lys Gly Ser Ser Ile Gly Lys Met Phe
385 390 395 400

Glu Ala Thr Ala Arg Gly Ala Arg Arg Met Ala Ile Leu Gly Asp Thr
405 410 415

Ala Trp Asp Phe Gly Ser Val Gly Gly Val Leu Asn Ser Leu Gly Lys
420 425 430

Met Val His Gln Ile Phe Gly Ser Ala Tyr Thr Ala Leu Phe Ser Gly
435 440 445

Val Ser Trp Val Met Lys Ile Gly Ile Gly Val Leu Leu Thr Trp Ile
450 455 460

Gly Leu Asn Ser Lys Asn Thr Ser Met Ser Phe Ser Cys Ile Ala Ile
465 470 475 480

Gly Ile Ile Thr Leu Tyr Leu Gly Ala Val Val Gln Ala
485 490

<210> SEQ ID NO 28
<211> LENGTH: 495
<212> TYPE: PRT
<213> ORGANISM: Flavivirus

<400> SEQUENCE: 28

Met Arg Cys Val Gly Val Gly Asn Arg Asp Phe Val Glu Gly Val Ser
1 5 10 15

Gly Gly Ala Trp Val Asp Leu Val Leu Glu His Gly Gly Cys Val Thr

-continued

```
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Ala Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
            340                 345                 350

Ser Ser Thr Pro Leu Ala Glu Asn Thr Asn Ser Ala Thr Asn Ile Glu
        355                 360                 365

Leu Glu Pro Pro Phe Gly Asp Ser Tyr Ile Val Ile Gly Val Gly Asn
    370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445
```

-continued

```
Gly Gly Val Ser Trp Met Ile Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495


<210> SEQ ID NO 29
<211> LENGTH: 500
<212> TYPE: PRT
<213> ORGANISM: Flavivirus

<400> SEQUENCE: 29

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Glu Val Gly Ile Phe Val His
    130                 135                 140

Gly Thr Thr Thr Ser Glu Asn His Gly Asn Tyr Ser Ala Gln Val Arg
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Pro Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
```

```
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
            420                 425                 430

Val Phe Asn Pro Ile Gly Lys Ala Ile His Gln Val Phe Gly Gly Ala
        435                 440                 445

Phe Arg Thr Ile Phe Gly Gly Met Ser Trp Ile Thr Gln Gly Leu Met
    450                 455                 460

Gly Ala Leu Leu Leu Trp Met Gly Val Asn Ala Arg Asp Arg Ser Ile
465                 470                 475                 480

Ala Leu Ala Phe Leu Ala Leu Gly Gly Val Leu Val Phe Leu Ala Thr
                485                 490                 495

His Val Gln Ala
            500


<210> SEQ ID NO 30
<211> LENGTH: 501
<212> TYPE: PRT
<213> ORGANISM: Flavivirus

<400> SEQUENCE: 30

Phe Asn Cys Leu Gly Thr Ser Asn Arg Asp Phe Val Glu Gly Ala Ser
1               5                   10                  15

Gly Ala Thr Trp Ile Asp Leu Val Leu Glu Gly Gly Ser Cys Val Thr
            20                  25                  30

Val Met Ala Pro Glu Lys Pro Thr Leu Asp Phe Lys Val Met Lys Met
        35                  40                  45

Glu Ala Thr Glu Leu Ala Thr Val Arg Glu Tyr Cys Tyr Glu Ala Thr
    50                  55                  60

Leu Asp Thr Leu Ser Thr Val Ala Arg Cys Pro Thr Thr Gly Glu Ala
65                  70                  75                  80

His Asn Thr Lys Arg Ser Asp Pro Thr Phe Val Cys Lys Arg Asp Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Thr Cys Lys Asn Lys Ala Thr Gly Lys
        115                 120                 125

Thr Ile Leu Arg Glu Asn Ile Lys Tyr Glu Val Ala Ile Phe Val His
    130                 135                 140

Gly Ser Thr Asp Ser Thr Ser His Gly Asn Tyr Ser Glu Gln Ile Gly
145                 150                 155                 160

Lys Asn Gln Ala Ala Arg Phe Thr Ile Ser Pro Gln Ala Pro Ser Phe
                165                 170                 175

Thr Ala Asn Met Gly Glu Tyr Gly Thr Val Thr Ile Asp Cys Glu Ala
            180                 185                 190
```

```
Arg Ser Gly Ile Asn Thr Glu Asp Tyr Tyr Val Phe Thr Val Lys Glu
        195                 200                 205

Lys Ser Trp Leu Val Asn Arg Asp Trp Phe His Asp Leu Asn Leu Pro
    210                 215                 220

Trp Thr Ser Pro Ala Thr Thr Asp Trp Arg Asn Arg Glu Thr Leu Val
225                 230                 235                 240

Glu Phe Glu Gly Pro His Ala Thr Lys Gln Thr Val Val Ala Leu Gly
                245                 250                 255

Ser Gln Glu Gly Ala Leu His Thr Ala Leu Ala Gly Ala Ile Pro Ala
            260                 265                 270

Thr Val Ser Ser Ser Thr Leu Thr Leu Gln Ser Gly His Leu Lys Cys
        275                 280                 285

Arg Ala Lys Leu Asp Lys Val Lys Ile Lys Gly Thr Thr Tyr Gly Met
    290                 295                 300

Cys Asp Ser Ala Val Thr Phe Ser Lys Asn Pro Thr Asp Thr Gly His
305                 310                 315                 320

Gly Thr Val Ile Val Glu Leu Gln Tyr Thr Gly Ser Asn Gly Pro Cys
                325                 330                 335

Arg Val Pro Ile Ser Val Thr Ala Asn Leu Ile Asp Leu Thr Pro Val
            340                 345                 350

Gly Arg Leu Val Thr Val Asn Pro Phe Ile Ser Thr Gly Gly Thr Asn
        355                 360                 365

Asn Lys Val Met Ile Glu Val Glu Pro Pro Phe Gly Asp Ser Tyr Ile
    370                 375                 380

Val Val Gly Arg Gly Thr Thr Gln Ile Asn Tyr His Trp His Lys Glu
385                 390                 395                 400

Gly Ser Ser Ile Gly Lys Ala Leu Ala Thr Thr Trp Lys Gly Ala Gln
                405                 410                 415

Arg Leu Ala Val Leu Gly Asp Thr Ala Trp Asp Phe Gly Ser Ile Gly
            420                 425                 430

Gly Val Phe Asn Ser Ile Gly Lys Ala Val His Gln Val Phe Gly Gly
        435                 440                 445

Ala Phe Arg Thr Leu Phe Gly Gly Met Ser Trp Ile Thr Gln Gly Leu
    450                 455                 460

Leu Gly Ala Leu Leu Leu Trp Met Gly Leu Gln Ala Arg Asp Arg Ser
465                 470                 475                 480

Ile Ser Leu Thr Leu Leu Ala Val Gly Gly Ile Leu Val Phe Leu Ala
                485                 490                 495

Thr Ser Val Gln Ala
            500


<210> SEQ ID NO 31
<211> LENGTH: 501
<212> TYPE: PRT
<213> ORGANISM: Flavivirus

<400> SEQUENCE: 31

Leu Asn Cys Leu Gly Ile Ser Asn Arg Asp Phe Val Glu Gly Leu Ser
1               5                   10                  15

Gly Gly Thr Trp Val Asp Ile Val Leu Glu Gly Gly Ser Cys Val Thr
            20                  25                  30

Val Met Ala Lys Asp Lys Pro Thr Leu Asp Ile Lys Leu Ile Arg Met
        35                  40                  45

Glu Ala Lys Asp Leu Ala Thr Val Arg Ser Tyr Cys Tyr Gln Ala Thr
    50                  55                  60
```

-continued

```
Val Thr Asp Ser Ser Thr Glu Ala Arg Cys Pro Thr Met Gly Glu Ala
65                  70                  75                  80

His Asn Ser Lys Ser Leu Asp Ala Ser Tyr Val Cys Lys Ser Ser Tyr
                85                  90                  95

Val Asp Arg Gly Trp Gly Asn Gly Cys Gly Leu Phe Gly Lys Gly Ser
            100                 105                 110

Ile Gln Thr Cys Val Lys Phe Ser Cys Pro Gly Lys Ala Thr Gly Lys
        115                 120                 125

Ser Ile Gln Arg Glu Asn Leu Asn Tyr Asp Val Ala Val Tyr Val His
    130                 135                 140

Gly Pro Ile Ser Ala Ala Ala His Gly Asn Tyr Thr Ala Gln Leu Thr
145                 150                 155                 160

Gly Lys Tyr Ala Ala Lys Phe Ser Ile Thr Pro Ser Ala Pro Thr Tyr
                165                 170                 175

Thr Ala Asn Leu Gly Glu Tyr Gly Glu Ala Thr Met Glu Cys Glu Pro
            180                 185                 190

Arg Ala Ala Leu Asp Ile Asp Asn Tyr Tyr Val Met Ser Leu Asn Asn
        195                 200                 205

Lys His Trp Leu Val Asn Arg Asp Trp Phe His Asp Leu Asp Leu Pro
    210                 215                 220

Trp Thr Gly Pro Ala Thr Glu Ser Trp Lys Asn Arg Glu Ser Leu Ile
225                 230                 235                 240

Glu Phe Glu Glu Pro His Ala Thr Arg Gln Thr Val Val Ala Leu Gly
                245                 250                 255

Asn Gln Glu Gly Ala Leu His Thr Ala Leu Ala Gly Ala Ile Pro Val
            260                 265                 270

Glu Val Ser Ser Thr Thr Leu Thr Leu Asn Ser Gly His Leu Lys Cys
        275                 280                 285

Arg Leu Lys Leu Asp Lys Leu Lys Ile Lys Gly Thr Thr Tyr Ala Met
    290                 295                 300

Cys Lys Gly Thr Phe Ala Phe Ala Gln Thr Pro Val Asp Thr Gly His
305                 310                 315                 320

Gly Thr Ile Val Ala Glu Leu Thr Tyr Thr Gly Thr Asp Gly Pro Cys
                325                 330                 335

Lys Ile Pro Ile Ser Met Thr Ala Asp Leu Arg Asp Met Thr Pro Ile
            340                 345                 350

Gly Arg Leu Val Thr Val Asn Pro Ile Ile Pro Ser Ser Ala Lys Ser
        355                 360                 365

Gln Lys Ile Leu Val Glu Leu Glu Pro Pro Phe Gly Ser Ser Phe Ile
    370                 375                 380

Leu Val Gly Gln Glu Asn Asn Gln Ile Lys Tyr Gln Trp His Lys Thr
385                 390                 395                 400

Gly Ser Thr Ile Gly Asn Ala Leu Lys Thr Thr Trp Lys Gly Ala Gln
                405                 410                 415

Arg Phe Ala Val Leu Gly Asp Thr Ala Trp Asp Phe Gly Ser Val Gly
            420                 425                 430

Gly Ile Phe Asn Ser Ile Gly Lys Thr Ile His Gly Val Phe Gly Thr
        435                 440                 445

Ala Phe Arg Ser Leu Phe Gly Gly Met Ser Trp Val Thr Gln Ala Leu
    450                 455                 460

Met Gly Ala Leu Leu Leu Trp Leu Gly Ile Ser Ala Arg Glu Arg Thr
465                 470                 475                 480
```

-continued

```
Val Ser Leu Ile Met Leu Ser Val Gly Gly Ile Leu Leu Phe Leu Ala
                485                 490                 495

Val Asn Val His Ala
            500


<210> SEQ ID NO 32
<211> LENGTH: 501
<212> TYPE: PRT
<213> ORGANISM: Flavivirus

<400> SEQUENCE: 32

Met Asn Cys Leu Gly Ile Ser Asn Arg Asp Phe Val Glu Gly Leu Ser
1               5                   10                  15

Gly Gly Thr Trp Val Asp Ile Val Leu Glu Gly Gly Ser Cys Val Thr
            20                  25                  30

Val Met Ala Lys Asp Lys Pro Thr Leu Asp Ile Lys Leu Ile Arg Met
        35                  40                  45

Glu Ala Lys Asp Leu Ala Thr Val Arg Ser Tyr Cys Tyr Gln Ala Thr
    50                  55                  60

Val Thr Asp Ser Ser Thr Glu Ala Arg Cys Pro Thr Met Gly Glu Ala
65                  70                  75                  80

His Asn Ser Lys Ser Leu Asp Ala Ser Tyr Val Cys Lys Ser Ser Tyr
                85                  90                  95

Val Asp Arg Gly Trp Gly Asn Gly Cys Gly Leu Phe Gly Lys Gly Ser
            100                 105                 110

Ile Gln Thr Cys Val Lys Phe Ser Cys Pro Gly Lys Ala Thr Gly Lys
        115                 120                 125

Ser Ile Gln Arg Glu Asn Leu Asn Tyr Asp Val Ala Val Tyr Val His
    130                 135                 140

Gly Pro Thr Ser Ala Ala Ala His Gly Asn Tyr Thr Ala Gln Leu Thr
145                 150                 155                 160

Gly Lys Tyr Ala Ala Lys Phe Ser Ile Thr Pro Ser Ala Pro Thr Tyr
                165                 170                 175

Thr Ala Asn Leu Gly Glu Tyr Gly Glu Ala Thr Met Glu Cys Glu Pro
            180                 185                 190

Arg Ala Ala Leu Asp Ile Asp Asn Tyr Tyr Val Met Ser Leu Asn Asn
        195                 200                 205

Lys His Trp Leu Val Asn Arg Asp Trp Phe His Asp Leu Asp Leu Pro
    210                 215                 220

Trp Thr Gly Pro Ala Thr Glu Ser Trp Lys Asn Arg Glu Ser Leu Ile
225                 230                 235                 240

Glu Phe Glu Glu Pro His Ala Thr Arg Gln Thr Val Val Ala Leu Gly
                245                 250                 255

Asn Gln Glu Gly Ala Leu His Thr Ala Leu Ala Gly Ala Ile Pro Val
            260                 265                 270

Glu Val Ser Ser Thr Thr Leu Thr Leu Asn Ser Gly His Leu Lys Cys
        275                 280                 285

Arg Leu Lys Leu Asp Lys Leu Lys Ile Lys Gly Thr Thr Tyr Ala Met
    290                 295                 300

Cys Lys Gly Thr Phe Ala Phe Ala Gln Thr Pro Val Asp Thr Gly His
305                 310                 315                 320

Gly Thr Ile Val Ala Glu Leu Thr Tyr Thr Gly Thr Asp Gly Pro Cys
                325                 330                 335

Lys Ile Pro Ile Ser Met Thr Ala Asp Leu Arg Asp Met Thr Pro Ile
            340                 345                 350
```

```
Gly Arg Leu Val Thr Val Asn Pro Ile Ile Pro Ser Ser Ala Asn Ser
        355                 360                 365

Gln Lys Ile Leu Val Glu Leu Glu Pro Pro Phe Gly Ser Ser Phe Ile
    370                 375                 380

Leu Val Gly Gln Glu Ser Asn Gln Ile Lys Tyr Gln Trp His Lys Thr
385                 390                 395                 400

Gly Ser Thr Ile Gly Asn Ala Leu Lys Thr Thr Trp Lys Gly Ala Gln
                405                 410                 415

Arg Phe Ala Val Leu Gly Asp Thr Ala Trp Asp Phe Gly Ser Val Gly
            420                 425                 430

Gly Ile Phe Asn Ser Ile Gly Lys Thr Ile His Gly Val Phe Gly Thr
        435                 440                 445

Ala Phe Arg Ser Leu Phe Gly Gly Met Ser Trp Val Thr Gln Ala Leu
    450                 455                 460

Met Gly Ala Leu Leu Leu Trp Leu Gly Ile Ser Ala Arg Glu Arg Thr
465                 470                 475                 480

Val Ser Leu Ile Met Leu Ser Val Gly Gly Ile Leu Leu Phe Leu Ala
                485                 490                 495

Val Asn Val His Ala
            500


<210> SEQ ID NO 33
<211> LENGTH: 501
<212> TYPE: PRT
<213> ORGANISM: Flavivirus

<400> SEQUENCE: 33

Ile Asn Cys Leu Gly Val Thr Asn Arg Asp Phe Val Glu Gly Met Ser
1               5                   10                  15

Gly Gly Thr Trp Val Asp Ile Val Leu Glu Gly Asp Gly Cys Val Thr
            20                  25                  30

Ile Met Ala Lys Asp Lys Pro Thr Leu Asp Ile Arg Leu Leu Lys Met
        35                  40                  45

Glu Ala Lys Asp Leu Ala Thr Val Arg Ser Tyr Cys Tyr His Ala Thr
    50                  55                  60

Val Thr Ser Val Ser Ser Glu Ala Arg Cys Pro Thr Met Gly Glu Ala
65                  70                  75                  80

His Asn Pro Lys Ala Leu Asp Ser Asn Tyr Leu Cys Lys Ser Thr Tyr
                85                  90                  95

Val Asp Arg Gly Trp Gly Asn Gly Cys Gly Leu Phe Gly Lys Gly Ser
            100                 105                 110

Leu Gln Thr Cys Val Lys Phe Gly Cys Thr Gln Lys Ala Met Gly Met
        115                 120                 125

Thr Ile Gln Arg Glu Asn Leu Asp Tyr Glu Leu Ala Ile Tyr Val His
    130                 135                 140

Gly Pro Thr Ser Val Ala Ala His Gly Asn Tyr Thr Thr Gln Leu Gly
145                 150                 155                 160

Ala Lys His Ala Ala Lys Phe Ser Ile Thr Pro Ser Ser Pro Ser Phe
                165                 170                 175

Thr Ala Asn Leu Gly Glu Tyr Gly Glu Ala Thr Val Asp Cys Glu Pro
            180                 185                 190

Arg Ala Ala Leu Asp Ile Asp Asn Tyr Tyr Val Met Ser Met Asn Asn
        195                 200                 205

Lys His Trp Leu Val Asn Arg Asp Trp Phe His Asp Leu Asp Leu Pro
```

-continued

```
    210                 215                 220

Trp Thr Gly Pro Ala Thr Asp Val Trp Lys Tyr Arg Glu Ser Leu Val
225                 230                 235                 240

Glu Phe Glu Glu Ala His Val Thr Arg Gln Thr Val Val Ala Leu Ala
                245                 250                 255

Ala Gln Glu Gly Glu Leu His Ile Val Leu Ala Gly Ala Ile Pro Val
            260                 265                 270

Thr Val Ala Gly Thr Thr Leu Thr Leu Thr Ser Gly His Leu Lys Cys
        275                 280                 285

Arg Met Lys Leu Asp Lys Leu Lys Ile Lys Gly Ser Thr Tyr Leu Met
    290                 295                 300

Cys Lys Asp Lys Phe Ala Phe Ala Lys Asn Pro Val Asp Thr Gly His
305                 310                 315                 320

Gly Thr Ile Val Thr Glu Val Gln Tyr Ala Gly Ser Asp Gly Pro Cys
                325                 330                 335

Arg Ile Pro Ile Thr Met Thr Glu Asn Leu His Asp Leu Thr Pro Ile
            340                 345                 350

Gly Arg Leu Val Thr Val Asn Pro Phe Val Pro Ser Ser Glu Thr Ala
        355                 360                 365

Gln Lys Ile Leu Ile Glu Leu Glu Pro Pro Phe Gly Thr Ser Phe Ile
    370                 375                 380

Leu Val Gly Thr Gly Pro Asn Gln Val Lys Tyr Gln Trp His Lys Ser
385                 390                 395                 400

Gly Ser Val Ile Gly Ser Ala Phe Lys Thr Thr Ile Lys Gly Ala Gln
                405                 410                 415

Arg Met Ala Val Leu Gly Glu Thr Ala Trp Asp Phe Gly Ser Val Gly
            420                 425                 430

Gly Val Phe Asn Ser Ile Gly Lys Gly Ile His Gly Leu Phe Gly Gly
        435                 440                 445

Ala Phe Arg Thr Leu Phe Gly Gly Met Ser Trp Val Thr Gln Ala Leu
    450                 455                 460

Met Gly Ala Leu Leu Leu Trp Leu Gly Val Ser Ser Arg Glu Arg Thr
465                 470                 475                 480

Val Ser Ile Thr Leu Leu Ala Thr Gly Gly Ile Leu Leu Phe Leu Ala
                485                 490                 495

Met Asn Val His Ala
            500


<210> SEQ ID NO 34
<211> LENGTH: 501
<212> TYPE: PRT
<213> ORGANISM: Flavivirus

<400> SEQUENCE: 34

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80
```

-continued

```
His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Ala Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Gly Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
        355                 360                 365

Ala Lys Val Leu Ile Glu Leu Glu Pro Pro Phe Gly Asp Ser Tyr Ile
    370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Lys Gly Ala Gln
                405                 410                 415

Arg Leu Ala Ala Leu Gly Asp Thr Ala Trp Asp Phe Gly Ser Val Gly
            420                 425                 430

Gly Val Phe Thr Ser Val Gly Lys Ala Val His Gln Val Phe Gly Gly
        435                 440                 445

Ala Phe Arg Ser Leu Phe Gly Gly Met Ser Trp Ile Thr Gln Gly Leu
    450                 455                 460

Leu Gly Ala Leu Leu Leu Trp Met Gly Ile Asn Ala Arg Asp Arg Ser
465                 470                 475                 480

Ile Ala Leu Thr Phe Leu Ala Val Gly Gly Val Leu Leu Phe Leu Ser
                485                 490                 495

Val Asn Val His Ala
```

500

<210> SEQ ID NO 35
<211> LENGTH: 493
<212> TYPE: PRT
<213> ORGANISM: Flavivirus

<400> SEQUENCE: 35

Ala His Cys Ile Gly Ile Thr Asp Arg Asp Phe Ile Glu Gly Val His
1 5 10 15

Gly Gly Thr Trp Val Ser Ala Thr Leu Glu Gln Asp Lys Cys Val Thr
20 25 30

Val Met Ala Pro Asp Lys Pro Ser Leu Asp Ile Ser Leu Glu Thr Val
35 40 45

Ala Ile Asp Arg Pro Ala Glu Val Arg Lys Val Cys Tyr Asn Ala Val
50 55 60

Leu Thr His Val Lys Ile Asn Asp Lys Cys Pro Ser Thr Gly Glu Ala
65 70 75 80

His Leu Ala Glu Glu Asn Glu Gly Asp Asn Ala Cys Lys Arg Thr Tyr
85 90 95

Ser Asp Arg Gly Trp Gly Asn Gly Cys Gly Leu Phe Gly Lys Gly Ser
100 105 110

Ile Val Ala Cys Ala Lys Phe Thr Cys Ala Lys Ser Met Ser Leu Phe
115 120 125

Glu Val Asp Gln Thr Lys Ile Gln Tyr Val Ile Arg Ala Gln Leu His
130 135 140

Val Gly Ala Lys Gln Glu Asn Trp Asn Thr Asp Ile Lys Thr Leu Lys
145 150 155 160

Phe Asp Ala Leu Ser Gly Ser Gln Glu Val Glu Phe Thr Gly Tyr Gly
165 170 175

Lys Ala Thr Leu Glu Cys Gln Val Gln Thr Ala Val Asp Phe Gly Asn
180 185 190

Ser Tyr Ile Ala Glu Met Glu Thr Glu Ser Trp Ile Val Asp Arg Gln
195 200 205

Trp Ala Gln Asp Leu Thr Leu Pro Trp Gln Ser Gly Ser Gly Gly Val
210 215 220

Trp Arg Glu Met His His Leu Val Glu Phe Glu Pro Pro His Ala Val
225 230 235 240

Thr Ile Arg Val Leu Ala Leu Gly Asn Gln Glu Gly Ser Leu Lys Thr
245 250 255

Ala Leu Thr Gly Ala Met Arg Val Thr Lys Asp Thr Asn Asp Asn Asn
260 265 270

Leu Tyr Lys Leu His Gly Gly His Val Ser Cys Arg Val Lys Leu Ser
275 280 285

Ala Leu Thr Leu Lys Gly Thr Ser Tyr Lys Ile Cys Thr Asp Lys Met
290 295 300

Phe Phe Val Lys Asn Pro Thr Asp Thr Gly His Gly Thr Val Val Met
305 310 315 320

Gln Val Lys Val Ser Lys Gly Ala Pro Cys Arg Ile Pro Val Ile Val
325 330 335

Ala Asp Asp Leu Thr Ala Ala Ile Asn Lys Gly Ile Leu Val Thr Val
340 345 350

Asn Pro Ile Ala Ser Thr Asn Asp Asp Glu Val Leu Ile Glu Val Asn
355 360 365

```
Pro Pro Phe Gly Asp Ser Tyr Ile Ile Val Gly Arg Gly Asp Ser Arg
    370                 375                 380

Leu Thr Tyr Gln Trp His Lys Glu Gly Ser Ser Ile Gly Lys Leu Phe
385                 390                 395                 400

Thr Gln Thr Met Lys Gly Val Glu Arg Leu Ala Val Met Gly Asp Thr
                405                 410                 415

Ala Trp Asp Phe Ser Ser Ala Gly Gly Phe Phe Thr Ser Val Gly Lys
            420                 425                 430

Gly Ile His Thr Val Phe Gly Ser Ala Phe Gln Gly Leu Phe Gly Gly
        435                 440                 445

Leu Asn Trp Ile Thr Lys Val Ile Met Gly Ala Val Leu Ile Trp Val
    450                 455                 460

Gly Ile Asn Thr Arg Asn Met Thr Met Ser Met Ser Met Ile Leu Val
465                 470                 475                 480

Gly Val Ile Met Met Phe Leu Ser Leu Gly Val Gly Ala
                485                 490


<210> SEQ ID NO 36
<211> LENGTH: 485
<212> TYPE: PRT
<213> ORGANISM: Flavivirus

<400> SEQUENCE: 36

Ser Thr Cys Val Ser Val Ala Lys Arg Asp Met Ile Arg Gly Asp Leu
1               5                   10                  15

Gly Thr Thr Trp Val Asp Ala Phe Leu Glu Lys Gly Ser Cys Ser Thr
            20                  25                  30

Leu Met Val Glu Asp Lys Pro Ala Val Asp Val Trp Leu Asp Glu Val
        35                  40                  45

Ser Gln Ser Ser Val Ile Ala Ser His Glu Tyr Cys Met Glu Val Ala
    50                  55                  60

Gly Ser Asn Val Lys Ser Ser Gly Ser Cys Pro Thr Gln Gly Glu Ala
65                  70                  75                  80

His Leu Ala Glu Glu Ala Asn Ser Asp Tyr Val Cys Lys Arg Gly Phe
                85                  90                  95

Ser Asp Arg Gly Trp Gly Asn Gly Cys Gly Leu Phe Gly Lys Gly Ser
            100                 105                 110

Ile Val Ala Cys Ile Lys Thr Thr Cys Lys Asn Asp Ala Asn Ile Ile
        115                 120                 125

Lys Ser Tyr Val Tyr Asp Ala Pro Lys Ile Gln Phe Thr Val Gly Ile
    130                 135                 140

Glu Val His Lys Gly Asn Leu Leu Gly Pro Ser Asp Asn Asn Arg Ile
145                 150                 155                 160

Val Lys Ala Thr Phe Ser Ala Glu Ala Gly Lys His Ser Val Glu Leu
                165                 170                 175

Thr Gly Tyr Gly Val Leu Glu Phe Ser Cys Arg Val Val Ala Ser Thr
            180                 185                 190

Asp Leu Ser Asp Ile Arg Leu Ile Glu Ile Asp Asn His Phe Tyr Asn
        195                 200                 205

Val His Glu Asp Trp Leu Arg Asp Leu Pro Leu Pro Trp Arg Leu Pro
    210                 215                 220

Lys Gly Lys Trp Lys Asp Met Glu Arg Met Val Val Phe Lys Asp Pro
225                 230                 235                 240

His Ala Val Lys Trp Thr Val Gln Thr Tyr Gly Asn Gln Arg Thr Ala
                245                 250                 255
```

```
Ile Phe Lys Ala Leu Val Lys Ala Asn Glu Ile Ser Lys Ser Asn Asn
            260                 265                 270

Lys Tyr Ile Leu Asp Gly Gly His Leu Ser Cys Arg Ile Gly Val Asn
        275                 280                 285

Gly Leu Lys Met Val Gly Ala Thr Tyr Ser Gln Cys Thr Lys Pro Phe
    290                 295                 300

Glu Trp Ile Lys Lys Pro Val Leu Thr Gln His Gly Thr Val Val Met
305                 310                 315                 320

Glu Val Lys Tyr Thr Gly Glu Gly Ala Pro Cys Arg Ile Pro Phe Arg
                325                 330                 335

Val Glu Arg Val Asp Lys Pro Met Glu Asn Val Gly Asn Leu Val Thr
            340                 345                 350

Gly Asn Pro Tyr Ala Ser Gln Lys Asp Ala Val Val Phe Leu Glu Ala
        355                 360                 365

Glu Val Pro Pro Gly Ile Ser Ile Ile Lys Ile Gly Asp Ile Asp Val
    370                 375                 380

Gln Trp Asn Gln Pro Gly Met Thr Val Gly Lys Thr Ile Glu Leu Val
385                 390                 395                 400

Lys Arg Gly Leu Glu Arg Thr Leu Ile Ser Ser Ser Ala Phe Trp Asn
                405                 410                 415

Ser Asp Glu Pro Phe His Phe Ser Asn Leu Ile Ser Ile Ile Lys Ile
            420                 425                 430

Pro Phe Asp Phe Val Phe Gly Ser Leu Ser Phe Ile Thr Arg Leu Ile
        435                 440                 445

Leu Ser Val Val Leu Ile Trp Ile Cys Leu Asn Thr Arg Asn Gly Thr
    450                 455                 460

Met Ala Ala Ala Thr Gly Val Val Gly Phe Thr Leu Leu Ala Leu Thr
465                 470                 475                 480

Thr Gly Val Val Gly
                485


<210> SEQ ID NO 37
<211> LENGTH: 484
<212> TYPE: PRT
<213> ORGANISM: Flavivirus

<400> SEQUENCE: 37

Thr Asn Cys Val Ser Ile Gln Lys Arg Asp Ile Leu Arg Gly Ser Gly
1               5                   10                  15

Ser Thr Thr Trp Phe Asp Val Leu Leu Glu Lys Gly Ser Cys Val Thr
            20                  25                  30

Ile Val Ala Asp Asp Arg Pro Thr Val Asp Ile Trp Leu Asp Arg Ile
        35                  40                  45

Thr His Glu Ser Pro Ile Ala Gly Arg Glu Tyr Cys Met Arg Val Asp
    50                  55                  60

Ile Ser Gly Leu Lys Ile Ala Thr Arg Cys Pro Thr Leu Gly Glu Ala
65                  70                  75                  80

Tyr Leu Ser Glu Glu His Thr Glu Asp Tyr Val Cys Lys Arg Gly Phe
                85                  90                  95

Ser Asp Arg Gly Trp Gly Asn Gly Cys Gly Leu Phe Gly Lys Gly Ser
            100                 105                 110

Ile Val Gly Cys Val Lys Thr Thr Cys Lys Ser Ser Gly Ile Ala Lys
        115                 120                 125

Ser Tyr Ser Tyr Asp Ile Pro Lys Val Lys Tyr Val Ile Ser Thr Glu
```

-continued

```
    130                 135                 140

Val His Lys Gly Glu Leu Ile Ser Gly Asn Val Ser Ala Ser Val Val
145                 150                 155                 160

Ser Ala Thr Phe Ser Ser Glu Ala Glu Lys His Ser Met Glu Leu Glu
                165                 170                 175

Asp Tyr Gly Arg Leu Glu Phe Thr Cys Arg Val Val Ser Gly Ser Asn
            180                 185                 190

Leu Gly Ser Val Arg Ile Leu Glu Ile Asp Asn His Tyr Phe Asn Val
        195                 200                 205

His Glu Asp Trp Leu Leu Asp Leu Pro Leu Pro Trp Arg Ile Pro Asp
    210                 215                 220

Gly His Trp His Asp Leu Gly Lys Leu Ile Ala Phe Lys Glu Pro His
225                 230                 235                 240

Ala Val Lys Met Val Val Gln Ala Tyr Gly Asp Gln Arg Ala Ser Leu
                245                 250                 255

Leu Lys Ser Leu Val Lys Ala Glu Glu Ile Ala Lys Ser Gly Asn Ser
            260                 265                 270

Tyr Tyr Leu Pro Gly Gly His Val Asp Cys Arg Val Ser Leu Val Asn
        275                 280                 285

Leu Lys Leu Lys Gly Thr Thr Tyr Pro Tyr Cys Gly Asp Ser Phe Val
    290                 295                 300

Trp Lys Arg Arg Pro Thr Ala Thr His His Gly Thr Val Ala Met Glu
305                 310                 315                 320

Val Thr Tyr Gln Gly Thr Asp Val Pro Cys Lys Val Ser Val Ile Val
                325                 330                 335

Glu Lys Asp Gly Gln Asn Gly Gly Asn Ala Gly Ser Leu Ile Thr Ser
            340                 345                 350

Asn Pro Ile Ile Thr Ala Gln Gly Ser Ser Val Phe Leu Glu Leu Glu
        355                 360                 365

Val Pro Leu Gly Phe Ser Thr Ile Lys Val Gly Ala Ala Lys Gln Gln
    370                 375                 380

Trp Arg Gln Asp Gly Ser Ser Ile Gly Lys Ala Met Ala Arg Ala Ser
385                 390                 395                 400

Arg Ala Phe Glu Gln Thr Leu Met Thr Ala Gly Ser Tyr Trp Gln Ser
                405                 410                 415

Thr Asp Thr Val Thr Ser Phe Ser Leu Met Arg Met Ile Arg Ala Pro
            420                 425                 430

Leu Ala Met Leu Phe Gly Asp Val Gly Phe Met Gly Lys Met Ile Ile
        435                 440                 445

Ser Ile Val Cys Ile Trp Phe Ala Met Asn Ser Arg Asn Met Thr Leu
    450                 455                 460

Ser Leu Val Leu Gly Val Leu Gly Phe Gly Leu Leu Ala Phe Thr Thr
465                 470                 475                 480

Gly Val Met Gly


<210> SEQ ID NO 38
<211> LENGTH: 482
<212> TYPE: PRT
<213> ORGANISM: Flavivirus

<400> SEQUENCE: 38

Thr Asn Cys Val Thr Ile Ser Gln Arg Glu Ile Leu Lys Gly Val Glu
1               5                   10                  15

Gly Val Thr Trp Phe Glu Val Leu Leu Glu Lys Thr Ser Cys Ile Thr
```

-continued

```
            20                  25                  30

Ile Ala Ala Gln Asn Arg Pro Ser Ile Asp Leu Trp Leu Asp Asp Val
        35                  40                  45

Lys Gln Ser Ser Val Met Ala Ser Lys Glu Phe Cys Met Lys Val Glu
    50                  55                  60

Val Ser Glu Thr Gln Ile Ala Ala Arg Cys Pro Thr Gln Gly Asp Ala
65                  70                  75                  80

Thr Leu Pro Met Glu Gly Lys Asp Asp Tyr Val Cys Lys Lys Thr Phe
                85                  90                  95

Ser Asp Arg Gly Trp Gly Asn Gly Cys Ala Leu Phe Gly Lys Gly Ser
            100                 105                 110

Ile Val Gly Cys Ala Lys Val Ala Cys Asn Thr Ala Asn Val Met Lys
        115                 120                 125

Thr His Ile Tyr Glu Gln Gln Ala Val Gln Tyr Val Val Gly Ile Glu
    130                 135                 140

Val His Arg Gly Glu Val Ile Lys Ala Asn Val Ser Asp Lys Val Ile
145                 150                 155                 160

Lys Ala Ser Phe Ser Ala Glu Ala Glu Lys His Thr Val Glu Ile Pro
                165                 170                 175

Asp Tyr Gly Ser Leu Asp Phe Thr Cys Arg Val Val Ala Ser Ala Asp
            180                 185                 190

Leu Ser Asn Ile Arg Leu Leu Glu Val Asp Gly His Tyr Phe Asn Val
        195                 200                 205

His Glu Asp Trp Leu Asp Asp Leu Pro Leu Pro Trp Arg Ile Asn Ala
    210                 215                 220

Gly Pro Trp Arg Gly Met Asp Lys Leu Val Asn Phe Arg Glu Pro Tyr
225                 230                 235                 240

Ala Val Lys Met Val Ile Met Gly Tyr Gly Asp Gln Arg Pro Ala Val
                245                 250                 255

Leu Gly Ala Leu Asp Lys Ala Glu Glu Ile Lys Lys Val Gly Asp Asn
            260                 265                 270

Tyr His Leu Asn Gly Gly His Val Ser Cys Lys Val Ser Val Ala Lys
        275                 280                 285

Leu Lys Leu Lys Gly Met Thr Tyr Val Val Cys Gly Gly Lys Phe Ala
    290                 295                 300

Trp Ala Lys Lys Pro Ile Ala Thr Asn His Asp Thr Val Ala Met Glu
305                 310                 315                 320

Val Thr Tyr Thr Gly Asn Asp Thr Pro Cys Arg Val Thr Val Lys Asn
                325                 330                 335

Val Lys Glu Asn Ser Asp Asp Gln Gly Thr Leu Ile Thr Thr Asn Pro
            340                 345                 350

Phe Val Glu Ser Asn Gly Ala Thr Ile Phe Leu Glu Leu Glu Pro Val
        355                 360                 365

Tyr Gly Leu Ser Thr Ile Lys Val Gly Asp Ile Thr Tyr Gln Trp Asn
    370                 375                 380

Gln Gln Gly Ser Val Ile Gly Lys Ala Val Arg Lys Ile Thr Asn Asp
385                 390                 395                 400

Ile His Lys Thr Ile Val Val Gly Ser Ala Phe Trp Asn Ser Asp Gln
                405                 410                 415

Arg Phe Ser Ala Ile Asn Leu Met Asp Leu Ile Arg Leu Pro Phe Ala
            420                 425                 430

Phe Leu Phe Gly Gly Leu Gly Phe Met Met Lys Met Ile Ile Ser Leu
        435                 440                 445
```

Val Leu Ile Trp Phe Cys Leu Asn Thr Arg Asn Phe Ser Ile Ala Val
450 455 460

Thr Ser Gly Ile Val Gly Phe Gly Leu Leu Ala Phe Thr Thr Gly Val
465 470 475 480

Met Gly

<210> SEQ ID NO 39
<211> LENGTH: 484
<212> TYPE: PRT
<213> ORGANISM: Flavivirus

<400> SEQUENCE: 39

Thr Gln Cys Val Asn Ile Gln Lys Arg Asp Ile Ile Arg Gly Ala Ser
1 5 10 15

Asp Val Ser Trp Phe Asp Val Leu Leu Glu Lys Gly Ala Cys Val Thr
20 25 30

Ile Ser Ala Gln Asp Lys Pro Ser Val Asp Leu Trp Leu Asp Asp Val
35 40 45

Ile Gln Glu Ser Leu Ile Glu Gly Arg His Tyr Cys Thr Lys Ala Ser
50 55 60

Ile Thr Asp Leu Lys Ala Asp Ala Arg Cys Pro Thr Gln Gly Glu Ala
65 70 75 80

Thr Met Arg Glu Glu His Leu Asp Gly Tyr Val Cys Lys Arg Ser Phe
85 90 95

Ser Asp Arg Gly Trp Gly Asn Gly Cys Gly Leu Phe Gly Lys Gly Ser
100 105 110

Ile Val Gly Cys Ala Lys Ala Thr Cys Gly Ala Asn Asp Ile Ile Lys
115 120 125

Ser Tyr Ser Tyr Asp Ser Pro Lys Val Lys Tyr Val Ile Gly Ala Glu
130 135 140

Val His Gln Gly Lys Leu Leu Thr Asn Asn Ser Thr Asp Arg Ile Val
145 150 155 160

Lys Thr Thr Leu Thr Ala Glu Ser Glu Lys His Thr Ile Thr Ile Ala
165 170 175

Asp Tyr Gly Ser Met Asp Phe Thr Cys Arg Val Val Ala Ser Ala Glu
180 185 190

Leu Ser Asn Ile Arg Met Ile Glu Leu Asp Gly His Met Phe Asn Val
195 200 205

His Glu Asp Trp Leu Ser Asp Leu Pro Leu Pro Ser Lys Ile Ser Gly
210 215 220

Gly Ser Trp His Gly Met Asp Arg Leu Val Val Phe Lys Glu Pro His
225 230 235 240

Ala Val Lys Met Glu Ile Gln Glu Cys Gly Asp Gln Arg Pro Ala Val
245 250 255

Phe Lys Ser Leu Val Lys Ala Glu Glu Val Thr Lys Thr Ser Asn Ser
260 265 270

Tyr His Leu Thr Gly Gly His Val Asp Cys Arg Val Ser Thr Leu Asn
275 280 285

Leu Arg Met Lys Gly Leu Thr Tyr Gln Met Cys Ser Ser Ser Phe Val
290 295 300

Trp His Lys Arg Pro Val Ala Thr Gln His Gly Thr Val Ala Met Glu
305 310 315 320

Val Lys Tyr Lys Gly Ser Asp Ala Pro Cys Arg Ile Pro Val Ser Val
325 330 335

```
Glu Lys Glu Gly Tyr Asn Gly Lys Asn Phe Gly Asn Leu Ile Thr Ala
            340                 345                 350

Asn Pro Phe Ala Ala Asn Asn Glu Ala Val Val Phe Leu Glu Leu Glu
        355                 360                 365

Ala Pro Leu Gly Val Ser Thr Ile Lys Val Gly Gly Ala Val Phe Gln
    370                 375                 380

Trp Lys Gln Glu Gly Ser Ser Ile Gly Lys Ala Val Thr Leu Met Lys
385                 390                 395                 400

Arg Asn Ile Glu Lys Thr Leu Ile Thr Ser Ser Ala Tyr Trp Ser Ser
                405                 410                 415

Ser Glu Pro Phe Thr Ser Ala Gly Ile Met Arg Ile Leu Arg Met Pro
            420                 425                 430

Phe Asp Met Ile Phe Gly Gly Val Gly Phe Leu Gly Lys Leu Met Ile
        435                 440                 445

Ser Gly Val Leu Ile Trp Leu Cys Val Asn Val Gln Asn Ser Thr Leu
    450                 455                 460

Ser Val Val Ser Gly Val Ile Gly Phe Met Leu Leu Gly Phe Thr Thr
465                 470                 475                 480

Gly Val Met Gly


<210> SEQ ID NO 40
<211> LENGTH: 182
<212> TYPE: PRT
<213> ORGANISM: Flavivirus

<400> SEQUENCE: 40

Ser Glu Leu Val Phe Ser Gly Gln Gly Thr Arg Thr Glu Arg Asn Arg
1               5                   10                  15

Pro Phe Glu Ile Lys Asp Gly Ala Tyr Arg Ile Tyr Ser Pro Gly Leu
            20                  25                  30

Leu Trp Gly His Arg Gln Ile Gly Val Gly Tyr Gly Ala Lys Gly Val
        35                  40                  45

Leu His Thr Met Trp His Val Thr Arg Gly Ala Ala Leu Val Val Glu
    50                  55                  60

Glu Ala Ile Ser Gly Pro Tyr Trp Ala Asp Val Arg Glu Asp Val Val
65                  70                  75                  80

Cys Tyr Gly Gly Ala Trp Ser Leu Glu Ser Arg Trp Arg Gly Glu Thr
                85                  90                  95

Val Gln Val His Ala Phe Pro Pro Gly Arg Pro Gln Glu Thr His Gln
            100                 105                 110

Cys Gln Pro Gly Glu Leu Ile Leu Glu Asn Gly Arg Lys Leu Gly Ala
        115                 120                 125

Val Pro Ile Asp Leu Ser Lys Gly Thr Ser Gly Ser Pro Ile Ile Asn
    130                 135                 140

Ala Gln Gly Glu Val Val Gly Leu Tyr Gly Asn Gly Leu Lys Thr Asn
145                 150                 155                 160

Glu Ala Tyr Val Ser Ser Ile Ala Gln Gly Glu Ala Glu Lys Ser Arg
                165                 170                 175

Pro Glu Leu Pro Leu Ser
            180


<210> SEQ ID NO 41
<211> LENGTH: 182
<212> TYPE: PRT
<213> ORGANISM: Flavivirus
```

<400> SEQUENCE: 41

Thr Asp Leu Val Phe Ser Gly Gln Leu Ser Asp His Gly Glu Ser Arg
1               5                   10                  15

Pro Phe Asp Ile Lys Asp Gly Val Tyr Arg Ile Tyr Ala Pro Gly Leu
            20                  25                  30

Leu Trp Gly His Arg Gln Ile Gly Val Gly Tyr Gly Thr Lys Gly Val
        35                  40                  45

Leu His Thr Met Trp His Val Thr Arg Gly Ala Ala Leu Ser Val Glu
    50                  55                  60

Gly Ala Val Ser Gly Pro Tyr Trp Ala Asp Val Arg Glu Asp Val Val
65                  70                  75                  80

Cys Tyr Gly Gly Ala Trp Ser Leu Glu Gly Lys Trp Gly Gly Glu Val
                85                  90                  95

Val Gln Val His Ala Phe Pro Pro Asp Ser Gly His Lys Val His Gln
            100                 105                 110

Cys Gln Pro Gly Lys Leu Asn Leu Glu Gly Gly Arg Val Met Gly Ala
        115                 120                 125

Ile Pro Ile Asp Leu Pro Arg Gly Thr Ser Gly Ser Pro Ile Ile Asn
    130                 135                 140

Ala Gln Gly Ile Val Leu Gly Leu Tyr Gly Asn Gly Leu Lys Ser Asn
145                 150                 155                 160

Asp Val Tyr Ile Ser Ser Ile Ala Gln Gly Ser Val Glu Lys Ser Arg
                165                 170                 175

Pro Asp Met Pro Leu Ala
            180

<210> SEQ ID NO 42
<211> LENGTH: 182
<212> TYPE: PRT
<213> ORGANISM: Flavivirus

<400> SEQUENCE: 42

Ser Asp Leu Val Phe Ser Gly Gln Gly Ser Arg Glu Arg Gly Asp Arg
1               5                   10                  15

Pro Phe Glu Val Lys Asp Gly Val Tyr Arg Ile Phe Ser Pro Gly Leu
            20                  25                  30

Leu Trp Gly Gln Arg Gln Val Gly Val Gly Tyr Gly Ser Arg Gly Val
        35                  40                  45

Leu His Thr Met Trp His Val Thr Arg Gly Ala Ala Leu Ser Ile Asp
    50                  55                  60

Asp Ala Val Ala Gly Pro Tyr Trp Ala Asp Val Arg Glu Asp Val Val
65                  70                  75                  80

Cys Tyr Gly Gly Ala Trp Ser Leu Glu Glu Lys Trp Lys Gly Glu Ala
                85                  90                  95

Val Gln Ile His Ala Phe Pro Pro Gly Arg Ala His Glu Val His Gln
            100                 105                 110

Cys Gln Pro Gly Glu Leu Ile Leu Asp Thr Gly Lys Arg Leu Gly Ala
        115                 120                 125

Val Pro Ile Asp Leu Ala Lys Gly Thr Ser Gly Ser Pro Ile Leu Asn
    130                 135                 140

Ala His Gly Val Val Val Gly Leu Tyr Gly Asn Gly Leu Lys Thr Asn
145                 150                 155                 160

Glu Thr Tyr Val Ser Ser Ile Ala Gln Gly Glu Val Glu Lys Ser Arg
                165                 170                 175

Pro Asn Leu Pro Gln Ala
180

<210> SEQ ID NO 43
<211> LENGTH: 182
<212> TYPE: PRT
<213> ORGANISM: Flavivirus

<400> SEQUENCE: 43

Gly Asp Leu Val Phe Ser Gly Leu Ala Ser Thr Pro Glu Ala Val Ala
1 5 10 15

Ala Trp Glu Val Arg Asp Gly Val Tyr Arg Ile Tyr Gln Pro Gly Leu
20 25 30

Leu Trp Gly Gln Arg Gln Ile Gly Val Gly Tyr Gly Gln Arg Gly Val
35 40 45

Leu His Thr Met Trp His Val Thr Arg Gly Ala Ala Ile Asn Ile Asn
50 55 60

Gly Ser Ile Ser Gly Pro Phe Trp Ala Asp Val Arg Glu Asp Val Val
65 70 75 80

Cys Tyr Gly Gly Gln Trp Ser Leu Pro Gly Arg Trp Glu Gly Glu Val
85 90 95

Val Gln Val His Ala Phe Pro Pro Gly Gly Ala His Glu Ile His Gln
100 105 110

Cys Arg Pro Gly Lys Met Thr Leu Glu Arg Gly Gln Thr Met Gly Ala
115 120 125

Ile Pro Ile Asp Leu Pro Arg Gly Thr Ser Gly Ser Pro Ile Ile Asn
130 135 140

Ala Gln Gly Ile Val Leu Gly Leu Tyr Gly Asn Gly Leu Arg Cys Asn
145 150 155 160

Asp Thr Tyr Val Ser Gly Ile Ala Gln Gly Ser Val Glu Lys Ser Arg
165 170 175

Pro Asp Leu Pro Pro Val
180

<210> SEQ ID NO 44
<211> LENGTH: 182
<212> TYPE: PRT
<213> ORGANISM: Flavivirus

<400> SEQUENCE: 44

Ser Glu Leu Val Phe Ser Gly Gln Glu Thr Arg Thr Glu Arg Asn Arg
1 5 10 15

Pro Phe Glu Ile Lys Asp Gly Ala Tyr Arg Ile Tyr Ser Pro Gly Leu
20 25 30

Leu Trp Gly His Arg Gln Ile Gly Val Gly Tyr Gly Ala Lys Gly Val
35 40 45

Leu His Thr Met Trp His Val Thr Arg Gly Ala Ala Leu Val Val Asp
50 55 60

Glu Ala Ile Ser Gly Pro Tyr Trp Ala Asp Val Arg Glu Asp Val Val
65 70 75 80

Cys Tyr Gly Gly Ala Trp Ser Leu Glu Ser Arg Trp Arg Gly Glu Thr
85 90 95

Val Gln Val His Ala Phe Pro Pro Gly Arg Pro Gln Glu Thr His Gln
100 105 110

Cys Gln Pro Gly Glu Leu Ile Leu Glu Asn Gly Arg Lys Leu Gly Ala
115 120 125

Val Pro Ile Asp Leu Ser Lys Gly Thr Ser Gly Ser Pro Ile Ile Asn
    130                 135                 140

Ala Gln Gly Glu Val Val Gly Leu Tyr Gly Asn Gly Leu Lys Thr Asn
145                 150                 155                 160

Glu Ala Tyr Val Ser Ser Ile Ala Gln Gly Glu Ala Glu Lys Ser Arg
                165                 170                 175

Pro Glu Ile Pro Leu Ser
            180

<210> SEQ ID NO 45
<211> LENGTH: 181
<212> TYPE: PRT
<213> ORGANISM: Flavivirus

<400> SEQUENCE: 45

Gly Glu Leu Val Phe Ser Gly Val Gly Gly Arg Thr Glu Asn Ala Pro
1               5                   10                  15

Phe Glu Val Lys Asp Gly Val Tyr Arg Ile Phe Arg Pro Gly Leu Phe
            20                  25                  30

Trp Gly Ala Ser Gln Ile Gly Val Gly Tyr Gly Ser His Gly Val Leu
        35                  40                  45

His Thr Met Trp His Val Thr Arg Gly Ala Ala Val Ser Ile Asn Gly
    50                  55                  60

Gly Ala Val Gly Pro Tyr Trp Ala Asp Ile Arg Glu Asp Val Val Cys
65                  70                  75                  80

Tyr Gly Gly Ala Trp Asn Leu Pro Thr Lys Trp Glu Gly Glu Val Val
                85                  90                  95

Gln Leu His Ala Phe Pro Pro Gly Arg Ala His Glu Ile Lys Gln Cys
            100                 105                 110

Gln Pro Gly Arg Leu Asn Leu Gly Asn Gly Arg Val Met Gly Ala Ile
        115                 120                 125

Pro Phe Asp Leu Pro Lys Gly Thr Ser Gly Ser Pro Ile Leu Asn Ala
    130                 135                 140

Gln Gly Val Val Val Gly Leu Tyr Gly Asn Gly Leu Lys Thr Lys Asp
145                 150                 155                 160

Thr Tyr Val Ser Gly Ile Ala Gln Gly Thr Pro Glu Val Ser Gly His
                165                 170                 175

Glu Met Pro Leu Val
            180

<210> SEQ ID NO 46
<211> LENGTH: 182
<212> TYPE: PRT
<213> ORGANISM: Flavivirus

<400> SEQUENCE: 46

Thr Asp Leu Val Phe Ser Gly Cys Ser Glu Gly Arg Ser Asp Ser Arg
1               5                   10                  15

Pro Leu Asp Val Lys Asn Gly Val Tyr Arg Ile Tyr Thr Pro Gly Leu
            20                  25                  30

Leu Trp Gly Gln Arg Gln Ile Gly Val Gly Tyr Gly Ala Lys Gly Val
        35                  40                  45

Leu His Thr Met Trp His Val Thr Arg Gly Ala Ala Leu Leu Val Asp
    50                  55                  60

Gly Val Ala Val Gly Pro Tyr Trp Ala Asp Val Arg Glu Asp Val Val
65                  70                  75                  80

Cys Tyr Gly Gly Ala Trp Ser Leu Glu Ser Arg Trp Arg Gly Glu Thr
85 90 95

Val Gln Val His Ala Phe Pro Pro Gly Arg Ala His Glu Thr His Gln
100 105 110

Cys Gln Pro Gly Glu Leu Ile Leu Glu Asn Gly Arg Lys Met Gly Ala
115 120 125

Ile Pro Ile Asp Leu Ala Lys Gly Thr Ser Gly Ser Pro Ile Met Asn
130 135 140

Ser Gln Gly Glu Val Val Gly Leu Tyr Gly Asn Gly Leu Lys Thr Asn
145 150 155 160

Asp Thr Tyr Val Ser Ser Ile Ala Gln Gly Glu Val Glu Lys Ser Arg
165 170 175

Pro Asn Leu Pro Gln Ser
180

<210> SEQ ID NO 47
<211> LENGTH: 182
<212> TYPE: PRT
<213> ORGANISM: Flavivirus

<400> SEQUENCE: 47

Ser Asp Leu Val Tyr Ser Gly Gln Gly Gly Gln Glu Arg Gly Asp Arg
1 5 10 15

Pro Phe Glu Val Lys Asp Gly Val Tyr Arg Ile Phe Ser Pro Gly Leu
20 25 30

Phe Trp Gly Gln Arg Gln Val Gly Val Gly Tyr Gly His Lys Gly Val
35 40 45

Leu His Thr Met Trp His Val Thr Arg Gly Ala Ala Leu Ser Ile Asp
50 55 60

Asp Ala Val Ala Gly Pro Tyr Trp Ala Asp Val Lys Glu Asp Val Val
65 70 75 80

Cys Tyr Gly Gly Ala Trp Ser Leu Glu Glu Lys Trp Lys Gly Glu Thr
85 90 95

Val Gln Val His Ala Phe Pro Pro Gly Arg Ala His Glu Val His Gln
100 105 110

Cys Gln Pro Gly Glu Leu Ile Leu Asp Thr Gly Lys Arg Leu Gly Ala
115 120 125

Ile Pro Ile Asp Leu Ala Lys Gly Thr Ser Gly Ser Pro Ile Leu Asn
130 135 140

Ala Gln Gly Val Val Val Gly Leu Tyr Gly Asn Gly Pro Lys Thr Asn
145 150 155 160

Glu Ser Tyr Val Ser Ser Ile Ala Gln Gly Glu Ala Glu Lys Ser Arg
165 170 175

Pro Asn Leu Pro Gln Ala
180

<210> SEQ ID NO 48
<211> LENGTH: 182
<212> TYPE: PRT
<213> ORGANISM: Flavivirus

<400> SEQUENCE: 48

Ser Asp Leu Val Phe Ser Gly Gln Ser Gly Ser Glu Arg Gly Ser Gln
1 5 10 15

Pro Phe Glu Val Arg Asp Gly Val Tyr Arg Ile Leu Ser Pro Gly Leu
20 25 30

Leu Trp Gly His Arg Gln Val Gly Val Gly Phe Gly Ser Lys Gly Val
35 40 45

Leu His Thr Met Trp His Val Thr Arg Gly Ala Ala Ile Phe Ile Asp
50 55 60

Asn Ala Val Ala Gly Pro Tyr Trp Ala Asp Val Lys Glu Asp Val Val
65 70 75 80

Cys Tyr Gly Gly Ala Trp Ser Leu Glu Glu Lys Trp Lys Gly Glu Lys
85 90 95

Val Gln Val His Ala Phe Pro Pro Gly Arg Ala His Glu Val His Gln
100 105 110

Cys Gln Pro Gly Glu Leu Val Leu Asp Thr Gly Arg Arg Ile Gly Ala
115 120 125

Ile Pro Ile Asp Leu Ala Lys Gly Thr Ser Gly Ser Pro Ile Leu Asn
130 135 140

Ala Gln Gly Ala Val Val Gly Leu Tyr Gly Asn Gly Leu Arg Thr Asn
145 150 155 160

Glu Thr Tyr Val Ser Ser Ile Ala Gln Gly Glu Val Glu Lys Ser Arg
165 170 175

Pro Asn Leu Pro Gln Ala
180

<210> SEQ ID NO 49
<211> LENGTH: 182
<212> TYPE: PRT
<213> ORGANISM: Flavivirus

<400> SEQUENCE: 49

Thr Asp Leu Val Phe Ser Gly Gln Leu Pro Asp Gln Gly Glu Lys Arg
1 5 10 15

Ser Phe Asp Ile Lys Glu Gly Val Tyr Arg Ile Tyr Ala Pro Gly Leu
20 25 30

Phe Trp Gly Tyr Arg Gln Ile Gly Val Gly Tyr Gly Thr Lys Gly Val
35 40 45

Leu His Thr Met Trp His Val Thr Arg Gly Ala Ala Leu Ser Val Glu
50 55 60

Gly Ala Thr Ser Gly Pro Tyr Trp Ala Asp Val Arg Glu Asp Val Val
65 70 75 80

Cys Tyr Gly Gly Ala Trp Gly Leu Asp Lys Lys Trp Gly Gly Glu Val
85 90 95

Val Gln Val His Ala Phe Pro Pro Asp Ser Gly His Lys Ile His Gln
100 105 110

Cys Gln Pro Gly Lys Leu Asn Leu Glu Gly Gly Arg Val Leu Gly Ala
115 120 125

Ile Pro Ile Asp Leu Pro Arg Gly Thr Ser Gly Ser Pro Ile Ile Asn
130 135 140

Ala Gln Gly Asp Val Leu Gly Leu Tyr Gly Asn Gly Leu Lys Ser Asn
145 150 155 160

Asp Val Tyr Ile Ser Ser Ile Ala Gln Gly Asn Val Glu Lys Ser Arg
165 170 175

Pro Glu Met Pro Leu Ala
180

<210> SEQ ID NO 50
<211> LENGTH: 183
<212> TYPE: PRT

<213> ORGANISM: Flavivirus

<400> SEQUENCE: 50

Gly Asp Leu Val Phe Ser Gly Val Pro Glu Ala Leu Val Arg Gly Asn
1 5 10 15

Ala Pro Phe Glu Val Lys Glu Gly Val Tyr Arg Ile Phe Arg Pro Gly
20 25 30

Leu Leu Trp Gly His Asn Gln Ile Gly Val Gly Tyr Gly Lys Gln Gly
35 40 45

Val Leu His Thr Met Trp His Val Thr Arg Gly Ala Ala Ile Arg Ile
50 55 60

Gly Asp Gly Val Cys Gly Pro His Trp Ala Asp Val Arg Glu Asp Val
65 70 75 80

Val Ser Tyr Gly Gly Pro Trp His Leu Ala Ser Arg Trp Lys Gly Glu
85 90 95

Val Val Gln Leu His Ala Phe Pro Pro Gly Arg Ala His Glu Val His
100 105 110

Gln Cys Gln Pro Gly Arg Leu Lys Leu Glu Asn Gly Lys Cys Ile Gly
115 120 125

Ala Ile Pro Ile Asp Met Pro Lys Gly Thr Ser Gly Ser Pro Ile Leu
130 135 140

Asn Val Asp Gly Asp Val Val Gly Leu Tyr Gly Asn Gly Leu Arg Thr
145 150 155 160

Asn Asp Thr Tyr Val Ser Gly Ile Ser Gln Gly Ser Ala Glu Lys Ser
165 170 175

Lys Leu Glu Met Pro Leu Ala
180

<210> SEQ ID NO 51
<211> LENGTH: 182
<212> TYPE: PRT
<213> ORGANISM: Flavivirus

<400> SEQUENCE: 51

Ser Asp Leu Val Tyr Ser Gly Gln Gly Gly Arg Glu Arg Gly Asp Arg
1 5 10 15

Pro Phe Glu Val Lys Asp Gly Val Tyr Arg Ile Phe Ser Pro Gly Leu
20 25 30

Leu Trp Gly Gln Arg Gln Val Gly Val Gly Tyr Gly Cys Arg Gly Val
35 40 45

Leu His Thr Met Trp His Val Thr Arg Gly Ala Ala Leu Ser Ile Asp
50 55 60

Asp Ala Val Thr Gly Pro Tyr Trp Ala Asp Val Arg Glu Asp Val Val
65 70 75 80

Cys Tyr Gly Gly Ala Trp Ser Leu Glu Glu Lys Trp Lys Gly Glu Thr
85 90 95

Val Gln Val His Ala Phe Pro Pro Gly Arg Ala His Glu Val His Gln
100 105 110

Cys Arg Pro Gly Glu Leu Ile Leu Asp Thr Gly Lys Arg Leu Gly Ala
115 120 125

Ile Pro Ile Asp Leu Ala Lys Gly Thr Ser Gly Ser Pro Ile Leu Asn
130 135 140

Ala Gln Gly Ala Val Val Gly Leu Tyr Gly Asn Gly Leu Lys Thr Asn
145 150 155 160

Glu Ser Tyr Val Ser Ser Ile Ala Gln Gly Glu Ala Glu Lys Ser Arg

```
                165                 170                 175

Pro Asn Leu Pro Gln Ala
            180


<210> SEQ ID NO 52
<211> LENGTH: 182
<212> TYPE: PRT
<213> ORGANISM: Flavivirus

<400> SEQUENCE: 52

Ser Asp Leu Val Phe Ser Gly Gln Gly Gly Arg Glu Arg Gly Asp Arg
1               5                   10                  15

Pro Phe Glu Val Lys Asp Gly Val Tyr Arg Ile Phe Ser Pro Gly Leu
            20                  25                  30

Phe Trp Gly Gln Asn Gln Val Gly Val Gly Tyr Gly Ser Lys Gly Val
        35                  40                  45

Leu His Thr Met Trp His Val Thr Arg Gly Ala Ala Leu Ser Ile Asp
    50                  55                  60

Asp Ala Val Ala Gly Pro Tyr Trp Ala Asp Val Arg Glu Asp Val Val
65                  70                  75                  80

Cys Tyr Gly Gly Ala Trp Ser Leu Glu Glu Lys Trp Lys Gly Glu Thr
                85                  90                  95

Val Gln Val His Ala Phe Pro Pro Gly Arg Ala His Glu Val His Gln
            100                 105                 110

Cys Gln Pro Gly Glu Leu Ile Leu Asp Thr Gly Arg Lys Leu Gly Ala
        115                 120                 125

Ile Pro Ile Asp Leu Val Lys Gly Thr Ser Gly Ser Pro Ile Leu Asn
    130                 135                 140

Ala Gln Gly Val Val Val Gly Leu Tyr Gly Asn Gly Leu Lys Thr Asn
145                 150                 155                 160

Glu Thr Tyr Val Ser Ser Ile Ala Gln Gly Glu Ala Glu Lys Ser Arg
                165                 170                 175

Pro Asn Leu Pro Gln Ala
            180


<210> SEQ ID NO 53
<211> LENGTH: 177
<212> TYPE: PRT
<213> ORGANISM: Flavivirus

<400> SEQUENCE: 53

Ser Gly Val Leu Trp Asp Thr Pro Ser Pro Pro Glu Val Glu Arg Ala
1               5                   10                  15

Val Leu Asp Asp Gly Ile Tyr Arg Ile Leu Gln Arg Gly Leu Leu Gly
            20                  25                  30

Arg Ser Gln Val Gly Val Gly Val Phe Gln Glu Gly Val Phe His Thr
        35                  40                  45

Met Trp His Val Thr Arg Gly Ala Val Leu Met Tyr Gln Gly Lys Arg
    50                  55                  60

Leu Glu Pro Ser Trp Ala Ser Val Lys Lys Asp Leu Ile Ser Tyr Gly
65                  70                  75                  80

Gly Gly Trp Arg Phe Gln Gly Ser Trp Asn Ala Gly Glu Glu Val Gln
                85                  90                  95

Val Ile Ala Val Glu Pro Gly Lys Asn Pro Lys Asn Val Gln Thr Ala
            100                 105                 110

Pro Gly Thr Phe Lys Thr Pro Glu Gly Glu Val Gly Ala Ile Ala Leu
```

115 120 125

Asp Phe Lys Pro Gly Thr Ser Gly Ser Pro Ile Val Asn Arg Glu Gly
130 135 140

Lys Ile Val Gly Leu Tyr Gly Asn Gly Val Val Thr Thr Ser Gly Thr
145 150 155 160

Tyr Val Ser Ala Ile Ala Gln Ala Lys Ala Ser Gln Glu Gly Pro Leu
165 170 175

Pro

<210> SEQ ID NO 54
<211> LENGTH: 176
<212> TYPE: PRT
<213> ORGANISM: Flavivirus

<400> SEQUENCE: 54

Ala Gly Val Leu Trp Asp Val Pro Ser Pro Pro Pro Val Gly Lys Ala
1 5 10 15

Glu Leu Glu Asp Gly Ala Tyr Arg Ile Lys Gln Lys Gly Ile Leu Gly
20 25 30

Tyr Ser Gln Ile Gly Ala Gly Val Tyr Lys Glu Gly Thr Phe His Thr
35 40 45

Met Trp His Val Thr Arg Gly Ala Val Leu Met His Lys Gly Lys Arg
50 55 60

Ile Glu Pro Ser Trp Ala Asp Val Lys Lys Asp Leu Ile Ser Tyr Gly
65 70 75 80

Gly Gly Trp Lys Leu Glu Gly Glu Trp Lys Glu Gly Glu Glu Val Gln
85 90 95

Val Leu Ala Leu Glu Pro Gly Lys Asn Pro Arg Ala Val Gln Thr Lys
100 105 110

Pro Gly Leu Phe Arg Thr Asn Thr Gly Thr Ile Gly Ala Val Ser Leu
115 120 125

Asp Phe Ser Pro Gly Thr Ser Gly Ser Pro Ile Val Asp Lys Lys Gly
130 135 140

Lys Val Val Gly Leu Tyr Gly Asn Gly Val Val Thr Arg Ser Gly Ala
145 150 155 160

Tyr Val Ser Ala Ile Ala Gln Thr Glu Lys Ser Ile Glu Asp Asn Pro
165 170 175

<210> SEQ ID NO 55
<211> LENGTH: 177
<212> TYPE: PRT
<213> ORGANISM: Flavivirus

<400> SEQUENCE: 55

Ser Gly Val Leu Trp Asp Val Pro Ser Pro Pro Glu Thr Gln Lys Ala
1 5 10 15

Glu Leu Glu Glu Gly Val Tyr Arg Ile Lys Gln Gln Gly Ile Phe Gly
20 25 30

Lys Thr Gln Val Gly Val Gly Val Gln Lys Glu Gly Val Phe His Thr
35 40 45

Met Trp His Val Thr Arg Gly Ala Val Leu Thr His Asn Gly Lys Arg
50 55 60

Leu Glu Pro Asn Trp Ala Ser Val Lys Lys Asp Leu Ile Ser Tyr Gly
65 70 75 80

Gly Gly Trp Arg Leu Ser Ala Gln Trp Gln Lys Gly Glu Glu Val Gln
85 90 95

Val Ile Ala Val Glu Pro Gly Lys Asn Pro Lys Asn Phe Gln Thr Thr
100 105 110

Pro Gly Thr Phe Gln Thr Thr Thr Gly Glu Ile Gly Ala Ile Ala Leu
115 120 125

Asp Phe Lys Pro Gly Thr Ser Gly Ser Pro Ile Ile Asn Arg Glu Gly
130 135 140

Lys Val Val Gly Leu Tyr Gly Asn Gly Val Val Thr Lys Asn Gly Gly
145 150 155 160

Tyr Val Ser Gly Ile Ala Gln Thr Asn Ala Glu Pro Asp Gly Pro Thr
165 170 175

Pro

<210> SEQ ID NO 56
<211> LENGTH: 176
<212> TYPE: PRT
<213> ORGANISM: Flavivirus

<400> SEQUENCE: 56

Ser Gly Ala Leu Trp Asp Val Pro Ser Pro Ala Ala Ala Gln Lys Ala
1 5 10 15

Thr Leu Thr Glu Gly Val Tyr Arg Ile Met Gln Arg Gly Leu Phe Gly
20 25 30

Lys Thr Gln Val Gly Val Gly Ile His Met Glu Gly Val Phe His Thr
35 40 45

Met Trp His Val Thr Arg Gly Ser Val Ile Cys His Glu Thr Gly Arg
50 55 60

Leu Glu Pro Ser Trp Ala Asp Val Arg Asn Asp Met Ile Ser Tyr Gly
65 70 75 80

Gly Gly Trp Arg Leu Gly Asp Lys Trp Asp Lys Glu Glu Asp Val Gln
85 90 95

Val Leu Ala Ile Glu Pro Gly Lys Asn Pro Lys His Val Gln Thr Lys
100 105 110

Pro Gly Leu Phe Lys Thr Leu Thr Gly Glu Ile Gly Ala Val Thr Leu
115 120 125

Asp Phe Lys Pro Gly Thr Ser Gly Ser Pro Ile Ile Asn Lys Lys Gly
130 135 140

Arg Val Ile Gly Leu Tyr Gly Asn Gly Ile Val Thr Lys Ser Gly Asp
145 150 155 160

Tyr Val Ser Ala Ile Thr Gln Ala Glu Arg Ile Gly Glu Pro Asp Tyr
165 170 175

<210> SEQ ID NO 57
<211> LENGTH: 177
<212> TYPE: PRT
<213> ORGANISM: Flavivirus

<400> SEQUENCE: 57

Gly Gly Val Phe Trp Asp Thr Pro Ser Pro Lys Pro Cys Ser Lys Gly
1 5 10 15

Asp Thr Thr Thr Gly Val Tyr Arg Ile Met Ala Arg Gly Ile Leu Gly
20 25 30

Thr Tyr Gln Ala Gly Val Gly Val Met Tyr Glu Asn Val Phe His Thr
35 40 45

Leu Trp His Thr Thr Arg Gly Ala Ala Ile Met Ser Gly Glu Gly Lys
50 55 60

Leu Thr Pro Tyr Trp Gly Ser Val Lys Glu Asp Arg Ile Ala Tyr Gly
65 70 75 80

Gly Pro Trp Arg Phe Asp Arg Lys Trp Asn Gly Thr Asp Asp Val Gln
85 90 95

Val Ile Val Val Glu Pro Gly Lys Ala Ala Val Asn Ile Gln Thr Lys
100 105 110

Pro Gly Val Phe Arg Thr Pro Phe Gly Glu Val Gly Ala Val Ser Leu
115 120 125

Asp Tyr Pro Arg Gly Thr Ser Gly Ser Pro Ile Leu Asp Ser Asn Gly
130 135 140

Asp Ile Ile Gly Leu Tyr Gly Asn Gly Val Glu Leu Gly Asp Gly Ser
145 150 155 160

Tyr Val Ser Ala Ile Val Gln Gly Asp Arg Gln Glu Glu Pro Val Pro
165 170 175

Glu

<210> SEQ ID NO 58
<211> LENGTH: 177
<212> TYPE: PRT
<213> ORGANISM: Flavivirus

<400> SEQUENCE: 58

Gly Gly Ala Leu Trp Asp Val Pro Ser Pro Lys Val Tyr Pro Lys Cys
1 5 10 15

Glu Thr Lys Pro Gly Ile Tyr Arg Ile Met Thr Arg Gly Ile Leu Gly
20 25 30

Thr Phe Gln Ala Gly Val Gly Val Met His Glu Gly Val Phe His Thr
35 40 45

Met Trp His Ala Thr Glu Gly Ala Val Leu Arg Asn Gly Glu Gly Arg
50 55 60

Leu Asp Pro Tyr Ala Gly Asp Val Arg Asn Asp Leu Ile Ser Tyr Gly
65 70 75 80

Gly Pro Trp Lys Leu Ser Ala Thr Trp Asp Gly Thr Glu Glu Val Gln
85 90 95

Met Ile Ala Val Ala Pro Gly Lys Pro Ala Ile Asn Val Gln Thr Thr
100 105 110

Pro Gly Val Phe Lys Thr Pro Phe Gly Thr Ile Gly Ala Val Thr Leu
115 120 125

Asp Phe Pro Lys Gly Thr Ser Gly Ser Pro Ile Ile Asn Lys Lys Gly
130 135 140

Glu Ile Ile Gly Leu Tyr Gly Asn Gly Val Leu Ile Gly Gln Gly Glu
145 150 155 160

Tyr Val Ser Gly Ile Ile Gln Gly Glu Arg Thr Glu Glu Pro Ile Pro
165 170 175

Asp

<210> SEQ ID NO 59
<211> LENGTH: 177
<212> TYPE: PRT
<213> ORGANISM: Flavivirus

<400> SEQUENCE: 59

Gly Gly Val Leu Trp Asp Thr Pro Ser Pro Lys Glu Tyr Lys Lys Gly
1 5 10 15

Asp Thr Thr Thr Gly Val Tyr Arg Ile Met Thr Arg Gly Leu Leu Gly
20 25 30

Ser Tyr Gln Ala Gly Ala Gly Val Met Val Glu Gly Val Phe His Thr
35 40 45

Leu Trp His Thr Thr Lys Gly Ala Ala Leu Met Ser Gly Glu Gly Arg
50 55 60

Leu Asp Pro Tyr Trp Gly Ser Val Lys Glu Asp Arg Leu Cys Tyr Gly
65 70 75 80

Gly Pro Trp Lys Leu Gln His Lys Trp Asn Gly Gln Asp Glu Val Gln
85 90 95

Met Ile Val Val Glu Pro Gly Lys Asn Val Lys Asn Val Gln Thr Lys
100 105 110

Pro Gly Val Phe Lys Thr Pro Glu Gly Glu Ile Gly Ala Val Thr Leu
115 120 125

Asp Phe Pro Thr Gly Thr Ser Gly Ser Pro Ile Val Asp Lys Asn Gly
130 135 140

Asp Val Ile Gly Leu Tyr Gly Asn Gly Val Ile Met Pro Asn Gly Ser
145 150 155 160

Tyr Ile Ser Ala Ile Val Gln Gly Glu Arg Met Asp Glu Pro Ile Pro
165 170 175

Ala

<210> SEQ ID NO 60
<211> LENGTH: 181
<212> TYPE: PRT
<213> ORGANISM: Flavivirus

<400> SEQUENCE: 60

Ser Gly Asp Val Leu Trp Asp Ile Pro Thr Pro Lys Ile Ile Glu Glu
1 5 10 15

Cys Glu His Leu Glu Asp Gly Ile Tyr Gly Ile Phe Gln Ser Thr Phe
20 25 30

Leu Gly Ala Ser Gln Arg Gly Val Gly Val Ala Gln Gly Gly Val Phe
35 40 45

His Thr Met Trp His Val Thr Arg Gly Ala Phe Leu Val Arg Asn Gly
50 55 60

Lys Lys Leu Ile Pro Ser Trp Ala Ser Val Lys Glu Asp Leu Val Ala
65 70 75 80

Tyr Gly Gly Ser Trp Lys Leu Glu Gly Arg Trp Asp Gly Glu Glu Glu
85 90 95

Val Gln Leu Ile Ala Ala Val Pro Gly Lys Asn Val Val Asn Val Gln
100 105 110

Thr Lys Pro Ser Leu Phe Lys Val Arg Asn Gly Gly Glu Ile Gly Ala
115 120 125

Val Ala Leu Asp Tyr Pro Ser Gly Thr Ser Gly Ser Pro Ile Val Asn
130 135 140

Arg Asn Gly Glu Val Ile Gly Leu Tyr Gly Asn Gly Ile Leu Val Gly
145 150 155 160

Asp Asn Ser Phe Val Ser Ala Ile Ser Gln Thr Glu Val Lys Glu Glu
165 170 175

Gly Lys Glu Glu Leu
180

<210> SEQ ID NO 61
<211> LENGTH: 88
<212> TYPE: PRT
<213> ORGANISM: Flavivirus

<400> SEQUENCE: 61

Val Ser Val Pro Leu Leu Leu Thr Ser Ser Gln Gln Lys Ala Asp Trp
1 5 10 15

Ile Pro Leu Ala Leu Thr Ile Lys Gly Leu Asn Pro Thr Ala Ile Phe
20 25 30

Leu Thr Thr Leu Ser Arg Thr Ser Lys Lys Arg Ser Trp Pro Leu Asn
35 40 45

Glu Ala Ile Met Ala Val Gly Met Val Ser Ile Leu Ala Ser Ser Leu
50 55 60

Leu Lys Asn Asp Ile Pro Met Thr Gly Pro Leu Val Ala Gly Gly Leu
65 70 75 80

Leu Thr Val Cys Tyr Val Leu Thr
85

<210> SEQ ID NO 62
<211> LENGTH: 89
<212> TYPE: PRT
<213> ORGANISM: Flavivirus

<400> SEQUENCE: 62

Lys Asn Glu Glu Glu Glu Gln Thr Leu Thr Ile Leu Ile Arg Thr Gly
1 5 10 15

Leu Leu Val Ile Ser Gly Leu Phe Pro Val Ser Ile Pro Ile Thr Ala
20 25 30

Ala Ala Trp Tyr Leu Trp Glu Val Lys Lys Gln Arg Ala Gly Val Leu
35 40 45

Trp Asp Val Pro Ser Pro Pro Pro Val Gly Lys Ala Glu Leu Glu Asp
50 55 60

Gly Ala Tyr Arg Ile Lys Gln Arg Gly Ile Leu Gly Tyr Ser Gln Ile
65 70 75 80

Gly Ala Gly Val Tyr Lys Glu Gly Thr
85

<210> SEQ ID NO 63
<211> LENGTH: 89
<212> TYPE: PRT
<213> ORGANISM: Flavivirus

<400> SEQUENCE: 63

Glu Asn Val Lys Val Glu Ile Trp Thr Lys Lys Gly Glu Arg Lys Lys
1 5 10 15

Leu Lys Pro Arg Trp Leu Asp Ala Arg Ile Tyr Ser Asp Pro Leu Ala
20 25 30

Leu Lys Glu Phe Lys Glu Phe Ala Ala Gly Arg Lys Ser Leu Thr Leu
35 40 45

Asn Leu Ile Thr Glu Met Gly Arg Leu Pro Thr Phe Met Thr Gln Lys
50 55 60

Ala Arg Asp Ala Leu Asp Asn Leu Ala Val Leu His Thr Ala Glu Ser
65 70 75 80

Gly Gly Arg Ala Tyr Asn His Ala Leu
85

<210> SEQ ID NO 64
<211> LENGTH: 89
<212> TYPE: PRT
<213> ORGANISM: Flavivirus

<400> SEQUENCE: 64

Trp Glu Gly Asn Pro Gly Arg Phe Trp Asn Thr Thr Ile Ala Val Ser
1               5                   10                  15

Met Ala Asn Ile Phe Arg Gly Ser Tyr Leu Ala Gly Ala Gly Leu Leu
            20                  25                  30

Phe Ser Ile Met Lys Asn Thr Thr Asn Thr Arg Arg Gly Thr Gly Asn
        35                  40                  45

Ile Gly Glu Thr Leu Gly Glu Lys Trp Lys Ser Arg Leu Asn Ala Leu
    50                  55                  60

Gly Lys Ser Glu Phe Gln Ile Tyr Lys Lys Ser Gly Ile Gln Glu Val
65                  70                  75                  80

Asp Arg Thr Leu Ala Lys Glu Gly Ile
                85

<210> SEQ ID NO 65
<211> LENGTH: 89
<212> TYPE: PRT
<213> ORGANISM: Flavivirus

<400> SEQUENCE: 65

Arg Leu Ile Arg Gly His Arg Glu Gln Lys Gly Leu Thr Trp Ile Val
1               5                   10                  15

Pro Leu Ala Gly Leu Leu Gly Gly Glu Gly Ser Gly Ile Arg Leu Leu
            20                  25                  30

Ala Phe Trp Glu Leu Ala Ala His Arg Gly Arg Arg Ser Phe Ser Glu
        35                  40                  45

Pro Leu Thr Val Val Gly Val Met Leu Thr Leu Ala Ser Gly Met Met
    50                  55                  60

Arg His Thr Ser Gln Glu Ala Leu Cys Ala Leu Ala Val Ala Ser Phe
65                  70                  75                  80

Leu Leu Leu Met Leu Val Leu Gly Thr
                85

<210> SEQ ID NO 66
<211> LENGTH: 89
<212> TYPE: PRT
<213> ORGANISM: Flavivirus

<400> SEQUENCE: 66

Leu Glu Lys Glu Glu Arg Val Met Ala Phe Trp Leu Leu Ala Gly Leu
1               5                   10                  15

Ala Ala Ser Ala Phe His Trp Ser Gly Ile Leu Gly Val Met Gly Leu
            20                  25                  30

Trp Thr Leu Ser Glu Met Leu Arg Ser Ala Arg Arg Ser Asp Leu Val
        35                  40                  45

Phe Ser Gly Gln Gly Gly Arg Glu Arg Gly Asp Arg Pro Phe Glu Val
    50                  55                  60

Lys Asp Gly Val Tyr Arg Ile Phe Ser Pro Gly Leu Leu Trp Gly Gln
65                  70                  75                  80

Arg Gln Val Gly Val Gly Tyr Gly Ser
                85

<210> SEQ ID NO 67
<211> LENGTH: 89
<212> TYPE: PRT
<213> ORGANISM: Flavivirus

<400> SEQUENCE: 67

-continued

```
Asn Gly Asp Leu Val Thr Phe Arg Ser Pro Asn Gly Ala Glu Arg Thr
1               5                   10                  15

Leu Arg Pro Val Trp Arg Asp Ala Arg Met Phe Arg Glu Gly Arg Asp
            20                  25                  30

Ile Arg Glu Phe Val Ala Tyr Ala Ser Gly Arg Arg Ser Phe Gly Asp
        35                  40                  45

Val Leu Thr Gly Met Ser Gly Val Pro Glu Leu Leu Arg His Arg Cys
    50                  55                  60

Val Ser Ala Leu Asp Val Phe Tyr Thr Leu Met His Glu Glu Pro Gly
65                  70                  75                  80

Ser Arg Ala Met Arg Met Ala Glu Arg
                85


<210> SEQ ID NO 68
<211> LENGTH: 89
<212> TYPE: PRT
<213> ORGANISM: Flavivirus

<400> SEQUENCE: 68

Leu Arg Pro Glu Ala Asp Thr Leu Trp Thr Met Pro Val Ala Cys Gly
1               5                   10                  15

Leu Ser Gly Val Val Arg Gly Ser Leu Trp Gly Phe Leu Pro Leu Gly
            20                  25                  30

His Arg Leu Trp Leu Arg Ala Ser Gly Ser Arg Arg Gly Gly Ser Glu
        35                  40                  45

Gly Asp Thr Leu Gly Asp Leu Trp Lys Arg Arg Leu Asn Ser Cys Thr
    50                  55                  60

Lys Glu Glu Phe Phe Val Tyr Arg Arg Thr Gly Ile Leu Glu Thr Glu
65                  70                  75                  80

Arg Asp Lys Ala Arg Glu Leu Leu Arg
                85


<210> SEQ ID NO 69
<211> LENGTH: 9
<212> TYPE: PRT
<213> ORGANISM: Flavivirus

<400> SEQUENCE: 69

Arg Asp Phe Val Glu Gly Val Ser Gly
1               5


<210> SEQ ID NO 70
<211> LENGTH: 10
<212> TYPE: PRT
<213> ORGANISM: Flavivirus

<400> SEQUENCE: 70

Glu His Gly Ser Cys Val Thr Thr Met Ala
1               5                   10


<210> SEQ ID NO 71
<211> LENGTH: 10
<212> TYPE: PRT
<213> ORGANISM: Flavivirus

<400> SEQUENCE: 71

Ala Thr Leu Arg Lys Tyr Cys Ile Glu Ala
1               5                   10
```

<210> SEQ ID NO 72
<211> LENGTH: 8
<212> TYPE: PRT
<213> ORGANISM: Flavivirus

<400> SEQUENCE: 72

Arg Cys Pro Thr Gln Gly Glu Pro
1               5

<210> SEQ ID NO 73
<211> LENGTH: 10
<212> TYPE: PRT
<213> ORGANISM: Flavivirus

<400> SEQUENCE: 73

Arg Gly Trp Gly Asn Gly Cys Gly Leu Phe
1               5                   10

<210> SEQ ID NO 74
<211> LENGTH: 15
<212> TYPE: PRT
<213> ORGANISM: Flavivirus

<400> SEQUENCE: 74

Val Gln Pro Glu Asn Leu Glu Tyr Thr Ile Val Ile Thr Pro His
1               5                   10                  15

<210> SEQ ID NO 75
<211> LENGTH: 11
<212> TYPE: PRT
<213> ORGANISM: Flavivirus

<400> SEQUENCE: 75

Gly Lys Glu Ile Lys Ile Thr Pro Gln Ser Ser
1               5                   10

<210> SEQ ID NO 76
<211> LENGTH: 12
<212> TYPE: PRT
<213> ORGANISM: Flavivirus

<400> SEQUENCE: 76

Gly Leu Asp Phe Asn Glu Met Val Leu Leu Gln Met
1               5                   10

<210> SEQ ID NO 77
<211> LENGTH: 10
<212> TYPE: PRT
<213> ORGANISM: Flavivirus

<400> SEQUENCE: 77

Trp Leu Val His Arg Gln Trp Phe Leu Asp
1               5                   10

<210> SEQ ID NO 78
<211> LENGTH: 7
<212> TYPE: PRT
<213> ORGANISM: Flavivirus

<400> SEQUENCE: 78

Thr Phe Lys Asn Pro His Ala
1               5

<210> SEQ ID NO 79
<211> LENGTH: 9

<212> TYPE: PRT
<213> ORGANISM: Flavivirus

<400> SEQUENCE: 79

Val Val Val Leu Gly Ser Gln Glu Gly
1 5

<210> SEQ ID NO 80
<211> LENGTH: 8
<212> TYPE: PRT
<213> ORGANISM: Flavivirus

<400> SEQUENCE: 80

Lys Gly Met Ser Tyr Ser Met Cys
1 5

<210> SEQ ID NO 81
<211> LENGTH: 17
<212> TYPE: PRT
<213> ORGANISM: Flavivirus

<400> SEQUENCE: 81

Ile Ala Glu Thr Gln His Gly Thr Ile Val Ile Arg Val Gln Tyr Glu
1 5 10 15

Gly

<210> SEQ ID NO 82
<211> LENGTH: 5
<212> TYPE: PRT
<213> ORGANISM: Flavivirus

<400> SEQUENCE: 82

Pro Cys Lys Ile Pro
1 5

<210> SEQ ID NO 83
<211> LENGTH: 8
<212> TYPE: PRT
<213> ORGANISM: Flavivirus

<400> SEQUENCE: 83

Gly Arg Leu Ile Thr Val Asn Pro
1 5

<210> SEQ ID NO 84
<211> LENGTH: 16
<212> TYPE: PRT
<213> ORGANISM: Flavivirus

<400> SEQUENCE: 84

Asn Ile Glu Ala Glu Pro Pro Phe Gly Asp Ser Tyr Ile Ile Ile Gly
1 5 10 15

<210> SEQ ID NO 85
<211> LENGTH: 9
<212> TYPE: PRT
<213> ORGANISM: Flavivirus

<400> SEQUENCE: 85

Trp Phe Lys Lys Gly Ser Ser Ile Gly
1 5

<210> SEQ ID NO 86
<211> LENGTH: 12

-continued

<212> TYPE: PRT
<213> ORGANISM: Flavivirus

<400> SEQUENCE: 86

Gly Asp Thr Ala Trp Asp Phe Gly Ser Leu Gly Gly
1 5 10

<210> SEQ ID NO 87
<211> LENGTH: 14
<212> TYPE: PRT
<213> ORGANISM: Flavivirus

<400> SEQUENCE: 87

Ser Ile Gly Lys Ala Leu His Gln Val Phe Gly Ala Ile Tyr
1 5 10

<210> SEQ ID NO 88
<211> LENGTH: 6
<212> TYPE: PRT
<213> ORGANISM: Flavivirus

<400> SEQUENCE: 88

Phe Ser Gly Val Ser Trp
1 5

<210> SEQ ID NO 89
<211> LENGTH: 13
<212> TYPE: PRT
<213> ORGANISM: Flavivirus

<400> SEQUENCE: 89

Gly Val Ile Ile Thr Trp Ile Gly Met Asn Ser Arg Ser
1 5 10

<210> SEQ ID NO 90
<211> LENGTH: 11
<212> TYPE: PRT
<213> ORGANISM: Flavivirus

<400> SEQUENCE: 90

Gly Val Leu Trp Asp Glu Asn Val Pro Ser Pro
1 5 10

<210> SEQ ID NO 91
<211> LENGTH: 8
<212> TYPE: PRT
<213> ORGANISM: Flavivirus

<400> SEQUENCE: 91

Gly Ala Tyr Arg Ile Lys Gln Lys
1 5

<210> SEQ ID NO 92
<211> LENGTH: 8
<212> TYPE: PRT
<213> ORGANISM: Flavivirus

<400> SEQUENCE: 92

Gly Tyr Ser Gln Ile Gly Ala Gly
1 5

<210> SEQ ID NO 93
<211> LENGTH: 10
<212> TYPE: PRT
<213> ORGANISM: Flavivirus

<400> SEQUENCE: 93

His Thr Met Trp His Val Thr Arg Gly Ala
1 5 10

<210> SEQ ID NO 94
<211> LENGTH: 19
<212> TYPE: PRT
<213> ORGANISM: Flavivirus

<400> SEQUENCE: 94

Pro Ser Trp Ala Asp Glu Asn Val Lys Lys Asp Leu Ile Ser Tyr Gly
1 5 10 15

Gly Gly Trp

<210> SEQ ID NO 95
<211> LENGTH: 11
<212> TYPE: PRT
<213> ORGANISM: Flavivirus

<400> SEQUENCE: 95

Glu Glu Val Gln Val Leu Ala Leu Glu Pro Gly
1 5 10

<210> SEQ ID NO 96
<211> LENGTH: 6
<212> TYPE: PRT
<213> ORGANISM: Flavivirus

<400> SEQUENCE: 96

Gly Thr Ser Gly Ser Pro
1 5

<210> SEQ ID NO 97
<211> LENGTH: 6
<212> TYPE: PRT
<213> ORGANISM: Flavivirus

<400> SEQUENCE: 97

Gly Leu Tyr Gly Asn Gly
1 5

<210> SEQ ID NO 98
<211> LENGTH: 7
<212> TYPE: PRT
<213> ORGANISM: Flavivirus

<400> SEQUENCE: 98

Tyr Val Ser Ala Ile Ala Gln
1 5

<210> SEQ ID NO 99
<211> LENGTH: 12
<212> TYPE: PRT
<213> ORGANISM: Flavivirus

<400> SEQUENCE: 99

Lys Phe Ala Cys Glu Ala Lys Lys Lys Ala Thr Gly
1 5 10

<210> SEQ ID NO 100
<211> LENGTH: 12
<212> TYPE: PRT
<213> ORGANISM: Flavivirus

<400> SEQUENCE: 100

Lys Phe Ala Cys Glu Ala Lys Lys Lys Ala Thr Gly
1               5                   10

<210> SEQ ID NO 101
<211> LENGTH: 12
<212> TYPE: PRT
<213> ORGANISM: Flavivirus

<400> SEQUENCE: 101

Lys Phe Ser Cys Glu Ala Lys Lys Lys Ala Thr Gly
1               5                   10

<210> SEQ ID NO 102
<211> LENGTH: 12
<212> TYPE: PRT
<213> ORGANISM: Flavivirus

<400> SEQUENCE: 102

Lys Ala Ala Cys Gly Ala Lys Lys Lys Ala Thr Gly
1               5                   10

<210> SEQ ID NO 103
<211> LENGTH: 12
<212> TYPE: PRT
<213> ORGANISM: Flavivirus

<400> SEQUENCE: 103

Lys Ala Ala Cys Glu Ala Lys Lys Lys Ala Thr Gly
1               5                   10

<210> SEQ ID NO 104
<211> LENGTH: 12
<212> TYPE: PRT
<213> ORGANISM: Flavivirus

<400> SEQUENCE: 104

Lys Ala Ala Cys Glu Ala Lys Lys Lys Ala Thr Gly
1               5                   10

<210> SEQ ID NO 105
<211> LENGTH: 12
<212> TYPE: PRT
<213> ORGANISM: Flavivirus

<400> SEQUENCE: 105

Lys Ala Ser Cys Glu Ala Lys Lys Lys Ala Thr Gly
1               5                   10

<210> SEQ ID NO 106
<211> LENGTH: 12
<212> TYPE: PRT
<213> ORGANISM: Flavivirus

<400> SEQUENCE: 106

Lys Phe Thr Cys Glu Asp Lys Lys Lys Ala Thr Gly
1               5                   10

<210> SEQ ID NO 107
<211> LENGTH: 12
<212> TYPE: PRT
<213> ORGANISM: Flavivirus

<400> SEQUENCE: 107

Lys Phe Glu Cys Glu Glu Ala Lys Lys Ala Val Gly
1 5 10

<210> SEQ ID NO 108
<211> LENGTH: 12
<212> TYPE: PRT
<213> ORGANISM: Flavivirus

<400> SEQUENCE: 108

Lys Phe Glu Cys Glu Glu Ala Lys Lys Ala Val Gly
1 5 10

<210> SEQ ID NO 109
<211> LENGTH: 12
<212> TYPE: PRT
<213> ORGANISM: Flavivirus

<400> SEQUENCE: 109

Lys Phe Thr Cys Glu Glu Lys Arg Thr Ala Ala Gly
1 5 10

<210> SEQ ID NO 110
<211> LENGTH: 12
<212> TYPE: PRT
<213> ORGANISM: Flavivirus

<400> SEQUENCE: 110

Lys Phe Ser Cys Glu Glu Arg Lys Thr Val Val Gly
1 5 10

<210> SEQ ID NO 111
<211> LENGTH: 12
<212> TYPE: PRT
<213> ORGANISM: Flavivirus

<400> SEQUENCE: 111

Lys Phe Asp Cys Glu Val Asn Lys Lys Ala Thr Gly
1 5 10

<210> SEQ ID NO 112
<211> LENGTH: 10
<212> TYPE: PRT
<213> ORGANISM: Flavivirus

<400> SEQUENCE: 112

Met Phe Thr Cys Lys Lys Asn Met Glu Gly
1 5 10

<210> SEQ ID NO 113
<211> LENGTH: 10
<212> TYPE: PRT
<213> ORGANISM: Flavivirus

<400> SEQUENCE: 113

Lys Phe Lys Cys Val Thr Lys Leu Glu Gly
1 5 10

<210> SEQ ID NO 114
<211> LENGTH: 10
<212> TYPE: PRT
<213> ORGANISM: Flavivirus

<400> SEQUENCE: 114

Lys Phe Gln Cys Leu Glu Pro Ile Glu Gly

-continued 1 5 10

<210> SEQ ID NO 115
<211> LENGTH: 10
<212> TYPE: PRT
<213> ORGANISM: Flavivirus

<400> SEQUENCE: 115

Lys Phe Ser Cys Ser Gly Lys Ile Thr Gly
1 5 10

<210> SEQ ID NO 116
<211> LENGTH: 10
<212> TYPE: PRT
<213> ORGANISM: Flavivirus

<400> SEQUENCE: 116

Lys Phe Ser Cys Pro Gly Lys Ala Thr Gly
1 5 10

<210> SEQ ID NO 117
<211> LENGTH: 10
<212> TYPE: PRT
<213> ORGANISM: Flavivirus

<400> SEQUENCE: 117

Lys Phe Gly Cys Thr Gln Lys Ala Met Gly
1 5 10

<210> SEQ ID NO 118
<211> LENGTH: 10
<212> TYPE: PRT
<213> ORGANISM: Flavivirus

<400> SEQUENCE: 118

Lys Phe Ser Cys Thr Ser Lys Ala Ile Gly
1 5 10

<210> SEQ ID NO 119
<211> LENGTH: 10
<212> TYPE: PRT
<213> ORGANISM: Flavivirus

<400> SEQUENCE: 119

Lys Phe Ala Cys Ser Thr Lys Ala Ile Gly
1 5 10

<210> SEQ ID NO 120
<211> LENGTH: 10
<212> TYPE: PRT
<213> ORGANISM: Flavivirus

<400> SEQUENCE: 120

Lys Phe Thr Cys Lys Asn Lys Ala Thr Gly
1 5 10

<210> SEQ ID NO 121
<211> LENGTH: 10
<212> TYPE: PRT
<213> ORGANISM: Flavivirus

<400> SEQUENCE: 121

Lys Gly Thr Cys Ala Lys Ser Met Ser Leu
1 5 10

<210> SEQ ID NO 122
<211> LENGTH: 12
<212> TYPE: PRT
<213> ORGANISM: Flavivirus

<400> SEQUENCE: 122

Lys Thr Thr Cys Lys Asn Asp Ala Asn Ile Ile Lys
1               5                   10

<210> SEQ ID NO 123
<211> LENGTH: 11
<212> TYPE: PRT
<213> ORGANISM: Flavivirus

<400> SEQUENCE: 123

Lys Thr Thr Cys Lys Ser Ser Gly Ile Ala Lys
1               5                   10

<210> SEQ ID NO 124
<211> LENGTH: 11
<212> TYPE: PRT
<213> ORGANISM: Flavivirus

<400> SEQUENCE: 124

Lys Ala Thr Cys Gly Ala Asn Asp Ile Ile Lys
1               5                   10

<210> SEQ ID NO 125
<211> LENGTH: 11
<212> TYPE: PRT
<213> ORGANISM: Flavivirus

<400> SEQUENCE: 125

Lys Val Ala Cys Asn Thr Ala Asn Val Met Lys
1               5                   10

<210> SEQ ID NO 126
<211> LENGTH: 16
<212> TYPE: PRT
<213> ORGANISM: Flavivirus

<400> SEQUENCE: 126

Leu Glu Leu Asp Lys Thr Ala Glu His Leu Pro Lys Ala Trp Gln Val
1               5                   10                  15

<210> SEQ ID NO 127
<211> LENGTH: 16
<212> TYPE: PRT
<213> ORGANISM: Flavivirus

<400> SEQUENCE: 127

Leu Glu Leu Asp Lys Thr Ala Glu His Leu Pro Lys Ala Trp Gln Val
1               5                   10                  15

<210> SEQ ID NO 128
<211> LENGTH: 16
<212> TYPE: PRT
<213> ORGANISM: Flavivirus

<400> SEQUENCE: 128

Leu Glu Leu Asp Lys Thr Val Glu His Leu Pro Thr Ala Trp Gln Val
1               5                   10                  15

<210> SEQ ID NO 129

<211> LENGTH: 16
<212> TYPE: PRT
<213> ORGANISM: Flavivirus

<400> SEQUENCE: 129

Leu Glu Leu Asp Lys Thr Ala Glu His Leu Pro Thr Ala Trp Gln Val
1 5 10 15

<210> SEQ ID NO 130
<211> LENGTH: 16
<212> TYPE: PRT
<213> ORGANISM: Flavivirus

<400> SEQUENCE: 130

Leu Glu Leu Asp Lys Thr Ala Glu His Leu Pro Thr Ala Trp Gln Val
1 5 10 15

<210> SEQ ID NO 131
<211> LENGTH: 16
<212> TYPE: PRT
<213> ORGANISM: Flavivirus

<400> SEQUENCE: 131

Leu Glu Leu Asp Lys Thr Ala Glu His Leu Pro Thr Ala Trp Gln Val
1 5 10 15

<210> SEQ ID NO 132
<211> LENGTH: 16
<212> TYPE: PRT
<213> ORGANISM: Flavivirus

<400> SEQUENCE: 132

Leu Glu Leu Asp Lys Thr Ala Glu His Leu Pro Thr Ala Trp Gln Val
1 5 10 15

<210> SEQ ID NO 133
<211> LENGTH: 16
<212> TYPE: PRT
<213> ORGANISM: Flavivirus

<400> SEQUENCE: 133

Leu Ala Leu Asp Lys Thr His Glu His Leu Pro Thr Ala Trp Gln Val
1 5 10 15

<210> SEQ ID NO 134
<211> LENGTH: 16
<212> TYPE: PRT
<213> ORGANISM: Flavivirus

<400> SEQUENCE: 134

Met Ser Leu Gly Ser Ser Lys Asp His Leu Pro Ser Ala Trp Gln Val
1 5 10 15

<210> SEQ ID NO 135
<211> LENGTH: 16
<212> TYPE: PRT
<213> ORGANISM: Flavivirus

<400> SEQUENCE: 135

Met Ser Leu Asp Ser Ser Lys Asp His Leu Pro Ser Ala Trp Gln Val
1 5 10 15

<210> SEQ ID NO 136
<211> LENGTH: 16
<212> TYPE: PRT

-continued

<213> ORGANISM: Flavivirus

<400> SEQUENCE: 136

Leu Glu Met Asp Lys Thr Asn Glu His Leu Pro Gln Ala Trp Gln Val
1 5 10 15

<210> SEQ ID NO 137
<211> LENGTH: 16
<212> TYPE: PRT
<213> ORGANISM: Flavivirus

<400> SEQUENCE: 137

Met Glu Met Asn Arg Thr Thr Ser His Leu Pro Lys Ala Trp Gln Val
1 5 10 15

<210> SEQ ID NO 138
<211> LENGTH: 15
<212> TYPE: PRT
<213> ORGANISM: Flavivirus

<400> SEQUENCE: 138

Leu Glu Leu Glu Gly Gln Ala Leu His Pro Lys Gly Trp Ala Val
1 5 10 15

<210> SEQ ID NO 139
<211> LENGTH: 10
<212> TYPE: PRT
<213> ORGANISM: Flavivirus

<400> SEQUENCE: 139

Leu Gln Met Glu Asp Lys Ala Trp Leu Val
1 5 10

<210> SEQ ID NO 140
<211> LENGTH: 10
<212> TYPE: PRT
<213> ORGANISM: Flavivirus

<400> SEQUENCE: 140

Leu Thr Met Lys Glu Lys Ser Trp Leu Val
1 5 10

<210> SEQ ID NO 141
<211> LENGTH: 10
<212> TYPE: PRT
<213> ORGANISM: Flavivirus

<400> SEQUENCE: 141

Leu Thr Met Lys Asn Lys Ala Trp Met Val
1 5 10

<210> SEQ ID NO 142
<211> LENGTH: 10
<212> TYPE: PRT
<213> ORGANISM: Flavivirus

<400> SEQUENCE: 142

Met Lys Met Lys Lys Lys Thr Trp Leu Val
1 5 10

<210> SEQ ID NO 143
<211> LENGTH: 10
<212> TYPE: PRT
<213> ORGANISM: Flavivirus

<400> SEQUENCE: 143

Met Ser Leu Asn Asn Lys His Trp Leu Val
1 5 10

<210> SEQ ID NO 144
<211> LENGTH: 10
<212> TYPE: PRT
<213> ORGANISM: Flavivirus

<400> SEQUENCE: 144

Met Ser Met Asn Asn Lys His Trp Leu Val
1 5 10

<210> SEQ ID NO 145
<211> LENGTH: 10
<212> TYPE: PRT
<213> ORGANISM: Flavivirus

<400> SEQUENCE: 145

Met Thr Val Gly Ser Lys Ser Phe Leu Val
1 5 10

<210> SEQ ID NO 146
<211> LENGTH: 10
<212> TYPE: PRT
<213> ORGANISM: Flavivirus

<400> SEQUENCE: 146

Met Thr Val Gly Thr Lys Thr Phe Leu Val
1 5 10

<210> SEQ ID NO 147
<211> LENGTH: 10
<212> TYPE: PRT
<213> ORGANISM: Flavivirus

<400> SEQUENCE: 147

Phe Thr Val Lys Glu Lys Ser Trp Leu Val
1 5 10

<210> SEQ ID NO 148
<211> LENGTH: 10
<212> TYPE: PRT
<213> ORGANISM: Flavivirus

<400> SEQUENCE: 148

Ala Glu Met Glu Lys Glu Ser Trp Ile Val
1 5 10

<210> SEQ ID NO 149
<211> LENGTH: 10
<212> TYPE: PRT
<213> ORGANISM: Flavivirus

<400> SEQUENCE: 149

Ile Glu Ile Asp Asn His Phe Tyr Asn Val
1 5 10

<210> SEQ ID NO 150
<211> LENGTH: 10
<212> TYPE: PRT
<213> ORGANISM: Flavivirus

<400> SEQUENCE: 150

Leu Glu Ile Asp Asn His Tyr Phe Asn Val
1 5 10

<210> SEQ ID NO 151
<211> LENGTH: 10
<212> TYPE: PRT
<213> ORGANISM: Flavivirus

<400> SEQUENCE: 151

Ile Glu Leu Asp Gly His Met Phe Asn Val
1 5 10

<210> SEQ ID NO 152
<211> LENGTH: 10
<212> TYPE: PRT
<213> ORGANISM: Flavivirus

<400> SEQUENCE: 152

Leu Glu Val Asp Gly His Tyr Phe Asn Val
1 5 10

<210> SEQ ID NO 153
<211> LENGTH: 12
<212> TYPE: PRT
<213> ORGANISM: Flavivirus

<400> SEQUENCE: 153

Tyr Thr Val Cys Glu Gly Ser Lys Phe Ala Trp Lys
1 5 10

<210> SEQ ID NO 154
<211> LENGTH: 12
<212> TYPE: PRT
<213> ORGANISM: Flavivirus

<400> SEQUENCE: 154

Tyr Thr Val Cys Glu Gly Ser Lys Phe Ala Trp Lys
1 5 10

<210> SEQ ID NO 155
<211> LENGTH: 12
<212> TYPE: PRT
<213> ORGANISM: Flavivirus

<400> SEQUENCE: 155

Tyr Thr Met Cys Asp Lys Thr Lys Phe Thr Trp Lys
1 5 10

<210> SEQ ID NO 156
<211> LENGTH: 12
<212> TYPE: PRT
<213> ORGANISM: Flavivirus

<400> SEQUENCE: 156

Tyr Thr Thr Cys Asp Lys Thr Lys Phe Thr Trp Lys
1 5 10

<210> SEQ ID NO 157
<211> LENGTH: 12
<212> TYPE: PRT
<213> ORGANISM: Flavivirus

<400> SEQUENCE: 157

Tyr Thr Met Cys Asp Lys Ser Lys Phe Ala Trp Lys
1 5 10

<210> SEQ ID NO 158
<211> LENGTH: 12
<212> TYPE: PRT
<213> ORGANISM: Flavivirus

<400> SEQUENCE: 158

Tyr Thr Met Cys Asp Lys Ser Lys Phe Ala Trp Lys
1 5 10

<210> SEQ ID NO 159
<211> LENGTH: 12
<212> TYPE: PRT
<213> ORGANISM: Flavivirus

<400> SEQUENCE: 159

Tyr Thr Met Cys Asp Lys Ala Lys Phe Thr Trp Lys
1 5 10

<210> SEQ ID NO 160
<211> LENGTH: 12
<212> TYPE: PRT
<213> ORGANISM: Flavivirus

<400> SEQUENCE: 160

Tyr Thr Val Cys Asp Lys Thr Lys Phe Thr Trp Lys
1 5 10

<210> SEQ ID NO 161
<211> LENGTH: 13
<212> TYPE: PRT
<213> ORGANISM: Flavivirus

<400> SEQUENCE: 161

Tyr Ser Met Cys Asp Glu Lys Thr Lys Phe Lys Trp Lys
1 5 10

<210> SEQ ID NO 162
<211> LENGTH: 12
<212> TYPE: PRT
<213> ORGANISM: Flavivirus

<400> SEQUENCE: 162

Tyr Ser Met Cys Asp Lys Ala Lys Phe Lys Trp Lys
1 5 10

<210> SEQ ID NO 163
<211> LENGTH: 12
<212> TYPE: PRT
<213> ORGANISM: Flavivirus

<400> SEQUENCE: 163

Tyr Ser Met Cys Glu Ser Gly Lys Phe Ser Trp Lys
1 5 10

<210> SEQ ID NO 164
<211> LENGTH: 12
<212> TYPE: PRT
<213> ORGANISM: Flavivirus

<400> SEQUENCE: 164

Tyr Ser Met Cys Glu Ala Asp Lys Phe Lys Trp Lys
1 5 10

<210> SEQ ID NO 165
<211> LENGTH: 12
<212> TYPE: PRT
<213> ORGANISM: Flavivirus

<400> SEQUENCE: 165

Tyr Ser Met Cys Glu Glu Gly Lys Phe Ala Trp Lys
1 5 10

<210> SEQ ID NO 166
<211> LENGTH: 11
<212> TYPE: PRT
<213> ORGANISM: Flavivirus

<400> SEQUENCE: 166

Tyr Ser Met Cys Thr Gly Lys Phe Lys Ile Val
1 5 10

<210> SEQ ID NO 167
<211> LENGTH: 11
<212> TYPE: PRT
<213> ORGANISM: Flavivirus

<400> SEQUENCE: 167

Tyr Val Met Cys Thr Gly Ser Phe Lys Leu Glu
1 5 10

<210> SEQ ID NO 168
<211> LENGTH: 11
<212> TYPE: PRT
<213> ORGANISM: Flavivirus

<400> SEQUENCE: 168

Tyr Ala Met Cys Thr Asn Thr Phe Val Leu Lys
1 5 10

<210> SEQ ID NO 169
<211> LENGTH: 11
<212> TYPE: PRT
<213> ORGANISM: Flavivirus

<400> SEQUENCE: 169

Tyr Thr Met Cys Ser Gly Lys Phe Ser Ile Asp
1 5 10

<210> SEQ ID NO 170
<211> LENGTH: 11
<212> TYPE: PRT
<213> ORGANISM: Flavivirus

<400> SEQUENCE: 170

Tyr Ala Met Cys Lys Gly Thr Phe Ala Phe Ala
1 5 10

<210> SEQ ID NO 171
<211> LENGTH: 11
<212> TYPE: PRT
<213> ORGANISM: Flavivirus

<400> SEQUENCE: 171

Tyr Leu Met Cys Lys Asp Lys Phe Ala Phe Ala
1 5 10

<210> SEQ ID NO 172
<211> LENGTH: 11

<212> TYPE: PRT
<213> ORGANISM: Flavivirus

<400> SEQUENCE: 172

Tyr Gly Met Cys Thr Glu Lys Phe Ser Phe Ala
1 5 10

<210> SEQ ID NO 173
<211> LENGTH: 11
<212> TYPE: PRT
<213> ORGANISM: Flavivirus

<400> SEQUENCE: 173

Tyr Gly Val Cys Ser Lys Ala Phe Lys Phe Leu
1 5 10

<210> SEQ ID NO 174
<211> LENGTH: 11
<212> TYPE: PRT
<213> ORGANISM: Flavivirus

<400> SEQUENCE: 174

Tyr Gly Met Cys Asp Ser Ala Phe Thr Phe Ser
1 5 10

<210> SEQ ID NO 175
<211> LENGTH: 11
<212> TYPE: PRT
<213> ORGANISM: Flavivirus

<400> SEQUENCE: 175

Tyr Lys Met Cys Thr Asp Lys Met Ser Phe Val
1 5 10

<210> SEQ ID NO 176
<211> LENGTH: 11
<212> TYPE: PRT
<213> ORGANISM: Flavivirus

<400> SEQUENCE: 176

Tyr Ser Gln Cys Thr Lys Pro Phe Glu Trp Ile
1 5 10

<210> SEQ ID NO 177
<211> LENGTH: 11
<212> TYPE: PRT
<213> ORGANISM: Flavivirus

<400> SEQUENCE: 177

Tyr Pro Tyr Cys Gly Asp Ser Phe Val Trp Lys
1 5 10

<210> SEQ ID NO 178
<211> LENGTH: 11
<212> TYPE: PRT
<213> ORGANISM: Flavivirus

<400> SEQUENCE: 178

Tyr Gln Met Cys Ser Ser Ser Phe Val Trp His
1 5 10

<210> SEQ ID NO 179
<211> LENGTH: 11
<212> TYPE: PRT
<213> ORGANISM: Flavivirus

<400> SEQUENCE: 179

Tyr Val Val Cys Gly Gly Lys Phe Ala Trp Ala
1 5 10

<210> SEQ ID NO 180
<211> LENGTH: 8
<212> TYPE: PRT
<213> ORGANISM: Flavivirus

<400> SEQUENCE: 180

Ile Tyr Val Gly Glu Leu Ser His
1 5

<210> SEQ ID NO 181
<211> LENGTH: 8
<212> TYPE: PRT
<213> ORGANISM: Flavivirus

<400> SEQUENCE: 181

Ile Tyr Val Gly Glu Leu Ser His
1 5

<210> SEQ ID NO 182
<211> LENGTH: 8
<212> TYPE: PRT
<213> ORGANISM: Flavivirus

<400> SEQUENCE: 182

Ile Tyr Val Gly Glu Leu Ser His
1 5

<210> SEQ ID NO 183
<211> LENGTH: 8
<212> TYPE: PRT
<213> ORGANISM: Flavivirus

<400> SEQUENCE: 183

Ile Tyr Val Gly Glu Leu Ser His
1 5

<210> SEQ ID NO 184
<211> LENGTH: 8
<212> TYPE: PRT
<213> ORGANISM: Flavivirus

<400> SEQUENCE: 184

Ile Tyr Val Gly Glu Leu Ser His
1 5

<210> SEQ ID NO 185
<211> LENGTH: 8
<212> TYPE: PRT
<213> ORGANISM: Flavivirus

<400> SEQUENCE: 185

Ile Tyr Ile Phe Glu Leu Ser His
1 5

<210> SEQ ID NO 186
<211> LENGTH: 8
<212> TYPE: PRT
<213> ORGANISM: Flavivirus

<400> SEQUENCE: 186

Ile Tyr Val Gly Glu Leu Lys His
1               5

<210> SEQ ID NO 187
<211> LENGTH: 8
<212> TYPE: PRT
<213> ORGANISM: Flavivirus

<400> SEQUENCE: 187

Ile Tyr Val Gly Asp Leu Asn His
1               5

<210> SEQ ID NO 188
<211> LENGTH: 8
<212> TYPE: PRT
<213> ORGANISM: Flavivirus

<400> SEQUENCE: 188

Ile Tyr Val Gly Asp Leu Ser Gln
1               5

<210> SEQ ID NO 189
<211> LENGTH: 8
<212> TYPE: PRT
<213> ORGANISM: Flavivirus

<400> SEQUENCE: 189

Ile Tyr Val Gly Asp Leu Ser Gln
1               5

<210> SEQ ID NO 190
<211> LENGTH: 8
<212> TYPE: PRT
<213> ORGANISM: Flavivirus

<400> SEQUENCE: 190

Ile Lys Ile Gly Asp Leu Lys Gln
1               5

<210> SEQ ID NO 191
<211> LENGTH: 8
<212> TYPE: PRT
<213> ORGANISM: Flavivirus

<400> SEQUENCE: 191

Ile Tyr Val Gly Thr Leu Ala His
1               5

<210> SEQ ID NO 192
<211> LENGTH: 8
<212> TYPE: PRT
<213> ORGANISM: Flavivirus

<400> SEQUENCE: 192

Ile Tyr Ile Gly Asn Leu His Gln
1               5

<210> SEQ ID NO 193
<211> LENGTH: 12
<212> TYPE: PRT
<213> ORGANISM: Flavivirus

<400> SEQUENCE: 193

Ile Ile Ile Gly Val Glu Pro Gly Gln Leu Lys Leu

-continued 1 5 10

<210> SEQ ID NO 194
<211> LENGTH: 12
<212> TYPE: PRT
<213> ORGANISM: Flavivirus

<400> SEQUENCE: 194

Ile Val Ile Gly Ala Gly Glu Lys Ala Leu Lys Leu
1 5 10

<210> SEQ ID NO 195
<211> LENGTH: 12
<212> TYPE: PRT
<213> ORGANISM: Flavivirus

<400> SEQUENCE: 195

Ile Val Ile Gly Ile Gly Asp Lys Ala Leu Lys Ile
1 5 10

<210> SEQ ID NO 196
<211> LENGTH: 12
<212> TYPE: PRT
<213> ORGANISM: Flavivirus

<400> SEQUENCE: 196

Ile Val Ile Gly Val Gly Asp Ser Ala Leu Thr Leu
1 5 10

<210> SEQ ID NO 197
<211> LENGTH: 12
<212> TYPE: PRT
<213> ORGANISM: Flavivirus

<400> SEQUENCE: 197

Ile Leu Val Gly Gln Glu Asn Asn Gln Ile Lys Tyr
1 5 10

<210> SEQ ID NO 198
<211> LENGTH: 12
<212> TYPE: PRT
<213> ORGANISM: Flavivirus

<400> SEQUENCE: 198

Ile Leu Val Gly Thr Gly Pro Asn Gln Val Lys Tyr
1 5 10

<210> SEQ ID NO 199
<211> LENGTH: 12
<212> TYPE: PRT
<213> ORGANISM: Flavivirus

<400> SEQUENCE: 199

Ile Val Val Gly Arg Gly Asp Lys Gln Ile Asn His
1 5 10

<210> SEQ ID NO 200
<211> LENGTH: 12
<212> TYPE: PRT
<213> ORGANISM: Flavivirus

<400> SEQUENCE: 200

Ile Val Val Gly Arg Gly Glu Gln Gln Ile Asn His
1 5 10

<210> SEQ ID NO 201
<211> LENGTH: 12
<212> TYPE: PRT
<213> ORGANISM: Flavivirus

<400> SEQUENCE: 201

Ile Val Val Gly Arg Gly Thr Thr Gln Ile Asn Tyr
1 5 10

<210> SEQ ID NO 202
<211> LENGTH: 12
<212> TYPE: PRT
<213> ORGANISM: Flavivirus

<400> SEQUENCE: 202

Ile Ile Val Gly Thr Gly Asp Ser Arg Leu Thr Tyr
1 5 10

<210> SEQ ID NO 203
<211> LENGTH: 8
<212> TYPE: PRT
<213> ORGANISM: Flavivirus

<400> SEQUENCE: 203

Ile Lys Ile Gly Asp Ile Asp Val
1 5

<210> SEQ ID NO 204
<211> LENGTH: 8
<212> TYPE: PRT
<213> ORGANISM: Flavivirus

<400> SEQUENCE: 204

Ile Lys Val Gly Ala Ala Lys Gln
1 5

<210> SEQ ID NO 205
<211> LENGTH: 8
<212> TYPE: PRT
<213> ORGANISM: Flavivirus

<400> SEQUENCE: 205

Ile Lys Val Gly Gly Ala Val Phe
1 5

<210> SEQ ID NO 206
<211> LENGTH: 8
<212> TYPE: PRT
<213> ORGANISM: Flavivirus

<400> SEQUENCE: 206

Ile Lys Val Gly Asp Ile Thr Tyr
1 5

<210> SEQ ID NO 207
<211> LENGTH: 8
<212> TYPE: PRT
<213> ORGANISM: Flavivirus

<400> SEQUENCE: 207

Glu Pro His Thr Gly Asp Tyr Leu
1 5

<210> SEQ ID NO 208

-continued

<211> LENGTH: 8
<212> TYPE: PRT
<213> ORGANISM: Flavivirus

<400> SEQUENCE: 208

Glu Pro His Thr Gly Asp Tyr Leu
1 5

<210> SEQ ID NO 209
<211> LENGTH: 8
<212> TYPE: PRT
<213> ORGANISM: Flavivirus

<400> SEQUENCE: 209

Glu Pro His Thr Gly Asp Tyr Val
1 5

<210> SEQ ID NO 210
<211> LENGTH: 8
<212> TYPE: PRT
<213> ORGANISM: Flavivirus

<400> SEQUENCE: 210

Glu Pro His Thr Gly Asp Tyr Val
1 5

<210> SEQ ID NO 211
<211> LENGTH: 8
<212> TYPE: PRT
<213> ORGANISM: Flavivirus

<400> SEQUENCE: 211

Glu Pro His Thr Gly Asp Tyr Val
1 5

<210> SEQ ID NO 212
<211> LENGTH: 8
<212> TYPE: PRT
<213> ORGANISM: Flavivirus

<400> SEQUENCE: 212

Glu Pro His Thr Gly Asp Tyr Val
1 5

<210> SEQ ID NO 213
<211> LENGTH: 8
<212> TYPE: PRT
<213> ORGANISM: Flavivirus

<400> SEQUENCE: 213

Glu Pro His Thr Gly Asn Tyr Val
1 5

<210> SEQ ID NO 214
<211> LENGTH: 8
<212> TYPE: PRT
<213> ORGANISM: Flavivirus

<400> SEQUENCE: 214

Glu Pro His Thr Gly Glu Phe Val
1 5

<210> SEQ ID NO 215
<211> LENGTH: 8
<212> TYPE: PRT

<213> ORGANISM: Flavivirus

<400> SEQUENCE: 215

Glu Pro His Thr Gly Asp Tyr Gln
1               5

<210> SEQ ID NO 216
<211> LENGTH: 8
<212> TYPE: PRT
<213> ORGANISM: Flavivirus

<400> SEQUENCE: 216

Glu Pro His Thr Gly Asp Tyr Leu
1               5

<210> SEQ ID NO 217
<211> LENGTH: 8
<212> TYPE: PRT
<213> ORGANISM: Flavivirus

<400> SEQUENCE: 217

Glu Pro His Thr Gly Thr Tyr Leu
1               5

<210> SEQ ID NO 218
<211> LENGTH: 8
<212> TYPE: PRT
<213> ORGANISM: Flavivirus

<400> SEQUENCE: 218

Glu Pro His Thr Gly Asp His Lys
1               5

<210> SEQ ID NO 219
<211> LENGTH: 8
<212> TYPE: PRT
<213> ORGANISM: Flavivirus

<400> SEQUENCE: 219

Glu Pro His Thr Gly Thr Tyr Val
1               5

<210> SEQ ID NO 220
<211> LENGTH: 9
<212> TYPE: PRT
<213> ORGANISM: Flavivirus

<400> SEQUENCE: 220

Thr Pro His Ser Gly Glu Glu His Ala
1               5

<210> SEQ ID NO 221
<211> LENGTH: 9
<212> TYPE: PRT
<213> ORGANISM: Flavivirus

<400> SEQUENCE: 221

Thr Val His Thr Gly Asp Gln His Gln
1               5

<210> SEQ ID NO 222
<211> LENGTH: 9
<212> TYPE: PRT
<213> ORGANISM: Flavivirus

-continued

<400> SEQUENCE: 222

Thr Val His Thr Gly Asp Gln His Gln
1 5

<210> SEQ ID NO 223
<211> LENGTH: 9
<212> TYPE: PRT
<213> ORGANISM: Flavivirus

<400> SEQUENCE: 223

Thr Val His Asn Gly Asp Thr His Ala
1 5

<210> SEQ ID NO 224
<211> LENGTH: 14
<212> TYPE: PRT
<213> ORGANISM: Flavivirus

<400> SEQUENCE: 224

Tyr Val His Gly Pro Ile Ser Ala Ala Ala His Gly Asn Tyr
1 5 10

<210> SEQ ID NO 225
<211> LENGTH: 14
<212> TYPE: PRT
<213> ORGANISM: Flavivirus

<400> SEQUENCE: 225

Tyr Val His Gly Pro Thr Ser Val Ala Ala His Gly Asn Tyr
1 5 10

<210> SEQ ID NO 226
<211> LENGTH: 14
<212> TYPE: PRT
<213> ORGANISM: Flavivirus

<400> SEQUENCE: 226

Phe Val His Gly Thr Thr Thr Ser Glu Asn His Gly Asn Tyr
1 5 10

<210> SEQ ID NO 227
<211> LENGTH: 14
<212> TYPE: PRT
<213> ORGANISM: Flavivirus

<400> SEQUENCE: 227

Phe Val His Gly Pro Thr Thr Val Glu Ser His Gly Asn Tyr
1 5 10

<210> SEQ ID NO 228
<211> LENGTH: 14
<212> TYPE: PRT
<213> ORGANISM: Flavivirus

<400> SEQUENCE: 228

Phe Val His Gly Ser Thr Asp Ser Thr Ser His Gly Asn Tyr
1 5 10

<210> SEQ ID NO 229
<211> LENGTH: 6
<212> TYPE: PRT
<213> ORGANISM: Flavivirus

<400> SEQUENCE: 229

Gln Leu His Val Gly Ala
1 5

<210> SEQ ID NO 230
<211> LENGTH: 7
<212> TYPE: PRT
<213> ORGANISM: Flavivirus

<400> SEQUENCE: 230

Glu Val His Lys Gly Asn Leu
1 5

<210> SEQ ID NO 231
<211> LENGTH: 7
<212> TYPE: PRT
<213> ORGANISM: Flavivirus

<400> SEQUENCE: 231

Glu Val His Lys Gly Glu Leu
1 5

<210> SEQ ID NO 232
<211> LENGTH: 7
<212> TYPE: PRT
<213> ORGANISM: Flavivirus

<400> SEQUENCE: 232

Glu Val His Gln Gly Lys Leu
1 5

<210> SEQ ID NO 233
<211> LENGTH: 7
<212> TYPE: PRT
<213> ORGANISM: Flavivirus

<400> SEQUENCE: 233

Glu Val His Arg Gly Glu Val
1 5

<210> SEQ ID NO 234
<211> LENGTH: 8
<212> TYPE: PRT
<213> ORGANISM: Flavivirus

<400> SEQUENCE: 234

Glu Gly Ala His Glu Trp Asn His
1 5

<210> SEQ ID NO 235
<211> LENGTH: 8
<212> TYPE: PRT
<213> ORGANISM: Flavivirus

<400> SEQUENCE: 235

Gly Gly Ala Gln Glu Trp Asn His
1 5

<210> SEQ ID NO 236
<211> LENGTH: 8
<212> TYPE: PRT
<213> ORGANISM: Flavivirus

<400> SEQUENCE: 236

Glu Gly Ala Gln Asn Trp Asn Asn
1 5

<210> SEQ ID NO 237
<211> LENGTH: 8
<212> TYPE: PRT
<213> ORGANISM: Flavivirus

<400> SEQUENCE: 237

Glu Gly Ala Leu Gly Trp Asn Asn
1               5

<210> SEQ ID NO 238
<211> LENGTH: 8
<212> TYPE: PRT
<213> ORGANISM: Flavivirus

<400> SEQUENCE: 238

Asp Gly Asn Pro His Trp Asn Asn
1               5

<210> SEQ ID NO 239
<211> LENGTH: 8
<212> TYPE: PRT
<213> ORGANISM: Flavivirus

<400> SEQUENCE: 239

Glu Gly Ala Gln Arg Trp Asn Asn
1               5

<210> SEQ ID NO 240
<211> LENGTH: 8
<212> TYPE: PRT
<213> ORGANISM: Flavivirus

<400> SEQUENCE: 240

Glu Gly Met Val Gly Trp Asn Asn
1               5

<210> SEQ ID NO 241
<211> LENGTH: 8
<212> TYPE: PRT
<213> ORGANISM: Flavivirus

<400> SEQUENCE: 241

Asp Gly Ala Glu Ala Trp Asn Glu
1               5

<210> SEQ ID NO 242
<211> LENGTH: 8
<212> TYPE: PRT
<213> ORGANISM: Flavivirus

<400> SEQUENCE: 242

Lys Asp Asn Gln Asp Trp Asn Ser
1               5

<210> SEQ ID NO 243
<211> LENGTH: 8
<212> TYPE: PRT
<213> ORGANISM: Flavivirus

<400> SEQUENCE: 243

Lys Asp Asn Gln Asp Trp Asn Ser
1               5

<210> SEQ ID NO 244
<211> LENGTH: 8
<212> TYPE: PRT
<213> ORGANISM: Flavivirus

<400> SEQUENCE: 244

Lys Gly Glu Ser Ala Trp Arg Glu
1               5

<210> SEQ ID NO 245
<211> LENGTH: 8
<212> TYPE: PRT
<213> ORGANISM: Flavivirus

<400> SEQUENCE: 245

Val Gly Ala Glu Thr Trp Asn Tyr
1               5

<210> SEQ ID NO 246
<211> LENGTH: 8
<212> TYPE: PRT
<213> ORGANISM: Flavivirus

<400> SEQUENCE: 246

His Glu Ala Glu Ile Trp Glu Asp
1               5

<210> SEQ ID NO 247
<211> LENGTH: 11
<212> TYPE: PRT
<213> ORGANISM: Flavivirus

<400> SEQUENCE: 247

Gly Ala Asp Thr Gln Gly Ser Asn Trp Ile Gln
1               5                   10

<210> SEQ ID NO 248
<211> LENGTH: 11
<212> TYPE: PRT
<213> ORGANISM: Flavivirus

<400> SEQUENCE: 248

Gly Ala Ser Thr Ser Gln Glu Thr Trp Asn Arg
1               5                   10

<210> SEQ ID NO 249
<211> LENGTH: 11
<212> TYPE: PRT
<213> ORGANISM: Flavivirus

<400> SEQUENCE: 249

Gly Ala Thr Thr Glu Thr Pro Thr Trp Asn Arg
1               5                   10

<210> SEQ ID NO 250
<211> LENGTH: 11
<212> TYPE: PRT
<213> ORGANISM: Flavivirus

<400> SEQUENCE: 250

Gly Ala Asp Thr Ser Glu Val His Trp Asn Tyr
1               5                   10

<210> SEQ ID NO 251
<211> LENGTH: 8

<212> TYPE: PRT
<213> ORGANISM: Flavivirus

<400> SEQUENCE: 251

Pro Ala Thr Glu Ser Trp Lys Asn
1 5

<210> SEQ ID NO 252
<211> LENGTH: 8
<212> TYPE: PRT
<213> ORGANISM: Flavivirus

<400> SEQUENCE: 252

Pro Ala Thr Asp Val Trp Lys Tyr
1 5

<210> SEQ ID NO 253
<211> LENGTH: 8
<212> TYPE: PRT
<213> ORGANISM: Flavivirus

<400> SEQUENCE: 253

Pro Ser Ser Thr Ala Trp Arg Asn
1 5

<210> SEQ ID NO 254
<211> LENGTH: 8
<212> TYPE: PRT
<213> ORGANISM: Flavivirus

<400> SEQUENCE: 254

Ala Gly Ser Thr Val Trp Arg Asn
1 5

<210> SEQ ID NO 255
<211> LENGTH: 8
<212> TYPE: PRT
<213> ORGANISM: Flavivirus

<400> SEQUENCE: 255

Pro Ala Thr Thr Asp Trp Arg Asn
1 5

<210> SEQ ID NO 256
<211> LENGTH: 8
<212> TYPE: PRT
<213> ORGANISM: Flavivirus

<400> SEQUENCE: 256

Gly Ser Gly Gly Val Trp Arg Glu
1 5

<210> SEQ ID NO 257
<211> LENGTH: 7
<212> TYPE: PRT
<213> ORGANISM: Flavivirus

<400> SEQUENCE: 257

Pro Lys Gly Lys Trp Lys Asp
1 5

<210> SEQ ID NO 258
<211> LENGTH: 7
<212> TYPE: PRT
<213> ORGANISM: Flavivirus

<400> SEQUENCE: 258

Pro Asp Gly His Trp His Asp
1 5

<210> SEQ ID NO 259
<211> LENGTH: 7
<212> TYPE: PRT
<213> ORGANISM: Flavivirus

<400> SEQUENCE: 259

Ser Gly Gly Ser Trp His Gly
1 5

<210> SEQ ID NO 260
<211> LENGTH: 7
<212> TYPE: PRT
<213> ORGANISM: Flavivirus

<400> SEQUENCE: 260

Asn Ala Gly Pro Trp Arg Gly
1 5

<210> SEQ ID NO 261
<211> LENGTH: 8
<212> TYPE: PRT
<213> ORGANISM: Flavivirus

<400> SEQUENCE: 261

Met Glu Thr Thr Gly Gly Gly Phe
1 5

<210> SEQ ID NO 262
<211> LENGTH: 8
<212> TYPE: PRT
<213> ORGANISM: Flavivirus

<400> SEQUENCE: 262

Met Glu Thr Thr Gly Gly Gly Phe
1 5

<210> SEQ ID NO 263
<211> LENGTH: 8
<212> TYPE: PRT
<213> ORGANISM: Flavivirus

<400> SEQUENCE: 263

Ile Glu Asn Asn Gly Gly Gly Phe
1 5

<210> SEQ ID NO 264
<211> LENGTH: 8
<212> TYPE: PRT
<213> ORGANISM: Flavivirus

<400> SEQUENCE: 264

Ile Glu Asn Ser Gly Gly Gly Phe
1 5

<210> SEQ ID NO 265
<211> LENGTH: 8
<212> TYPE: PRT
<213> ORGANISM: Flavivirus

<400> SEQUENCE: 265

Ile Glu Asn Asp Gly Gly Gly Phe
1 5

<210> SEQ ID NO 266
<211> LENGTH: 8
<212> TYPE: PRT
<213> ORGANISM: Flavivirus

<400> SEQUENCE: 266

Ile Glu Asn Glu Gly Gly Gly Phe
1 5

<210> SEQ ID NO 267
<211> LENGTH: 8
<212> TYPE: PRT
<213> ORGANISM: Flavivirus

<400> SEQUENCE: 267

Met Glu Asn Asn Gly Gly Gly Phe
1 5

<210> SEQ ID NO 268
<211> LENGTH: 8
<212> TYPE: PRT
<213> ORGANISM: Flavivirus

<400> SEQUENCE: 268

Met Glu Asn Asn Gly Gly Gly Phe
1 5

<210> SEQ ID NO 269
<211> LENGTH: 8
<212> TYPE: PRT
<213> ORGANISM: Flavivirus

<400> SEQUENCE: 269

Ile Glu Thr Ser Gly Gly Gly Phe
1 5

<210> SEQ ID NO 270
<211> LENGTH: 8
<212> TYPE: PRT
<213> ORGANISM: Flavivirus

<400> SEQUENCE: 270

Ile Glu Thr Asn Gly Gly Gly Phe
1 5

<210> SEQ ID NO 271
<211> LENGTH: 8
<212> TYPE: PRT
<213> ORGANISM: Flavivirus

<400> SEQUENCE: 271

Ile Glu Thr Asp Lys Gly Gly Phe
1 5

<210> SEQ ID NO 272
<211> LENGTH: 8
<212> TYPE: PRT
<213> ORGANISM: Flavivirus

<400> SEQUENCE: 272

Ile Glu Thr Ala Gly Gly Gly Phe 1 5

<210> SEQ ID NO 273
<211> LENGTH: 8
<212> TYPE: PRT
<213> ORGANISM: Flavivirus

<400> SEQUENCE: 273

Ile Glu Asn Glu Gly Gly Gly Tyr
1 5

<210> SEQ ID NO 274
<211> LENGTH: 9
<212> TYPE: PRT
<213> ORGANISM: Flavivirus

<400> SEQUENCE: 274

Val Thr Glu Lys Asp Ser Pro Val Asn
1 5

<210> SEQ ID NO 275
<211> LENGTH: 9
<212> TYPE: PRT
<213> ORGANISM: Flavivirus

<400> SEQUENCE: 275

Val Thr Asp Lys Glu Lys Pro Val Asn
1 5

<210> SEQ ID NO 276
<211> LENGTH: 9
<212> TYPE: PRT
<213> ORGANISM: Flavivirus

<400> SEQUENCE: 276

Val Thr Lys Lys Glu Glu Pro Val Asn
1 5

<210> SEQ ID NO 277
<211> LENGTH: 9
<212> TYPE: PRT
<213> ORGANISM: Flavivirus

<400> SEQUENCE: 277

Ala Glu Asn Thr Asn Ser Val Thr Asn
1 5

<210> SEQ ID NO 278
<211> LENGTH: 11
<212> TYPE: PRT
<213> ORGANISM: Flavivirus

<400> SEQUENCE: 278

Ile Pro Ser Ser Ala Lys Ser Gln Lys Ile Leu
1 5 10

<210> SEQ ID NO 279
<211> LENGTH: 11
<212> TYPE: PRT
<213> ORGANISM: Flavivirus

<400> SEQUENCE: 279

Val Pro Ser Ser Glu Thr Ala Gln Lys Ile Leu
1 5 10

-continued

<210> SEQ ID NO 280
<211> LENGTH: 11
<212> TYPE: PRT
<213> ORGANISM: Flavivirus

<400> SEQUENCE: 280

Val Ala Thr Ser Ser Ala Asn Ser Lys Val Leu
1 5 10

<210> SEQ ID NO 281
<211> LENGTH: 11
<212> TYPE: PRT
<213> ORGANISM: Flavivirus

<400> SEQUENCE: 281

Val Ser Val Ala Thr Ala Asn Ala Lys Val Leu
1 5 10

<210> SEQ ID NO 282
<211> LENGTH: 11
<212> TYPE: PRT
<213> ORGANISM: Flavivirus

<400> SEQUENCE: 282

Ile Ser Thr Gly Gly Ala Asn Asn Lys Val Met
1 5 10

<210> SEQ ID NO 283
<211> LENGTH: 9
<212> TYPE: PRT
<213> ORGANISM: Flavivirus

<400> SEQUENCE: 283

Ala Ser Thr Asn Asp Asp Glu Val Leu
1 5

<210> SEQ ID NO 284
<211> LENGTH: 9
<212> TYPE: PRT
<213> ORGANISM: Flavivirus

<400> SEQUENCE: 284

Ala Ser Gln Lys Asp Ala Val Val Phe
1 5

<210> SEQ ID NO 285
<211> LENGTH: 9
<212> TYPE: PRT
<213> ORGANISM: Flavivirus

<400> SEQUENCE: 285

Ile Thr Ala Gln Gly Ser Ser Val Phe
1 5

<210> SEQ ID NO 286
<211> LENGTH: 9
<212> TYPE: PRT
<213> ORGANISM: Flavivirus

<400> SEQUENCE: 286

Ala Ala Asn Asn Glu Ala Val Val Phe
1 5

<210> SEQ ID NO 287

<211> LENGTH: 9
<212> TYPE: PRT
<213> ORGANISM: Flavivirus

<400> SEQUENCE: 287

Val Glu Ser Asn Gly Ala Thr Ile Phe
1 5

<210> SEQ ID NO 288
<211> LENGTH: 12
<212> TYPE: PRT
<213> ORGANISM: Flavivirus

<400> SEQUENCE: 288

Val Leu Ser Ser Val Gly Lys Ala Leu His Thr Ala
1 5 10

<210> SEQ ID NO 289
<211> LENGTH: 12
<212> TYPE: PRT
<213> ORGANISM: Flavivirus

<400> SEQUENCE: 289

Met Leu Ser Ser Val Gly Lys Ala Leu His Thr Ala
1 5 10

<210> SEQ ID NO 290
<211> LENGTH: 12
<212> TYPE: PRT
<213> ORGANISM: Flavivirus

<400> SEQUENCE: 290

Phe Leu Thr Ser Val Gly Lys Ala Leu His Thr Val
1 5 10

<210> SEQ ID NO 291
<211> LENGTH: 12
<212> TYPE: PRT
<213> ORGANISM: Flavivirus

<400> SEQUENCE: 291

Phe Leu Thr Ser Ile Gly Lys Ala Met His Thr Val
1 5 10

<210> SEQ ID NO 292
<211> LENGTH: 12
<212> TYPE: PRT
<213> ORGANISM: Flavivirus

<400> SEQUENCE: 292

Phe Phe Gly Ser Ile Gly Lys Ala Val His Thr Val
1 5 10

<210> SEQ ID NO 293
<211> LENGTH: 12
<212> TYPE: PRT
<213> ORGANISM: Flavivirus

<400> SEQUENCE: 293

Phe Leu Ser Ser Ile Gly Lys Ala Val His Thr Val
1 5 10

<210> SEQ ID NO 294
<211> LENGTH: 12
<212> TYPE: PRT

<213> ORGANISM: Flavivirus

<400> SEQUENCE: 294

Phe Leu Ser Ser Ile Gly Lys Ala Val His Thr Val
1 5 10

<210> SEQ ID NO 295
<211> LENGTH: 12
<212> TYPE: PRT
<213> ORGANISM: Flavivirus

<400> SEQUENCE: 295

Val Met Thr Ser Ile Gly Arg Ala Met His Thr Val
1 5 10

<210> SEQ ID NO 296
<211> LENGTH: 12
<212> TYPE: PRT
<213> ORGANISM: Flavivirus

<400> SEQUENCE: 296

Ile Leu Ser Ser Val Gly Lys Ala Val His Thr Val
1 5 10

<210> SEQ ID NO 297
<211> LENGTH: 12
<212> TYPE: PRT
<213> ORGANISM: Flavivirus

<400> SEQUENCE: 297

Val Leu Ser Ser Val Gly Lys Ala Ile His Thr Val
1 5 10

<210> SEQ ID NO 298
<211> LENGTH: 12
<212> TYPE: PRT
<213> ORGANISM: Flavivirus

<400> SEQUENCE: 298

Val Phe Ser Ser Val Ala Lys Ala Cys His Met Val
1 5 10

<210> SEQ ID NO 299
<211> LENGTH: 12
<212> TYPE: PRT
<213> ORGANISM: Flavivirus

<400> SEQUENCE: 299

Val Phe Ser Ser Val Gly Lys Ala Thr His Met Val
1 5 10

<210> SEQ ID NO 300
<211> LENGTH: 12
<212> TYPE: PRT
<213> ORGANISM: Flavivirus

<400> SEQUENCE: 300

Phe Phe Gly Ser Ile Gly Lys Ala Val His Met Val
1 5 10

<210> SEQ ID NO 301
<211> LENGTH: 12
<212> TYPE: PRT
<213> ORGANISM: Flavivirus

<400> SEQUENCE: 301

Val Phe Thr Ser Ile Gly Lys Ala Leu His Gln Val
1 5 10

<210> SEQ ID NO 302
<211> LENGTH: 12
<212> TYPE: PRT
<213> ORGANISM: Flavivirus

<400> SEQUENCE: 302

Val Phe Thr Ser Val Gly Lys Leu Val His Gln Ile
1 5 10

<210> SEQ ID NO 303
<211> LENGTH: 12
<212> TYPE: PRT
<213> ORGANISM: Flavivirus

<400> SEQUENCE: 303

Val Leu Asn Ser Leu Gly Lys Asn Val His Gln Ile
1 5 10

<210> SEQ ID NO 304
<211> LENGTH: 12
<212> TYPE: PRT
<213> ORGANISM: Flavivirus

<400> SEQUENCE: 304

Leu Phe Thr Ser Leu Gly Lys Ala Val His Gln Val
1 5 10

<210> SEQ ID NO 305
<211> LENGTH: 12
<212> TYPE: PRT
<213> ORGANISM: Flavivirus

<400> SEQUENCE: 305

Ile Phe Asn Ser Ile Gly Lys Thr Ile His Gly Val
1 5 10

<210> SEQ ID NO 306
<211> LENGTH: 12
<212> TYPE: PRT
<213> ORGANISM: Flavivirus

<400> SEQUENCE: 306

Val Phe Asn Ser Ile Gly Lys Gly Ile His Gly Leu
1 5 10

<210> SEQ ID NO 307
<211> LENGTH: 12
<212> TYPE: PRT
<213> ORGANISM: Flavivirus

<400> SEQUENCE: 307

Val Phe Asn Ser Ile Gly Lys Ala Val His Gln Val
1 5 10

<210> SEQ ID NO 308
<211> LENGTH: 12
<212> TYPE: PRT
<213> ORGANISM: Flavivirus

<400> SEQUENCE: 308

Val Phe Thr Ser Val Gly Lys Ala Val His Gln Val
1 5 10

<210> SEQ ID NO 309
<211> LENGTH: 12
<212> TYPE: PRT
<213> ORGANISM: Flavivirus

<400> SEQUENCE: 309

Val Phe Asn Ser Ile Gly Lys Ala Val His Gln Val
1 5 10

<210> SEQ ID NO 310
<211> LENGTH: 12
<212> TYPE: PRT
<213> ORGANISM: Flavivirus

<400> SEQUENCE: 310

Phe Phe Thr Ser Val Gly Lys Gly Ile His Thr Val
1 5 10

<210> SEQ ID NO 311
<211> LENGTH: 7
<212> TYPE: PRT
<213> ORGANISM: Flavivirus

<400> SEQUENCE: 311

Phe Ser Asn Leu Ile Ser Ile
1 5

<210> SEQ ID NO 312
<211> LENGTH: 7
<212> TYPE: PRT
<213> ORGANISM: Flavivirus

<400> SEQUENCE: 312

Ser Phe Ser Leu Met Arg Met
1 5

<210> SEQ ID NO 313
<211> LENGTH: 7
<212> TYPE: PRT
<213> ORGANISM: Flavivirus

<400> SEQUENCE: 313

Ser Ala Gly Ile Met Arg Ile
1 5

<210> SEQ ID NO 314
<211> LENGTH: 7
<212> TYPE: PRT
<213> ORGANISM: Flavivirus

<400> SEQUENCE: 314

Ala Ile Asn Leu Met Asp Leu
1 5

<210> SEQ ID NO 315
<211> LENGTH: 495
<212> TYPE: PRT
<213> ORGANISM: Flavivirus

<400> SEQUENCE: 315

Met Arg Cys Val Gly Val Gly Asn Arg Asp Phe Val Glu Gly Val Ser
1 5 10 15

-continued

```
Asp Ala Thr Trp Val Asp Val Val Leu Glu His Gly Gly Cys Val Thr
            20                  25                  30

Thr Met Ala Lys Asn Lys Pro Thr Leu Asp Phe Glu Leu Leu Lys Thr
        35                  40                  45

Glu Ala Lys Gln Val Ala Thr Leu Arg Lys Leu Cys Ile Glu Ala Lys
    50                  55                  60

Ile Ser Asn Ile Thr Thr Glu Ser Arg Cys Pro Thr Gln Gly Glu Ala
65                  70                  75                  80

Thr Leu Asn Glu Glu Gln Asp Gln Gln Tyr Val Cys Arg His Ser Phe
                85                  90                  95

Val Asp Arg Gly Trp Gly Asn Gly Cys Gly Leu Phe Gly Lys Gly Gly
            100                 105                 110

Leu Val Thr Cys Ala Lys Phe Gln Cys Val Thr Lys Ile Glu Gly Lys
        115                 120                 125

Val Val Gln Tyr Glu Asn Leu Glu Tyr Thr Val Val Val Thr Val His
    130                 135                 140

Ser Gly Asp Gln His Gln Val Gly Asn Glu Thr Ser Asn His Gly Thr
145                 150                 155                 160

Thr Ala Lys Ile Thr Pro Gln Ala Pro Thr Thr Glu Val Gln Leu Thr
                165                 170                 175

Asp Tyr Gly Thr Leu Thr Leu Glu Cys Ser Pro Arg Thr Gly Leu Asp
            180                 185                 190

Phe Asn Glu Met Val Leu Leu Gln Met Lys Asn Lys Thr Trp Leu Val
        195                 200                 205

His Arg Gln Trp Phe Leu Asp Leu Pro Leu Pro Trp Thr Ser Gly Ala
    210                 215                 220

Ser Thr Gln Gln Ser Thr Trp Asn Gln Lys Glu Thr Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Asn
            260                 265                 270

Ser Ser Gly Asn Thr Ile Phe Ala Gly His Leu Lys Cys Arg Leu Arg
        275                 280                 285

Met Asp Lys Leu Gln Leu Lys Gly Met Ser Tyr Thr Met Cys Thr Gly
    290                 295                 300

Lys Phe Lys Ile Glu Lys Glu Val Ala Glu Thr Gln His Gly Thr Val
305                 310                 315                 320

Val Val Lys Val Lys Tyr Glu Gly Glu Asp Ala Pro Cys Lys Ile Pro
                325                 330                 335

Phe Glu Ile Gln Asp Leu Gln Gly Lys Thr His Asn Gly Arg Leu Ile
            340                 345                 350

Thr Ala Asn Pro Ile Val Thr Asn Lys Asp Ser Pro Val Asn Ile Glu
        355                 360                 365

Ala Glu Pro Pro Phe Gly Glu Ser Tyr Ile Val Ile Gly Val Gly Asp
    370                 375                 380

Ser Ala Leu Lys Ile Asn Trp Phe Lys Lys Gly Ser Ser Ile Gly Lys
385                 390                 395                 400

Met Phe Glu Thr Thr Ala Arg Gly Ala Arg Arg Met Ala Ile Leu Gly
                405                 410                 415

Asp Thr Ala Trp Asp Phe Gly Ser Val Gly Gly Val Phe Thr Ser Leu
            420                 425                 430
```

Gly Lys Ala Val His Gln Val Phe Gly Thr Val Tyr Gly Ala Leu Phe
435 440 445

Ser Gly Val Ser Trp Met Met Lys Ile Gly Ile Gly Val Leu Leu Thr
450 455 460

Trp Ile Gly Met Asn Ser Arg Ser Thr Ser Met Ser Met Ser Cys Ile
465 470 475 480

Leu Val Gly Val Val Thr Leu Tyr Leu Gly Val Met Val Gln Ala
485 490 495

<210> SEQ ID NO 316
<211> LENGTH: 495
<212> TYPE: PRT
<213> ORGANISM: Flavivirus

<400> SEQUENCE: 316

Met Arg Cys Val Gly Val Gly Asn Arg Asp Phe Val Glu Gly Val Ser
1 5 10 15

Gly Ala Thr Trp Val Asp Val Val Leu Glu His Gly Gly Cys Val Thr
20 25 30

Thr Met Ala Lys Asn Lys Pro Thr Leu Asp Phe Glu Leu Leu Lys Thr
35 40 45

Glu Ala Lys Gln Val Ala Thr Leu Arg Lys Leu Cys Ile Glu Ala Lys
50 55 60

Ile Ser Asn Val Thr Thr Glu Ser Arg Cys Pro Thr Gln Gly Glu Ala
65 70 75 80

Thr Leu Lys Glu Glu Gln Asp Gln Gln Tyr Val Cys Arg His Ser Phe
85 90 95

Val Asp Arg Gly Trp Gly Asn Gly Cys Gly Leu Phe Gly Lys Gly Gly
100 105 110

Leu Val Thr Cys Ala Lys Phe Gln Cys Val Thr Lys Ile Glu Gly Lys
115 120 125

Val Val Gln His Glu Asn Leu Glu Tyr Thr Val Val Val Thr Val His
130 135 140

Ser Gly Asp Gln His Gln Val Gly Asn Glu Thr Ser Asn His Gly Thr
145 150 155 160

Thr Ala Lys Ile Thr Pro Gln Ala Pro Thr Thr Glu Val Gln Leu Thr
165 170 175

Asp Tyr Gly Thr Leu Ser Leu Glu Cys Ser Pro Arg Thr Gly Leu Asp
180 185 190

Phe Asn Glu Met Val Leu Leu Gln Met Lys Asn Lys Thr Trp Leu Val
195 200 205

His Arg Gln Trp Phe Leu Asp Leu Pro Leu Pro Trp Thr Ser Gly Ala
210 215 220

Ser Thr Gln Gln Ser Thr Trp Asn Gln Lys Glu Thr Leu Val Thr Phe
225 230 235 240

Lys Thr Ala His Ala Lys Lys Gln Glu Val Val Val Leu Gly Ser Gln
245 250 255

Glu Gly Ala Met His Thr Ala Leu Thr Gly Ala Thr Glu Ile Cys Thr
260 265 270

Ser Ser Gly Asn Thr Ile Phe Ala Gly His Leu Lys Cys Arg Leu Arg
275 280 285

Met Asp Lys Leu Gln Leu Lys Gly Met Ser Tyr Thr Met Cys Thr Gly
290 295 300

Lys Phe Lys Leu Glu Lys Glu Val Ala Glu Thr Gln His Gly Thr Val
305 310 315 320

```
Val Val Lys Val Lys Tyr Glu Gly Glu Asp Ala Pro Cys Lys Ile Pro
                325                 330                 335

Phe Glu Ile Gln Asp Leu Gln Gly Lys Thr His Asn Gly Arg Leu Ile
            340                 345                 350

Thr Ala Asn Pro Ile Val Thr Asn Lys Asp Ser Pro Val Asn Ile Glu
        355                 360                 365

Ala Glu Pro Pro Phe Gly Glu Ser Tyr Ile Val Ile Gly Val Gly Asp
    370                 375                 380

Ser Ala Leu Lys Leu Asn Trp Phe Lys Lys Gly Ser Ser Ile Gly Lys
385                 390                 395                 400

Met Phe Glu Thr Thr Ala Arg Gly Ala Arg Arg Met Ala Ile Leu Gly
                405                 410                 415

Asp Thr Ala Trp Asp Phe Gly Ser Val Gly Gly Val Phe Thr Ser Leu
            420                 425                 430

Gly Lys Ala Val His Gln Val Phe Gly Thr Val Tyr Gly Ala Leu Phe
        435                 440                 445

Ser Gly Val Ser Trp Met Met Lys Ile Gly Ile Gly Val Leu Leu Thr
    450                 455                 460

Trp Ile Gly Met Asn Ser Arg Ser Thr Ser Met Ser Met Ser Cys Ile
465                 470                 475                 480

Leu Val Gly Val Val Thr Leu Tyr Leu Gly Val Met Val Gln Ala
                485                 490                 495


<210> SEQ ID NO 317
<211> LENGTH: 435
<212> TYPE: PRT
<213> ORGANISM: Flavivirus

<400> SEQUENCE: 317

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Thr Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
```

```
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Leu Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Ile Gly Ala Gly Glu
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Ala Val Gly Leu Val Thr Leu Tyr Leu Gly Val Met
            420                 425                 430

Val Gln Ala
        435


<210> SEQ ID NO 318
<211> LENGTH: 493
<212> TYPE: PRT
<213> ORGANISM: Flavivirus

<400> SEQUENCE: 318

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125
```

-continued

```
Val Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Val Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Thr Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
    370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
        435                 440                 445

Val Ser Trp Ile Met Lys Ile Gly Ile Gly Val Leu Leu Thr Trp Ile
    450                 455                 460

Gly Leu Asn Ser Lys Asn Thr Ser Met Ser Phe Ser Cys Ile Val Ile
465                 470                 475                 480

Gly Ile Ile Thr Leu Tyr Leu Gly Ala Val Val Gln Ala
                485                 490


<210> SEQ ID NO 319
<211> LENGTH: 495
<212> TYPE: PRT
<213> ORGANISM: Flavivirus

<400> SEQUENCE: 319

Met Arg Cys Ile Gly Ile Ser Asn Arg Asp Phe Val Glu Gly Val Ser
1               5                   10                  15
```

```
Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430
```

```
Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Val Met Val Gln Ala
                485                 490                 495


<210> SEQ ID NO 320
<211> LENGTH: 495
<212> TYPE: PRT
<213> ORGANISM: Flavivirus

<400> SEQUENCE: 320

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320
```

```
Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Phe Ala Glu Asn Thr Asn Ser Val Thr Asn Ile Glu
        355                 360                 365

Leu Glu Pro Pro Phe Gly Asp Ser Tyr Ile Val Ile Gly Val Gly Asp
    370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445

Gly Gly Val Ser Trp Met Val Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495


<210> SEQ ID NO 321
<211> LENGTH: 112
<212> TYPE: PRT
<213> ORGANISM: Flavivirus

<400> SEQUENCE: 321

Met Asp Lys Leu Thr Leu Lys Gly Met Ser Tyr Val Met Cys Thr Gly
1               5                   10                  15

Ser Phe Lys Leu Glu Lys Glu Val Ala Glu Thr Gln His Gly Thr Val
            20                  25                  30

Leu Val Gln Ile Lys Tyr Glu Gly Thr Asp Ala Pro Cys Lys Ile Pro
        35                  40                  45

Phe Ser Thr Gln Asp Glu Lys Gly Val Thr Gln Asn Gly Arg Leu Ile
    50                  55                  60

Thr Ala Asn Pro Ile Val Thr Asp Lys Glu Lys Pro Val Asn Ile Glu
65                  70                  75                  80

Ala Glu Pro Pro Phe Gly Glu Ser Tyr Ile Val Ile Gly Ala Gly Glu
                85                  90                  95

Lys Ala Leu Lys Leu Ser Trp Phe Lys Lys Gly Ser Ser Ile Gly Lys
            100                 105                 110


<210> SEQ ID NO 322
<211> LENGTH: 112
<212> TYPE: PRT
<213> ORGANISM: Flavivirus

<400> SEQUENCE: 322

Met Lys Lys Leu Glu Leu Lys Gly Met Ser Tyr Ala Met Cys Thr Asn
1               5                   10                  15

Thr Phe Val Leu Lys Lys Glu Val Ser Glu Thr Gln His Gly Thr Ile
            20                  25                  30

Leu Ile Lys Val Glu Tyr Lys Gly Glu Asp Ala Pro Cys Lys Ile Pro
        35                  40                  45
```

-continued

Phe Ser Thr Glu Asp Gly Gln Gly Lys Ala His Asn Gly Arg Leu Ile
50 55 60

Thr Ala Asn Pro Val Val Thr Lys Lys Glu Glu Pro Val Asn Ile Glu
65 70 75 80

Ala Glu Pro Pro Phe Gly Glu Ser Asn Ile Val Ile Gly Ile Gly Asp
85 90 95

Lys Ala Leu Lys Ile Asn Trp Tyr Lys Lys Gly Ser Ser Ile Gly Lys
100 105 110

<210> SEQ ID NO 323
<211> LENGTH: 112
<212> TYPE: PRT
<213> ORGANISM: Flavivirus

<400> SEQUENCE: 323

Met Asp Lys Leu Gln Leu Lys Gly Met Ser Tyr Ser Met Cys Thr Gly
1 5 10 15

Lys Phe Lys Ile Val Lys Glu Ile Ala Glu Thr Gln His Gly Thr Ile
20 25 30

Val Ile Arg Val Gln Tyr Glu Gly Asp Gly Ser Pro Cys Lys Ile Pro
35 40 45

Phe Glu Ile Met Asp Leu Glu Lys Arg His Val Leu Gly Arg Leu Ile
50 55 60

Thr Val Asn Pro Ile Val Thr Glu Lys Asp Ser Pro Val Asn Ile Glu
65 70 75 80

Ala Glu Pro Pro Phe Gly Asp Ser Tyr Ile Ile Ile Gly Val Glu Pro
85 90 95

Gly Gln Leu Lys Leu Asn Trp Phe Lys Lys Gly Ser Ser Ile Gly Gln
100 105 110

<210> SEQ ID NO 324
<211> LENGTH: 112
<212> TYPE: PRT
<213> ORGANISM: Flavivirus

<400> SEQUENCE: 324

Met Glu Lys Leu Arg Ile Lys Gly Met Ser Tyr Thr Met Cys Ser Gly
1 5 10 15

Lys Phe Ser Ile Asp Lys Glu Met Ala Glu Thr Gln His Gly Thr Thr
20 25 30

Val Val Lys Val Lys Tyr Glu Gly Ala Gly Ala Pro Cys Lys Val Pro
35 40 45

Ile Glu Ile Arg Asp Val Asn Lys Glu Lys Val Val Gly Arg Ile Ile
50 55 60

Ser Ser Thr Pro Phe Ala Glu Asn Thr Asn Ser Val Thr Asn Ile Glu
65 70 75 80

Leu Glu Pro Pro Phe Gly Asp Ser Tyr Ile Val Ile Gly Val Gly Asp
85 90 95

Ser Ala Leu Thr Leu His Trp Phe Arg Lys Gly Ser Ser Ile Gly Lys
100 105 110

<210> SEQ ID NO 325
<211> LENGTH: 112
<212> TYPE: PRT
<213> ORGANISM: Flavivirus

<400> SEQUENCE: 325

-continued

Met Glu Lys Leu Arg Ile Lys Gly Met Ser Tyr Thr Met Cys Ser Gly
1               5                   10                  15

Lys Phe Ser Ile Asp Lys Glu Met Ala Glu Thr Gln His Gly Thr Thr
            20                  25                  30

Val Val Lys Val Lys Tyr Glu Gly Ala Gly Ala Pro Cys Lys Val Pro
        35                  40                  45

Ile Glu Ile Arg Asp Val Asn Lys Glu Lys Val Val Gly Arg Ile Ile
    50                  55                  60

Ser Ser Thr Pro Leu Ala Glu Asn Thr Asn Ser Val Thr Asn Ile Glu
65                  70                  75                  80

Leu Glu Pro Pro Phe Gly Asp Ser Tyr Ile Val Ile Gly Val Gly Asn
                85                  90                  95

Ser Ala Leu Thr Leu His Trp Phe Arg Lys Gly Ser Ser Ile Gly Lys
            100                 105                 110

<210> SEQ ID NO 326
<211> LENGTH: 112
<212> TYPE: PRT
<213> ORGANISM: Flavivirus

<400> SEQUENCE: 326

Met Asp Lys Leu Gln Leu Lys Gly Met Ser Tyr Thr Met Cys Thr Gly
1               5                   10                  15

Lys Phe Ser Ile Glu Lys Glu Val Ala Glu Thr Gln His Gly Thr Val
            20                  25                  30

Val Val Lys Val Lys Tyr Glu Gly Glu Gly Ala Pro Cys Lys Ile Pro
        35                  40                  45

Phe Glu Ile Gln Asp Leu Gln Lys Lys His Val Val Gly Arg Leu Ile
    50                  55                  60

Thr Ala Asn Pro Ile Val Thr Asn Lys Asp Ser Pro Val Asn Ile Glu
65                  70                  75                  80

Ala Glu Pro Pro Phe Gly Asp Gly Tyr Ile Val Ile Gly Val Gly Asn
                85                  90                  95

Ser Ala Leu Lys Leu Asn Trp Glu Lys Lys Gly Ser Ser Ile Gly Lys
            100                 105                 110

<210> SEQ ID NO 327
<211> LENGTH: 112
<212> TYPE: PRT
<213> ORGANISM: Flavivirus

<400> SEQUENCE: 327

Met Asp Lys Leu Gln Leu Lys Gly Met Ser Tyr Thr Met Cys Thr Gly
1               5                   10                  15

Lys Phe Ser Ile Glu Lys Glu Val Ala Glu Thr Gln His Gly Thr Val
            20                  25                  30

Val Val Lys Val Lys Tyr Glu Gly Glu Gly Ala Pro Cys Lys Ile Pro
        35                  40                  45

Phe Glu Ile Gln Asp Leu Gln Lys Glu Lys Val Val Gly Arg Leu Ile
    50                  55                  60

Thr Ala Asn Pro Ile Val Glu Asn Thr Asn Ser Pro Val Asn Ile Glu
65                  70                  75                  80

Ala Glu Pro Pro Phe Gly Asp Ser Tyr Ile Val Ile Gly Val Gly Asn
                85                  90                  95

Ser Ala Leu Lys Leu Asn Trp Phe Lys Lys Gly Ser Ser Ile Gly Lys
            100                 105                 110

<210> SEQ ID NO 328
<211> LENGTH: 116
<212> TYPE: PRT
<213> ORGANISM: Flavivirus

<400> SEQUENCE: 328

```
Met Asp Lys Leu Gln Leu Lys Gly Met Ser Tyr Thr Met Cys Thr Gly
1               5                   10                  15

Lys Phe Lys Ile Glu Lys Glu Val Ala Glu Thr Gln His Gly Thr Val
            20                  25                  30

Val Val Lys Val Lys Tyr Glu Gly Glu Asp Ala Pro Cys Lys Ile Pro
        35                  40                  45

Phe Glu Ile Gln Asp Leu Gln Lys Glu Lys Val Val Gly Arg Leu Ile
    50                  55                  60

Thr Ala Asn Pro Ile Val Glu Asn Thr Ile Asn Ser Val Asn Ile Glu
65                  70                  75                  80

Ala Glu Pro Pro Phe Gly Asp Ser Tyr Ile Val Ile Gly Asn Gly Asn
                85                  90                  95

Ser Ala Leu Lys Leu Asn Trp Phe Leu Leu Gly Ser Ser Ile Gly Lys
            100                 105                 110

Gly Ser Gly Cys
        115
```

<210> SEQ ID NO 329
<211> LENGTH: 112
<212> TYPE: PRT
<213> ORGANISM: Flavivirus

<400> SEQUENCE: 329

```
Met Asp Lys Leu Gln Leu Lys Gly Met Ser Tyr Thr Met Cys Thr Gly
1               5                   10                  15

Lys Phe Lys Ile Glu Lys Glu Val Ala Glu Thr Gln His Gly Thr Val
            20                  25                  30

Val Val Lys Val Lys Tyr Glu Gly Glu Asp Ala Pro Cys Lys Ile Pro
        35                  40                  45

Phe Glu Ile Gln Asp Leu Gln Gly Lys Thr His Asn Gly Arg Leu Ile
    50                  55                  60

Thr Ala Asn Pro Ile Val Thr Asn Lys Asp Ser Pro Val Asn Ile Glu
65                  70                  75                  80

Ala Glu Pro Pro Phe Gly Glu Ser Tyr Ile Val Ile Gly Val Gly Asp
                85                  90                  95

Ser Ala Leu Lys Leu Asn Trp Phe Lys Lys Gly Ser Ser Ile Cys Lys
            100                 105                 110
```

<210> SEQ ID NO 330
<211> LENGTH: 22
<212> TYPE: PRT
<213> ORGANISM: Enterovirus

<400> SEQUENCE: 330

```
Gly Ala Tyr Thr Gly Leu Pro Asn Lys Lys Pro Ser Val Pro Thr Val
1               5                   10                  15

Arg Thr Ala Lys Val Gln
            20
```

<210> SEQ ID NO 331
<211> LENGTH: 22
<212> TYPE: PRT
<213> ORGANISM: Enterovirus -continued

```
<400> SEQUENCE: 331

Gly Ala Tyr Thr Gly Ile Pro Asn Gln Lys Pro Lys Val Pro Thr Leu
1               5                   10                  15

Arg Gln Ala Lys Val Gln
            20


<210> SEQ ID NO 332
<211> LENGTH: 22
<212> TYPE: PRT
<213> ORGANISM: Enterovirus

<400> SEQUENCE: 332

Gly Ala Tyr Ser Gly Ala Pro Lys Gln Val Leu Lys Lys Pro Ala Leu
1               5                   10                  15

Arg Thr Ala Thr Val Gln
            20


<210> SEQ ID NO 333
<211> LENGTH: 22
<212> TYPE: PRT
<213> ORGANISM: Enterovirus

<400> SEQUENCE: 333

Gly Ala Tyr Thr Gly Leu Pro Asn Gln Lys Pro Lys Val Pro Thr Ile
1               5                   10                  15

Arg Thr Ala Lys Val Gln
            20


<210> SEQ ID NO 334
<211> LENGTH: 22
<212> TYPE: PRT
<213> ORGANISM: Enterovirus

<400> SEQUENCE: 334

Gly Ala Tyr Thr Gly Leu Pro Asn Lys Lys Pro Asn Val Pro Thr Ile
1               5                   10                  15

Arg Thr Ala Lys Val Gln
            20
```